(12) United States Patent
Kaneko

(10) Patent No.: US 9,499,466 B2
(45) Date of Patent: Nov. 22, 2016

(54) DIENE-BASED CARBOXYLATE ANION AND SALT THEREOF, AND POLYMERIZABLE OR CURABLE COMPOSITION THEREOF

(75) Inventor: Tomomasa Kaneko, Suita (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 634 days.

(21) Appl. No.: 13/877,751

(22) PCT Filed: Oct. 5, 2011

(86) PCT No.: PCT/JP2011/073019
§ 371 (c)(1),
(2), (4) Date: Apr. 4, 2013

(87) PCT Pub. No.: WO2012/046787
PCT Pub. Date: Apr. 12, 2012

(65) Prior Publication Data
US 2013/0197123 A1    Aug. 1, 2013

(30) Foreign Application Priority Data

Oct. 6, 2010  (JP) .................................. 2010-226984
Oct. 22, 2010  (JP) .................................. 2010-237775

(51) Int. Cl.
*C07C 57/13*    (2006.01)
*C07C 59/60*    (2006.01)
(Continued)

(52) U.S. Cl.
CPC .............. *C07C 57/13* (2013.01); *C07C 59/60* (2013.01); *C07C 69/734* (2013.01); *C07F 5/00* (2013.01);
(Continued)

(58) Field of Classification Search
CPC ..... C07C 57/13; C07C 69/734; C07C 59/60; C08F 136/20; C07F 7/006; C07F 15/025; C07F 7/2228; C07F 5/00; C07F 15/045; C07F 9/94; C07F 9/005
See application file for complete search history.

(56) References Cited

U.S. PATENT DOCUMENTS

2011/0263805 A1   10/2011   Kaneko
2012/0016095 A1   1/2012    Saito et al.

FOREIGN PATENT DOCUMENTS

CN        101657475        2/2010
JP        50-52027         5/1975
(Continued)

OTHER PUBLICATIONS

International Search Report issued Jan. 17, 2012 in International (PCT) Application No. PCT/JP2011/073019.
(Continued)

*Primary Examiner* — Michael Pepitone
*Assistant Examiner* — Jessica Roswell
(74) *Attorney, Agent, or Firm* — Wenderoth, Lind & Ponack, L.L.P.

(57) ABSTRACT

The claimed invention provides a novel compound not having been studied before, that is, a diene carboxylate anion that contains a specific structure, and a salt thereof. The claimed invention further provides a diene carboxylate anion and a salt thereof, especially a metal salt thereof, which are easily soluble in general organic solvents, reactive diluents, and resins, may be in a liquid state at normal temperature depending on the structure, and have high polymerizability. Polymerization/curing of these produces a resin to which many ionic bonds and a metal are introduced, providing various properties such as hardness, scratch resistance, anti-fingerprint property, gas-barrier property, water vapor barrier property, oxygen absorption property, ultraviolet protection, infrared protection, color development and coloring, high refractive index, adhesion, various catalytic abilities, fluorescence ability and light-emitting ability, optical amplification, dispersibility, and antistatic properties. In addition, the anion and the salt can be used for raw materials for functional fine particles and for metal nanoparticle composites, and also for MOD materials. The claimed invention also provides an advantageous method for producing the diene carboxylate anion and the salt thereof.

19 Claims, 41 Drawing Sheets

(51) Int. Cl.

| | | |
|---|---|---|
| *C07F 5/00* | (2006.01) | |
| *C07F 7/00* | (2006.01) | |
| *C07F 7/22* | (2006.01) | |
| *C08F 136/20* | (2006.01) | |
| *C07C 69/734* | (2006.01) | |
| *C07F 9/00* | (2006.01) | |
| *C07F 9/94* | (2006.01) | |
| *C07F 15/02* | (2006.01) | |
| *C07F 15/04* | (2006.01) | |

(52) U.S. Cl.
CPC ............ *C07F 7/006* (2013.01); *C07F 7/2228* (2013.01); *C07F 9/005* (2013.01); *C07F 9/94* (2013.01); *C07F 15/025* (2013.01); *C07F 15/045* (2013.01); *C08F 136/20* (2013.01)

(56) References Cited

FOREIGN PATENT DOCUMENTS

| | | |
|---|---|---|
| JP | 10-226669 | 8/1998 |
| JP | 2010-37549 | 2/2010 |
| JP | 101657475 | 2/2010 |
| JP | 2010-168539 | 8/2010 |
| JP | 2010-235546 | 10/2010 |
| JP | 2011-74068 | 4/2011 |
| WO | 2008/100309 | 8/2008 |

OTHER PUBLICATIONS

O. Wiest et al., "Stabilization of the Transition State of the Chorismate-Prephenate Rearrangement: An ab Initio Study of Enzyme and Antibody Catalysis", Journal of the American Chemical Society, 1995, vol. 117, No. 47, pp. 11628-11639.

J. Gajewski et al., "On the Mechanism of Rearrangement of Chroismic Acid and Related Compounds", Journal of the American Chemical Society, 1987, vol. 109, No. 4, pp. 1170-1186.

R. Thompson et al., "Unusually Facile Cyclopolymerization of a New Ally Ether Substituted Acrylate and Confirmation of Repeat Unit Structure by Inadequate NMR", Macromolecules, 1992, vol. 25, pp. 6455-6459.

M. Urushisaki et al., "Cyclopolymerization. 25. Five-Membered Ring Formation through Head-to-Head and Tail-to-Tail Additions in Radical and Anionic Polymerizations of α-(Allyloxymethyl)acrylates", Macromolecules, 1999, vol. 32, pp. 322-327.

Henryk Krawczyk, "The Mannich Reaction of Malonic Acid. An Efficient Route to Some α-Functionalized Acrylates", Synthetic Communications, 25(5), 1995, pp. 641-650.

Varinder K. Aggarwai et al., "A Palladium Catalysed Cyclisation-Carbonylation of Bromodienes: Control in Carbonylation Over Facile β-hydride Elimination", Chemical Communications, 2002, pp. 972-973.

X = OR
M = Ti (i) Polymerization mechanism of Formula (1)
Formula (1)

(ii) Polymerization mechanism of Formula (2)
Formula (2)

UV curing→
After being left to stand overnight

After re-irradiation (only left half) with UV light

After being left to stand for another night

DIENE-BASED CARBOXYLATE ANION AND SALT THEREOF, AND POLYMERIZABLE OR CURABLE COMPOSITION THEREOF

TECHNICAL FIELD

The claimed invention relates to a diene carboxylate anion usable as a raw material of a polymerized/cured product or a curable material for various industrial applications; a salt of the diene carboxylate anion, especially a metal salt thereof; a polymerizable/curable composition containing the anion or the salt; a method for polymerizing/curing the polymerizable/curable composition; and a polymerized or cured product produced by the method.

BACKGROUND ART

An anion is a substance with a negative charge, and exists in an electrolyte solution or an ionic substance (so-called salt). There are various types of anions such as inorganic anions and organic anions. Among the various types of anions, a polymerizable unsaturated carboxylate anion that is an organic anion is polymerizable in an electrolyte solution such as an aqueous solution, and is often polymerized/cured in an aqueous solution in which it is present as a salt with a metal cation, an organic cation, or the like. A polymerized/cured product produced therefrom is mainly used in aqueous applications. Examples of such polymerizable unsaturated carboxylate anion include (meth)acrylate anions, malate anions, and itaconate anions. In particular, (meth)acrylate anions have high polymerizability, and therefore are industrially important.

The term "salt" refers to an ionic substance which contains an anion and a counter cation, and is electrically neutral (electrically neutralized) as a whole substance. Salts are broadly categorized into two groups: inorganic salts consisting of inorganic substances only and organic salts including an organic substance. Industrially important among organic salts are metal salts of polymerizable unsaturated carboxylic acids, which contain a polymerizable unsaturated carboxylate anion and a metal cation. The metal salts of polymerizable unsaturated carboxylic acids show reactivity attributed to their unsaturated bond and metal salt structure in polymerization/curing reactions and the like, and also give the resulting polymerized/cured product the characteristics derived from the carboxylate anion-metal cation ionic bond and the characteristics derived from the metal itself. Conventionally used metal salts of polymerizable unsaturated carboxylic acids include metal salts of polymerizable unsaturated carboxylic acids such as (meth)acrylic acid, maleic acid, and itaconic acid. In particular, (meth)acrylate metal salts are industrially important and widely used: the sodium salts and the potassium salts are used as raw materials of aqueous dispersants, detergents, and water-absorbing resins; and the zinc salts are used in wide applications such as rubbers (e.g. tires and golf balls) and as a crosslinking agent for a barrier layer of a gas barrier film. Moreover, (meth)acrylate salts of metals including magnesium, calcium, copper, and aluminum are available as industrial products or reagents. These metal salts of polymerizable unsaturated carboxylic acids enable a metal to be introduced to a resulting polymerized/cured product through the carboxylate anion-metal cation ionic bond (hereinafter, also simply referred to as an ionic bond). Thereby, the resulting product shows various properties such as dispersibility, water absorbability, high hardness, high elasticity, and gas-barrier property, which are the properties derived from one of or both of the ionic bond and the metal.

On the other hand, concerning polymerizable unsaturated carboxylic acid-based compounds for example, Non Patent Literatures 1 and 2 disclose compounds in which an allyloxymethyl group is introduced to α-position of an acrylic ester such as ethyl α-allyloxy methyl acrylate or methyl α-allyloxy methyl acrylate. These compounds are polymerizable compounds which contain a double bond activated by the conjugation with an adjacent carbonyl group, like in the case of (meth)acrylic esters. The Non Patent Literatures disclose that these compounds are cyclopolymerized by a radical addition polymerization mechanism, and soluble polymers are generated.

CITATION LIST

Non Patent Literature

Non Patent Literature 1: "Macromolecules" by Robert D. Thompson and two more authors, 1992, Vol. 25, pp. 6455-6459

Non Patent Literature 2: "Macromolecules" by Michio Urushizaki and four more authors, 1999, Vol. 32, pp. 322-327

SUMMARY OF INVENTION

Technical Problem

The conventional polymerizable unsaturated carboxylate anions and salts thereof are, however, less soluble in organic mediums with low polarity, and are mostly in a state of powder or a crystalline solid at normal temperature. Therefore, the conventional anions and salts thereof do not have sufficient solubility/compatibility with general organic solvents, reactive diluents, and resins, and cannot easily form a film by coating. In addition, the polymerizability is sometimes insufficient. Therefore, the purpose of using them, how to use, and the amounts are greatly limited. For example, it is difficult to use them in a method in which a polymerizable unsaturated carboxylate anion or a salt thereof is dissolved in a general solvent such as an organic solvent or a reactive diluent, and the resulting solution is applied to an object and then cured by heat, UV light, and the like.

Meanwhile, concerning polymerizable unsaturated carboxylic acid-based compounds, the nonpatent literatures disclose radical or anionic addition polymerization of a compound in which an allyloxymethyl group is introduced to α-position of an acrylic ester such as ethyl α-allyloxy methyl acrylate or methyl α-allyloxy methyl acrylate. However, the literatures do not mention about α-allyloxymethyl acrylate anions and salts thereof at all. The literatures do not either disclose that what kind of problems occur when the compound in which an allyloxymethyl group is introduced to α-position of an acrylic ester is used as a compound to be polymerized.

The claimed invention has been made in view of the above problems. The claimed invention provides a diene carboxylate anion, which is a new substance that has not been studied before, and a salt thereof. Specifically, the claimed invention provides a diene carboxylate anion with a higher polymerizability and a salt thereof, in particular, a metal salt thereof, which are easily soluble in various general solvents such as organic solvents, reactive diluents, and resins, and may be in a liquid state at normal temperature depending on the structure.

In addition, the claimed invention aims to provide a polymerizable/curable composition containing the diene carboxylate anion or the salt thereof; a method for polymerizing/curing the polymerizable/curable composition; and a polymerized/cured product produced by the polymerization/curing method, in other words, a polymerized/cured product having excellent characteristics given by an ionic bond, particularly a metal introduced therein. The characteristics are specifically hardness, scratch resistance, anti-fingerprint property, gas-barrier property, water vapor barrier property, oxygen absorption property, ultraviolet protection, infrared protection, color development and coloring, high refractive index, adhesion, various catalytic abilities, fluorescence ability and light-emitting ability, optical amplification, dispersibility, and antistatic properties, for example.

In addition, an advantageous method for producing the diene carboxylate anion and the salt thereof is also provided.

Solution to Problem

The present inventor focused and studied on 1,6-diene-2-carboxylic acid compounds and 1,5-diene-2-carboxylic acid compounds, and then found out that 1,6-diene-2-carboxylate anions, 1,5-diene-2-carboxylate anions, and salts thereof are new substances; have different characteristics from conventional polymerizable unsaturated carboxylate anions, salts thereof, and unsaturated carboxylic ester compounds in which an allyloxymethyl group is introduced to α-position of an acrylic ester; and show further useful characteristics. In other words, the present inventor found out that the diene carboxylate anions and salts thereof have quite excellent polymerizability, and that salts of the diene carboxylic acids are easily soluble in various general solvents such as organic solvents, reactive diluents, and resins, and can be in a liquid state at normal temperature depending on the structure. Thereby, the above problems have been successfully solved.

Furthermore, a polymerized/cured product produced from the anions or the salts thereof has excellent characteristics enabled by introduction of an ionic bond preferably with a metal, to the polymerized/cured product. The characteristics are specifically hardness, scratch resistance, anti-fingerprint property, gas-barrier property, water vapor barrier property, oxygen absorption property, ultraviolet protection, infrared protection, color development and coloring, high refractive index, adhesion, various catalytic abilities, fluorescence ability and light-emitting ability, optical amplification, dispersibility, antistatic properties, and the like. Accordingly, the present inventor conceived that the polymerized/cured product can be widely applied in various fields such as fields of information technology (IT), automobiles, architecture, medical treatment, and commodities, and thereby completed the claimed invention. Specific applications in those fields are coating materials, ionomer resins, adhesives, sealing materials, tackifiers, paints, pigment dispersion, reactive emulsifiers, reactive surfactants, dispersion of fine particles of metals or metal oxides, inks, resists, MOD materials, molding materials, gas barrier materials, water vapor barrier materials, oxygen absorption materials, lenses, dental materials, antimicrobial agents, rubbers, tires, lightings, solar cells, wiring materials, electrode materials, undercoat for plating, optical fibers, optical waveguides, superconducting materials, semiconductor chips, magnetic materials, memories, capacitors, and piezoelectrics.

Since the diene carboxylate anions and the salts thereof according to the claimed invention are new substances, methods for producing the anions and the salts should be also new. Here, a particularly efficient method for preparing these substances has been also found out. Such a method enables easy industrial production of the anion and the salt.

An aspect of the claimed invention is namely a 1,6-diene-2-carboxylate anion represented by Formula (1), or a 1,5-diene-2-carboxylate anion represented by Formula (2); and salts of these anions.

[Chem. 1]

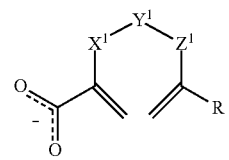

Formula (1)

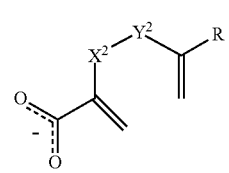

Formula (2)

In the formulas, Rs each independently represent a hydrogen atom or a methyl group. $X^1$, $Y^1$, $Z^1$, $X^2$, and $Y^2$, the same as or different from one another, each represent a methylene group, a methylene group in which a hydrogen atom is substituted by a methyl group, an oxygen atom, a sulfur atom, or an imino group. Here, at least one of $X^1$, $Y^1$, and $Z^1$ is an oxygen atom, a sulfur atom, or an imino group, and at least one of $X^2$ and $Y^2$ is an oxygen atom, a sulfur atom, or an imino group. In the formulas, the oxygen-carbon-oxygen bonds are shown by a dotted line and a solid line which mean that two carbon-oxygen bonds involved in each bond unit are equivalent to each other, and that the oxygen-carbon-oxygen bond as a whole forms a monovalent anion.

Another aspect of the claimed invention is an anion of α-(meth)allyloxymethyl acrylate represented by Formula (3) and a salt thereof.

[Chem. 2]

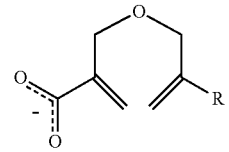

Formula (3)

In the formula, R represents a hydrogen atom or a methyl group. The oxygen-carbon-oxygen bond, shown by a dotted line and a solid line in the formula, as a whole forms a monovalent anion two carbon-oxygen bonds of which are equivalent to each other.

Another aspect of the claimed invention is an ionic composition including the diene carboxylate anion.

Still another aspect of the claimed invention is a polymerizable or curable composition including the diene carboxylate anion or the salt thereof.

Still more another aspect of the claimed invention is a method for polymerizing or curing the diene carboxylate anion, the salt thereof, or a polymerizable or curable composition including the anion or the salt, the method including a step including at least one method selected from the group consisting of heating, irradiating with active energy beam, and exposing to an atmosphere including oxygen.

Still yet another aspect of the claimed invention is a polymerized or cured product produced by the polymerization or curing method.

The details of the claimed invention are described in the following.

The following shows preferable embodiments of the claimed invention. The combination of two or more of each preferable embodiment is also a preferable embodiment of the claimed invention.

The following description relates to a diene carboxylate anion according to the claimed invention and a salt thereof and consists of: (1) basic chemical structure of the diene carboxylate anion and the salt thereof, (2) performance enabled by a diene carboxylate anion part and preferable structures of the diene carboxylate anion, (3) performance enabled by the counter cation part and preferable structures of the counter cation, (4) specific examples of the diene carboxylic acid salt according to the claimed invention, and (5) methods for producing the diene carboxylate anion and the salt thereof according to the claimed invention. Next, the description is focused on a composition that contains the diene carboxylate anion according to the claimed invention and/or the salt thereof, a method for polymerizing/curing the composition, and a polymerized/cured product produced therefrom.

<Diene Carboxylate Anion According to the claimed Invention and Salt Thereof>

(1) The following description relates to a basic chemical structure of the diene carboxylate anion and the salt thereof.

As shown in Formula (1) or Formula (2), the oxygen-carbon-oxygen bond as a whole forms a monovalent anion in the diene carboxylate anion according to the claimed invention. Similarly to conventional carboxylate anions, the diene carboxylate anion is solvated by solvent molecules and ionized in a high polar solvent such as water (in other words, a state of an electrolyte solution), and is present as an ionic substance containing an ionic bond between the anion and a counter cation (in other words, a salt) in a low polar solvent or a poor solvent, or with substantially no solvents. An ionic composition that contains the diene carboxylate anion of the claimed invention with the inclusion of the-above described is also one aspect of the claimed invention. As long as the ionic composition contains equivalent amounts of anions and counter cations and is electrically neutral as a whole, the anions and the counter cations may be bonded or may be in an ionized state. In addition, as long as the anions include the diene carboxylate anion of the claimed invention, anions other than the diene carboxylate anion of the claimed invention may be included. The details of the other anions and the counter cations are described later.

In the present description, the phrase substantially no solvents means that no solvents are used, and that a slight amount of a solvent is used so that the effects of the solvent are not exerted.

In order to confirm that the diene carboxylate anion is in a state of "anion", the same method as that applied to identification of a conventional carboxylate anion can be used. The method is described below.

Carboxylate anion (COO)⁻ is generally known to have a structure in which two carbon-oxygen bonds of the oxygen-carbon-oxygen bond are equivalent to each other, their bonding strength is in the middle of the bonding strength of C=O double bond and that of C—O single bond, and the oxygen-carbon-oxygen bond as a whole forms a monovalent anion, as shown in Formula (4) (refer to "Spectrometric identification of organic compounds", fourth edition, Tokyo Kagaku Dozin C., Ltd., p. 117, for example).

[Chem. 3]

Formula (4)

On the other hand, as shown in Formula (5), two carbon-oxygen bonds of the oxygen-carbon-oxygen bond are not equivalent in the case of a carboxylic acid or a carboxylic ester.

[Chem. 4]

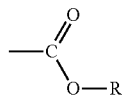

Formula (5)

In the formula, R represents a hydrogen atom or a hydrocarbon group.

The differences in equivalence of bonding and in bonding strength are clearly shown in infrared spectra. Carboxylic acids and carboxylic esters show a strong absorption band due to a C=O stretching vibration in the vicinity of 1700 to 1750 cm⁻¹, and an absorption band due to a C—O stretching vibration in the vicinity of 1200 cm⁻¹. On the other hand, carboxylate anions show absorption bands due to (COO)⁻ antisymmetric and symmetric stretching vibrations in the region between those of a C=O stretching vibration and a C—O stretching vibration. Generally, the absorption band of an antisymmetric stretching vibration coming in the vicinity of 1600 cm⁻¹ and the absorption band of a symmetric stretch coming in the vicinity of 1400 cm⁻¹ are considered to be the evidence of having a carboxylate anion structure (refer to "Spectrometric identification of organic compounds", fourth edition, Tokyo Kagaku Dozin C., Ltd., p. 118, for example).

The diene carboxylate anion of the claimed invention shows, similarly to conventional carboxylate anions, an absorption band of an antisymmetric stretching vibration in the vicinity of 1600 cm⁻¹ and an absorption band of a symmetric stretch vibration in the vicinity of 1400 cm⁻¹ in infrared spectra, although varieties occur to some extent depending on the concentration of the test sample, the kind of the solvent, the kind of the coexisting counter cation in an electrolyte solution or in an ionic substance. Specifically, the diene carboxylate anion of the claimed invention shows an absorption band of an antisymmetric stretching vibration in a region of lower frequency vibrations than the C=O stretching vibration of the corresponding diene carboxylic acid or a corresponding diene carboxylic ester, normally in a region of 1500 to 1650 cm⁻¹. The diene carboxylate anion of the claimed invention shows an absorption band of a symmetric stretch vibration in a region of higher frequency vibrations than the C—O stretching vibration of the corresponding diene carboxylic acid or a corresponding diene carboxylic ester, normally in a region of 1300 to 1500 cm⁻¹. When test samples containing the diene carboxylate anion of the claimed invention are analyzed by infrared spectroscopy, some examples may have almost no band of the C=O stretching vibration of a carboxylic acid, and others may have a considerably strong absorption band. This is because: in some cases, an excessive amount of a carboxylic acid as a raw material is added depending on synthesize conditions, whereby the carboxylic acid remains unreacted; and in some other cases, proton exchange occurs between a protic neutral low-molecular-weight compound such as remaining water or an alcohol and the diene carboxylate anion, whereby, a considerable strong absorption of a carboxylic acid due to a C=O stretching vibration is observed depending on the analytical conditions.

A specific phenomenon caused by the carboxylate anion structure is also observed in $^{13}$C-NMR spectra. For example, the absorption of the central carbon atom of a carboxylate anion is generally shifted to the low magnetic field side compared to the absorption of the carbonyl carbon atom of a corresponding carboxylic acid or the corresponding carboxylic ester in many cases. Similar phenomenon is often observed in the case of the diene carboxylate anion of the claimed invention.

The diene carboxylate anion of the claimed invention has hydrogen atoms $H_a$ and $H_b$ each having a double-bond character near the carboxylate anion structure as shown in Formula (6). Accordingly, the absorption bands due to these $H_a$ and $H_b$ in $^1$H-NMR spectra serve as good indications for confirmation of having a carboxylate anion structure. Specifically, compared with the hydrogen atoms having a double-bond character of the corresponding diene carboxylic acid or a corresponding diene carboxylic ester, the chemical shift values of $H_a$ and $H_b$ are more likely to shift to the high magnetic field side.

[Chem. 5]

Formula (6)

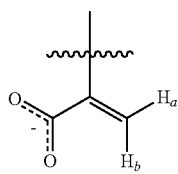

Here, the absolute values and the shift width of the chemical shift values of the characteristic absorptions in NMR spectra vary along with the concentration of the test sample, the kind of the solvent, and the kind of the coexisting counter cation in an electrolyte solution or in an ionic substance. In addition, depending on the kind of the counter cation, peaks are broadened due to formation of polymeric stable complexes, influence by paramagnetism, and the like, whereby detailed assignments may be difficult. Peaks are presumably broadened when, for example, a stable radical tends to be formed by bonding of a counter cation with oxygen in the air, which is paramagnetic, and when the counter cation itself is a paramagnetic substance. Such broad peaks are more likely to be observed when the counter cation contains a transition metal.

The diene carboxylate anion of the claimed invention may be analyzed by various chromatographic techniques. For example, analysis with gas chromatography or liquid chromatography is possible if an electrolyte solution containing the diene carboxylate anion of the claimed invention or a salt of the diene carboxylate anion of the claimed invention is pretreated with a strong acid to produce a diene carboxylic acid. Examples of the strong acid include sulfuric acid, hydrochloric acid, nitric acid, organic sulfonic acids, and phosphoric acid. Any of them may be selected according to the test samples and devices. Such a strong acid also make liquid chromatography usable if it is mixed into an elution solvent. Direct analysis on an ion itself is possible by use of ion chromatography or capillary electrophoresis.

The diene carboxylate anion of the claimed invention may be used, according to purposes and applications, as an electrolyte solution in which the anion is ionized or in an electrically neutral form bonded with a counter cation through an ionic bond (in other words, a state of a salt) in the presence of a low polar solvent, a poor solvent, or substantially with no solvents. The form bonded with a counter cation (a state of a salt) is one of preferable embodiments of the claimed invention. As mentioned above, one aspect of the claimed invention is a salt of a diene carboxylic acid being an ionic substance and electrically neutral as a whole (electrically neutralized), in which equivalent amounts of anions and counter cations are ionically bonded, and at least one valence of the counter cation is filled with the diene carboxylate anion of the claimed invention. In other words, one aspect of the claimed invention is a salt of a diene carboxylic acid being an ionic substance and electrically neutral as a whole (electrically neutralized), in which equivalent amounts of anions and counter cations are ionically bonded, and at least one of the anions is the diene carboxylate anion of the claimed invention.

The salts of a diene carboxylic acid of the claimed invention may each have, similarly to the case of general carboxylic acid salts, different coordinate structures even though the salts are represented by the same chemical formula each other (namely, even though the ratio of the diene carboxylate anion and that of the counter cation is the same), depending on the conditions such as the structure and the kind of the counter cation, the solvent, the concentration of the test sample, and the temperature. Since these different coordinate structures are easily reversibly converted to each other, different coordinate structures often coexist. Therefore, isolation, identification, and quantitative determination of these coordinate structures are not easy.

Such a phenomenon tends to occur when the counter cation can have a different coordination numbers, and particularly when the counter cation is a metal atom or an atomic group of metal atoms. For example, a salt represented by the formula $(RCOO)_2M$ (RCOO: a carboxylate anion, M: a metal cation) can have different coordinate structures as shown in FIG. 1. It should be noted that FIG. 1 only shows some coordinate structures, not showing all of them.

Thus, a counter cation that can have different coordination numbers allows carboxylate anions to be coordinated in different ways, and therefore they can form salts having different coordinate structures that are represented by the same chemical formula.

Carboxylate anions generally are known to be coordinated in different ways, specifically as unidentate ligands, bidentate ligands, bridging ligands, and the like (refer to Non Patent Literatures 3 to 5, for example).

Non Patent Literature 3: BASIC INORGANIC CHEMISTRY (SECOND EDITION), John Wiley & Sons, p. 143

Non Patent Literature 4: Principles and Applications of Organotransition Metal Chemistry, UNIVERSITY SCIENCE BOOKS, p. 59

Non Patent Literature 5: ADVANCED INORGANIC CHEMISTRY (FIFTH EDITION), John Wiley & Sons, p. 483

Also many other anions, in addition to the carboxylate anions shown in the above, are coordinated into a structure that is not exactly represented by a chemical formula. For example, titanium tetra-alkoxide normally represented by Ti(OR)$_4$, which consists of alkoxide ions (RO$^-$) and titanium, is known to be a polymer having a tetrameric structure as shown in FIG. 2 (refer to BASIC INORGANIC CHEMISTRY (SECOND EDITION), John Wiley & Sons, p. 142, for example).

Accordingly, the salt of a diene carboxylic acid of the claimed invention does not rely on a concept in which the salt should have a sole coordinate structure, but on a concept in which the salt may have different coordinate structures as long as the salts are represented by the same chemical formula (namely, as long as the ratio of the diene carboxylate anion and that of the counter cation is the same). Specifically, the salt of a diene carboxylic acid of the claimed invention rely on a concept in which different coordinate structures of the salt are considered to be the same as long as they are represented by the same formula (no matter if the salt may have a single coordinate structure or the salt may have different coordinate structures).

In the salt of a diene carboxylic acid of the claimed invention, at least one valence of the counter cation is filled with the diene carboxylate anion of the claimed invention, and the rest valences may be filled with anions (anionic ligands) other than the diene carboxylate anion of the claimed invention. The counter cations may be coordinated with a neutral molecule (neutral molecule ligand) with electron pair donating ability, in addition to the diene carboxylate anion of the claimed invention and other anions. Examples of such an anion (anionic ligand) include an oxide anion (O$^{2-}$), a halogen ion, a hydroxide ion, an alkoxide ion, a carboxylate anion other than the diene carboxylate anion of the claimed invention, an acetylacetonate ion, a carbonate ion, a hydrogen carbonate ion, a nitric acid ion, a nitrite ion, a sulfuric acid ion, a sulfite ion, a bisulfite ion, a phosphate ion, a silicate ion, and a borate ion. Examples of the neutral molecule ligand include water, alcohols, ammonia, amines, phosphines, β-ketoesters, and cyclopentadienes. Many other anions (anionic ligands) and neutral molecule ligands are also known to be usable, and these are mentioned in Non Patent Literatures 3 to 5, for example, which are technical books about inorganic chemistry and organic metal chemistry. The salt of a diene carboxylic acid of the claimed invention may have only one anionic ligand or neutral molecule ligand, or may also have two or more of anionic ligands or neutral molecule ligands including different kinds of them according to the valence number and coordinate number of counter cations.

From the above, the salt of a diene carboxylic acid of the claimed invention is represented by at least a combination of a chemical formula of a diene carboxylate anion and a chemical formula of a counter cation. In some cases, the salt is represented by a combination of chemical formulas further including a chemical formula of an anion (anionic ligand) other than the diene carboxylate anion and/or a chemical formula of a neutral molecule ligand. The ratio of the diene carboxylate anion, the counter cation, the anion (anionic ligand) other than the diene carboxylate anion, and the neutral molecule ligand is shown by the smallest integer ratio. When the diene carboxylate anion is represented by RCOO, the anion (anionic ligand) other than the diene carboxylate anion is represented by X, the neutral molecule ligand is represented by L, and the counter cation is represented by M, the diene carboxylic acid of the claimed invention is represented by "(RCOO)$_a$(X)$_b$(L)$_c$(M)$_d$" (wherein a and d each indicate an integer of 1 or more, and b and c each indicate an integer of 0 or more, and the proportions of the components are shown by the numbers a, b, c, and d). The neutral molecule ligand L, in some cases, has difficulty in determining whether it is incorporated in a salt or present as an impurity substance in a mixture containing the salt.

(2) The following is the description relating to the performance enabled by the anion part of a diene carboxylic acid and preferable structures of the diene carboxylate anion.

The diene carboxylate anion of the claimed invention has a quite excellent polymerizability/curability, and the polymerizability/curability is exerted both in a state that the anion is solvated with a solvent molecule and ionized in a high polar solvent such as water (in other words, a state of an electrolyte solution), and in a state of an ionic substance (in other words, a state of a salt) in which the anion is ionilcally bonded with a counter cation in a low polar solvent or a poor solvent, or with substantially no solvents.

This is presumably because the diene carboxylate anion of the claimed invention can be cyclopolymerized by the mechanisms shown in FIG. 3. Therefore, a high polymerizability/curability can be achieved in spite of the steric crowding around the α-position of the double bond conjugating with a carbonyl group.

Preferred is the mechanism (i) in FIG. 3, in which a polymer with a 5- or 6-membered ring structure in the main chain is formed via a stable 5- or 6-membered ring structure, in terms of polymerization activity. Specifically, one aspect of the claimed invention is a diene carboxylate anion, and the diene carboxylate anion is preferably an anion of 1,6-diene-2-carboxylate represented by Formula (1). More preferred is the case of $X^1=Z^1=$a methylene group, $Y^1=$an oxygen atom, a sulfur atom, or an imino group, and still more preferred is the case of $X^1=Z^1=$a methylene group, $Y^1=$an oxygen atom, in other words, the case that the diene carboxylate anion is an anion of α-(meth)allyloxymethyl acrylic acid.

When the diene carboxylate anion of the claimed invention is used in a state of a salt, the salt of a diene carboxylic acid of the claimed invention is easily dissolved in various general solvents such as organic solvents, reactive diluents, and resins, and may be in a liquid state at normal temperature depending on the structure. This is because the diene carboxylate anion of the claimed invention contains many organic groups. In particular, when the diene carboxylate anion of the claimed invention has a structure represented by Formula (1), wherein $X^1$ and $Z^1$ are the same as or different from each other and each represent a methylene group or a methylene group in which a hydrogen atom is replaced by a methyl group, and $Y^1$ represents an oxygen atom; or when the diene carboxylate anion has a structure represented by Formula (2), wherein $X^2$ represents a methylene group or a methylene group in which a hydrogen atom is replaced by a methyl group, and $Y^2$ represents an oxygen atom, the anion has a large number of carbon atoms and contains an ether structure. Accordingly, the diene carboxylate anion of the claimed invention exerts excellent solubility or compatibility in various general solvents such as organic solvents, reactive diluents, and resins, including solvents having low to high polarities, and may be in a liquid state at normal temperature depending on the cases.

In the case that the diene carboxylate anion of the claimed invention is used in a state of a salt, and $Z^1$ in Formula (1) and $Y^2$ in Formula (2) each are a methylene group, or in other words, a (meth)allyl group is included in the structure, the anion can be polymerized/cured by a so-called oxygen curing (also referred to as oxidative polymerization) mechanism in the presence of active oxygen. Examples of typical compounds which are polymerized or cured by an oxygen curing mechanism include polyfunctional alkyl allyl ether compounds, and the curing mechanism is shown in FIG. 4 (FIG. 4 is a simplified schematic diagram and an actual oxygen curing mechanism is rather complicated). When $Z^1$ in Formula (1) or $Y^2$ in Formula (2) is a methylene group, polymerization/curing by the same mechanism as shown in FIG. 4 is possible.

The above shows that the diene carboxylate anion preferably has a structure represented by Formula (1), wherein R represents a hydrogen atom or a methyl group, $X^1=Z^1=$a methylene group, $Y^1=$an oxygen atom, a sulfur atom, or an imino group; and more preferably has a structure represented by Formula (1), wherein R represents a hydrogen atom or a methyl group; $X^1=Z^1=$a methylene group; and $Y^1=$an oxygen atom.

(3) The following description relates to the performance enabled by the counter cation part and preferable structures of the counter cation.

Another aspect of the claimed invention is a salt of a diene carboxylic acid that contains the diene carboxylate anion and a counter cation. The salt of a diene carboxylic acid of the claimed invention may be used in a state that the diene carboxylate anion and the counter cation are dissolved and ionized in a high polar solvent such as water (in other words, a state of an electrolyte solution), and also in a state of an ionic substance (in other words, a state of a salt), in which the anion is conically bonded with the counter cation in a low polar solvent or a poor solvent, or with substantially no solvents. Specifically, this aspect of the salt of a diene carboxylic acid of the claimed invention is an ionic composition that contains the diene carboxylate anion of the claimed invention.

Examples of the counter cations can be categolized into a group consisting of metal elements (metal atoms) or atomic groups including metal atoms, and a group consisting of atomic groups including non-metal atoms. Examples of the former group includes alkali metal ions such as sodium ion and potassium ion, and examples of the latter group include cationized ions (also referred to as onium ions) of typical non-metal elements represented by quaternary ions (such as ammonium ion and phosphonium ion) of group 15 elements.

In the case that the counter cation is an atomic group containing both metal atoms and non-metal atoms, the whole atomic group including metal atoms and non-metal atoms can be conveniently regarded as a cation (for example, $[ZrO]^{2+}$, $[(C_2H_5O)Al]^{2+}$, $[(n-C_4H_9)_2Sn\text{—}O\text{—}Sn(n-C_4H_9)_2]^{2+}$), and the like). Or alternatively, from a viewpoint focusing on electronegativity differences, metal atoms or an atomic group consisting of only metal atoms may be regarded as cations, and other parts may be regarded as anions ($[ZrO]^{2+}$ is regarded as a combination of $Zr^{4+}$ and $O^{2-}$, $[(C_2H_5O)Al]^{2+}$ as a combination of $Al^{3+}$ and $C_2H_5O^-$, $[(n-C_4H_9)_2Sn\text{—}O\text{—}Sn(n-C_4H_9)_2]^{2+}$ as a combination of two of $Sn^{4+}$, $O^{2-}$, and two of $n-C_4H_9^-$). As long as the salt of a diene carboxylic acid of the claimed invention essentially contains the diene carboxylate anion of the claimed invention, and as a whole is electrically neutral, the counter cation may be regarded as a cation formed from an atomic group containing metal atoms and non-metal atoms, or may also be strictly regarded as a metal atom or an atomic group containing only metal atoms, with other parts regarded as anions.

In particular, in the case that the counter cation is a cation of a metal atom or an atomic group containing metal atoms, the polymerized/cured product produced from the salt of a diene carboxylic acid of the claimed invention can be given not only characteristics enabled by ionic bonds but also characteristics enabled by the metal itself, whereby the polymerized/cured product is of valuable use. Accordingly, the salt of a diene carboxylic acid of the claimed invention is more preferably a salt of a diene carboxylic acid in which the counter cation is a metal atom or an atomic group containing metal atoms (hereinafter, also simply referred to as a metal salt of a diene carboxylic acid).

The metal atoms (metal elements) refer to typical metal elements or transition metal elements. Typical metals generally include alkali metals (elements belonging to group 1 of the periodic table, except for hydrogen); alkaline-earth metals (elements belonging to group 2 of the periodic table); elements belonging to group 12 of the periodic table; elements belonging to group 13 of the periodic table, except for boron; elements belonging to group 14 of the periodic table, except for carbon and silicon; elements belonging to group 15 of the periodic table, except for nitrogen, phosphorus, and arsenic; and elements belonging to group 16 of the periodic table, except for oxygen, sulfur, selenium, and tellurium. In the claimed invention, however, elements sometimes categorized to metalloid, such as boron, silicon, arsenic, selenium, and tellurium, are included in metal atoms. Transition metals refer to elements belonging to groups 3 to 11 of the periodic table.

The following mainly describes the case that the counter cation is a cation of a metal atom or an atomic group containing metal atoms (hereinafter, also simply referred to as metal ions), but the description does not intend to limit the counter cation of the salt of a diene carboxylic acid of the claimed invention to the following examples, or to exclude atomic groups composed of non-metal atoms (hereinafter, also referred to as organic cations).

When the salt of a diene carboxylic acid of the claimed invention which contains a metal ion as a counter cation is polymerized/cured to produce a resulting polymerized/cured product to which the metal is introduced, hard coating properties such as surface hardness and scratch resistance may be improved. In addition, passive barrier properties (such as oxygen barrier properties and water vapor barrier property) may be simultaneously improved. Moreover, if $Z^1$ in Formula (1) or $Y^2$ in Formula (2), both formulas representing a diene carboxylate anion, is a methylene group, namely, if the diene carboxylate anion contains a (meth)allyl group in the structure, barrier properties against oxygen can be exerted by an active mechanism (a mechanism of chemically absorbing oxygen). Accordingly, the polymerized/cured product can be suitably used in applications such as hard coat materials, sealants, protection films, molding materials, gas barrier materials, and water vapor barrier materials. These effects tend to appear when the metal ion is an ion with a high valence number and a dense cross-linked structure is formed by metal-mediated ionic bonds. Therefore, the metal included in the counter cation is preferably a metal which has a valence number of two or more, such as an alkaline-earth metal, a typical metal belonging to the groups 12 to 16 of the periodic table, and a transition metal belonging to groups 3 to 11 of the periodic table. In terms of availability of the metal and easiness of the synthesis, more preferred are magnesium, calcium, strontium, barium, scandium, yttrium, lanthanoids, titanium, zirconium, vanadium, niobium, tantalum, chromium, molybdenum, tungsten, manganese, iron, ruthenium, cobalt, rhodium, iridium, nickel, palladium, platinum, copper, silver, gold, zinc, aluminum, gallium, indium, silicon, germanium, tin, lead, antimony, and bismuth. If transition metal elements such as chromium, manganese, iron, and cobalt are used, the resulting product is usually colored. Therefore, if the resulting product is preferred to be not-colored, particularly preferably used are typical metals such as magnesium, calcium, strontium, barium, zinc, aluminum, gallium, indium, germanium, tin, lead, antimony, and bismuth; transition metals of group 3, such as yttrium and lanthanum; and transition metals of group 4, such as titanium and zirconium.

When the salt of a diene carboxylic acid of the claimed invention which contains a metal ion as a counter cation is polymerized/cured to produce a polymerized/cured product to which the metal is introduced, the refractive index may be enhanced because of the introduced metal in the polymerized or cured product. Such a product is finely used for optical materials such as lenses, optical films, and optical fibers. Generally, optical materials are advantageously preferred to be pale-colored or non-colored. From this viewpoint, when the polymerized/cured product is used for optical materials, examples of particularly preferred metal contained in the counter cation include typical metals such as magnesium, calcium, strontium, barium, zinc, aluminum, gallium, indium, germanium, tin, lead, antimony, and bismuth; transition metals of group 3, such as yttrium and lanthanum; and transition metals of group 4, such as titanium and zirconium.

When the salt of a diene carboxylic acid of the claimed invention which contains a metal ion as a counter cation is polymerized/cured to produce a polymerized/cured product to which the metal is introduced, electromagnetic waves in a specific wavelength range may be absorbed depending on the kind of the metal. Therefore, the salt can be used as a light cutting agent or polymerizable colorant for coloring. Accordingly, applications as ultraviolet protection, infrared protection, X-ray shielding, and colored filters are possible. Particularly preferred for optical cutoff filter with no-colored or pale colored are typical metals such as magnesium, calcium, strontium, barium, zinc, aluminum, gallium, indium, germanium, tin, lead, antimony, and bismuth; transition metals of group 3, such as yttrium and lanthanum; and transition metals of group 4, such as titanium and zirconium.

Preferred for colored filters (colorants) are transition metals of groups 5 to 11 such as vanadium, chromium, manganese, iron, cobalt, nickel, and copper. In particular, when the polymerized/cured product is used as a colorant, combination use of metals or combination use of a metal and an organic cation such as an ammonium salt or a phosphonium salt can provide light absorption characteristics, which cannot be possible by the use of a single metal ion. Various combinations of cations is acceptable for providing these characteristics, and a combination including a transition metal is particularly preferable. For example, combination use of copper and lanthanum gives light absorption characteristics showing brilliant blue, which is not possible by the use of copper only. The light absorption characteristics can be effectively changed not only by adjusting the counter cation part, but also by using an anion other than the diene carboxylate anion of the claimed invention or a neutral ligand such as an amine or phosphine.

When the salt of a diene carboxylic acid of the claimed invention which contains a metal ion including a rare-earth metal element as a counter cation is polymerized/cured to produce a polymerized/cured product to which the rare-earth element is introduced, fluorescence ability and light-emitting ability may be given. Accordingly, applications such as lighting, display devices, solar cells, and optical fibers are possible. For example, introduction of europium enables red fluorescent color development, and a polymerized/cured product to which erbium is introduced may be used for optical fibers using optical amplification. In addition, as well as the case of the coloring agent, the fluorescence ability and light-emitting ability can be adjusted by combination use of cations, or also by using an anion other than the diene carboxylate anion of the claimed invention or a neutral ligand such as an amine or phosphine. Rare-earth elements refer to 17 elements that include lanthanoids from lanthanum to lutetium, adding scandium and yttrium thereto.

When the salt of a diene carboxylic acid of the claimed invention which contains a metal ion as a counter cation is polymerized/cured to produce a polymerized/cured product to which the metal is introduced, the polymerized/cured product may show catalytic ability according to the introduced metal. Accordingly, the polymerized/cured product can be used as a solid catalyst. The metal salt of a diene carboxylic acid of the claimed invention is easily soluble in many solvents such as organic solvents, reactive diluents, and resins, which enables easy molding into various shapes such as films, membranes, and grains. Thereby, a solid catalyst with a preferable shape can be produced according to the purposes and ways of using. Appropriate metals may be selected according to desired reaction, and in terms of the kinds of available reactions, preferable are typical metals of groups 12 to 16 of the periodic table and transition metals of groups 3 to 11 of the periodic table. Specifically, titanium, zirconium, zinc, aluminum, tin, lead, and bismuth can be preferably used as a catalyst for various organic reactions, such as an urethane catalyst or a transesterification catalyst, and vanadium, chromium, manganese, cobalt, and cerium can be preferably used as an oxidation catalyst, for example. A polymerized/cured product produced from the salt of a diene carboxylic acid of the claimed invention that contains an ammonium salt or a phosphonium salt as a counter cation can also be used as a catalyst.

When the salt of a diene carboxylic acid of the claimed invention which contains a metal ion as a counter cation is polymerized/cured to produce a polymerized/cured product to which the metal is introduced, antimicrobial properties, bactericidal properties, fungiproof properties, and anti-biofouling properties may be given. Accordingly, applications such as antimicrobial coating, sterilized coating, fungiproof coating, and ship bottom paint are possible. Particularly preferred metals for such applications are metals such as zinc, copper, and silver. Similar effects may also be achieved by a polymerized/cured product produced from the salt of a diene carboxylic acid of the claimed invention that contains an onium ion as a counter cation, such as ammonium salt and a phosphonium salt.

A polymerized/cured product produced from the salt of a diene carboxylic acid of the claimed invention may show antistatic properties. Examples of the counter cation for such properties include metal ions with a high affinity for water, such as magnesium, calcium, and barium; and organic cations such as quaternary ions of group 15 elements, including an ammonium ion and a phosphonium ion.

A polymerized/cured product produced from the salt of a diene carboxylic acid of the claimed invention shows good adhesion not only to inorganic materials such as metals, metal oxides, and glass, but also to resin materials including triacetylcellulose (TAC), polyethylene terephthalate (PET), cycloolefin polymers (COP), AS resin, and ABS resin, and other various organic materials. Accordingly, applications for adhesives and primers are possible. The counter cation used for such applications may be a metal ion or may also be an organic cation, and may be appropriately selected according to the kind of the adherend.

The salt of a diene carboxylic acid of the claimed invention can be used as an undercoat agent for metal plating of a resin. Generally, the numbers of resins easily metal-plated are limited, and complicated pretreatments such as making the surface of the resin uneven for improving the adhesion and performing a treatment with a plating activator or a plating catalyst are required. However, using the salt of a diene carboxylic acid of the claimed invention as an undercoat agent may enable to omit a part or most part of the complicated pretreatments. The counter cation used for such properties may be a metal ion or an organic cation, and may be appropriately selected according to the kind of the resin or plating. Preferred is a counter cation containing a transition metal. A precious metal such as silver, gold, or platinum is particularly preferable because metal nanoparticles are generated when the resin including the precious metal is cured by UV irradiation, whereby nonelectrolytic plating is possible using the generated metal nanoparticles as cores, or electrolytic plating is possible depending on the situation. Combination with microfabrication technology using photocuring, such as photolithography and UV nanoimprint technology, enables formation of fine conductive wiring or a fine black matrix on a resin film without a heat treatment at a high temperature.

The salt of a diene carboxylic acid of the claimed invention contains a diene carboxylic acid part having a high affinity for organic components and also serving as a radically polymerizable part, and a cation part having a high affinity for water. Accordingly, the salt of a diene carboxylic acid can also serve as a reactive emulsifier or a reactive surfactant to emulsify hydrophobic organic materials in water while being radically polymerized. The counter cation used for such properties may be appropriately selected, according to the kind or the amount of the substance to be emulsified, from the range from high hydrophilic cations such as group 2 elements and ammonium salts to relatively hydrophobic cations such as zinc and tin. In the case that the resulting product is preferred to be non-colored, preferable are quaternary ions of group 15 elements such as an ammonium ion and a phosphonium ion, typical metal elements, and transition metal elements belonging to groups 3 and 4, which provide resulting products with less colored.

The salt of a diene carboxylic acid of the claimed invention contains a diene carboxylic acid part having a high affinity for organic components and a cation part having a high affinity for inorganic fine particles. Accordingly, the salt of a diene carboxylic acid can appropriately serve as a dispersant for dispersing inorganic fine particles in an organic medium. The counter cation used for such properties may be a metal ion or an organic cation, and may be appropriately selected according to the inorganic fine particles to be dispersed. When the counter cation is a metal ion, it can be appropriately used for dispersion of metal inorganic fine particles. When the counter cation is an ammonium ion or a phosphonium ion, the salt of the diene carboxylic acid can be prepared as a liquid with a low viscosity depending on the structure of the cation. Thereby, the salt of a diene carboxylic acid can serve as both a dispersant and a radically polymerizable reactive diluent. The salt of a diene carboxylic acid may be used not only for dispersion of inorganic fine particles but also for dispersion of organic fine particles such as organic pigments used for color filters and the like.

It is generally known that a metal salt of a carboxylic acid as a raw material can generate metal fine particles having a carboxylate part on the surface via a treatment such as hydrolysis, oxidation, reduction, or energy irradiation. The metal salt of a diene carboxylic acid of the claimed invention that contains a metal ion as a counter cation can also generate fine particles in the same manner. In other words, the metal salt of a diene carboxylic acid of the claimed invention can also generate polymerizable metal fine particles having a diene carboxylic acid part on the surface and showing excellent dispersibility in an organic medium.

The salt of a diene carboxylic acid of the claimed invention that contains a metal ion as a counter cation is useful as a raw material of a composite that contains metal nanoparticles or metal oxide nanoparticles. In particular, if the salt contains a metal (e.g. silver, gold) that is reduced to a metal atom from the ion form by UV irradiation, a composite in which metal nanoparticles are uniformly dispersed at a quite high concentration can be easily produced by UV irradiation that generates metal nanoparticles and causes curing at the same time. When the diameter of the metal nanoparticles is controlled to be about a few nm to 100 nm, the particles can serve as a material showing plasmon absorption which is a unique property of metal nanoparticles, and can be used for applications using plasmon absorption, such as color materials and sensors. Such particles can be also used as a conductive material depending on the diameter or the concentration of the metal particles. Such particles are processed by microfabrication technology using photocuring, such as photolithography and UV nanoimprint technology, to enable applications such as micro wiring and raw materials for metamaterials.

The salt of a diene carboxylic acid of the claimed invention that contains a metal ion as a counter cation can serve as a radical curable MOD (Metal Organic Decomposition) material. A conventional MOD material is a non-polymerizable and film-forming composition that contains a metal salt of a long-chain carboxylic acid showing solubility in organic solvents, or a metal alkoxide showing solubility in organic solvents. The MOD material is a material for producing a densified and crystallized metallic thin film by applying the MOD material on a substrate and drying the material to form a film, converting the film into a film of a metal or a metal oxide (hereinafter, also simply referred to as a metallic thin film) by decomposition of organic materials in the film at a high temperature, and then firing the metallic thin film. The conventional MOD material, however, requires a complicated process using expensive equipment, such as etching the metallic thin film with a positive resist and so on after formation of the metallic thin film, or irradiating high-power energy beams such as electron beams on the dried film and then firing and crystallizing only the irradiated part, in order to produce a microfabricated metallic thin film. In contrast, since the metal salt of a diene carboxylic acid of the claimed invention has a high radical curability, a simpler patterning process may be employed, such as a patterning process (photolithography) using a photomask and UV light, UV-curable nanoimprinting, direct writing with inexpensive energy beams such as visible-light laser or infrared laser, and heat-curable nanoimprinting.

Although a preferable metal varies according to the composition of the required metallic thin film, particularly preferable are metals finely used for products such as semiconductor chips, superconducting materials, magnetic materials, memories, capacitors, and piezoelectrics. Specific examples include strontium, barium, scandium, yttrium, lanthanoids, titanium, zirconium, hafnium, niobium, thallium, chromium, molybdenum, manganese, iron, cobalt, nickel, copper, silver, zinc, aluminum, gallium, indium, silicon, germanium, tin, lead, arsenic, antimony, bismuth, selenium, and tellurium. High radical curability and film-forming ability can be simultaneously achieved both in the case of mixing the salt of a diene carboxylic acid of the claimed invention and a conventional film-forming non-polymerizable metal salt to produce a complex salt, and in the case of mixing the salt of a diene carboxylic acid of the claimed invention and a conventional non-film-forming polymerizable metal salt to produce a complex salt. Accordingly, both cases can be appropriately applied for MOD materials.

A metal salt of a diene carboxylic acid of the claimed invention containing an alkali metal or an alkaline-earth metal can produce a polymer that swells or is soluble in an organic solvent or water. Such a polymer can be used as a material for dispersants, water-absorbing resins, and ion secondary batteries such as lithium-ion batteries. As mentioned below, alkali metal salts of the diene carboxylic acid of the claimed invention, especially its sodium salt and potassium salt, are also useful as intermediate materials for production of metal salts other than the sodium salt or potassium salt.

As mentioned above, the salt of a diene carboxylic acid of the claimed invention provides various different properties depending on the counter cation used together therewith. Accordingly, a preferable metal atom, a preferable non-metal atom, or a preferable atomic group containing these, each of which constitutes a counter cation, varies depending on the application of the salt of a diene carboxylic acid. Combination of the diene carboxylate anion of the claimed invention with another anion enables to control various properties according to applications, with the characteristics of the diene carboxylic acid of the claimed invention being remained. The diene carboxylate anion of the claimed invention has a great technical significance in capabilities of variety of combinations as mentioned, such as combinations with metal atoms, non-metal atoms, and atomic groups containing these, and of forming a salt of a diene carboxylic acid suitably used for various applications.

(4) The salt of a diene carboxylic acid of the claimed invention is described with reference to specific examples.

The salt of a diene carboxylic acid of the claimed invention, as mentioned above, does not rely on a concept in which the salt should have a sole coordinate structure, but on a concept in which the salt may have different coordinate structures as long as they are represented by the same formula. Specifically, the salt of a diene carboxylic acid of the claimed invention rely on a concept in which different coordinate structures of the salt are considered to be the same as long as they are represented by the same formula (no matter if the salt may have a single coordinate structure or the salt may have different coordinate structures).

The general chemical formula of the salt of a diene carboxylic acid of the claimed invention is represented by Formula (7).

[Chem. 6]

$[(A^1)_{a1}(A^2)_{a2}(A^3)_{a3}\ldots]$ $[(X^1)_{b1}(X^2)_{b2}(X^3)_{b3}\ldots][(M^1)_{d1}(M^2)_{d2}(M^3)_{d3}\ldots]$ $[(L^1)_{c1}(L^2)_{c2}(L^3)_{c3}\ldots]$  Formula (7)

In the formula, each of $A^1, A^2, A^3\ldots$ represents a diene carboxylate anion of the claimed invention and is different from one another, and a1, a2, a3 ... each represent an integer of 1 or more. Each of $X^1, X^2, X^2\ldots$ represents an anion (anionic ligand) other than the diene carboxylate anion of the claimed invention and is different from one another, and b1, b2, b3 ... each represent an integer of 0 or more. Each of $L^1, L^2, L^3\ldots$ represents an electron donating neutral molecule ligand and is different from one another, and c1, c2, c3 ... each represent an integer of 0 or more. Each of $M^1, M^2, M^3\ldots$ represents a counter cation containing an atom or an atomic group and is different from one another, and d1, d2, d3 ... each represent an integer of 1 or more. The symbols a1, a2, a3 ..., b1, b2, b3 ..., c1, c2, c3 ..., and d1, d2, d3 ... are the smallest numbers showing proportions in the formula.

The following shows some specific examples, and thereby describes the salt of a diene carboxylic acid of the claimed invention with chemical formulas only for the purpose of explaining the concept of the salt of a diene carboxylic acid of the claimed invention. These specific examples do not cover all the preferred examples, and the claimed invention is not limited to these examples.

The following description uses only α-allyloxymethyl-acrylate anions (AMA ions) as examples of the diene carboxylate anion in order for a simple description. However, this does not deny the case of containing other diene carboxylate anions or the case of containing multiple kinds of diene carboxylate anions.

First of all, the following are the simplest examples of the salts only containing an AMA ion and one kind of counter cation. An AMA ion is represented by "AMA". The formula $(CH_3)_4N$ represents a tetramethyl ammonium ion, and the formula $(Ph)_4P$ represents a tetraphenyl phosphonium ion. The electric charge (positive or negative) and valence number of each ion are omitted.

Li(AMA), Na(AMA), K(AMA), $(CH_3)(AMA)$, $(Ph)_4P(AMA)$, $Mg(AMA)_2$, $Ca(AMA)_2$, $Sr(AMA)_2$, $Ba(AMA)_2$, $Y(AMA)_3$, $La(AMA)_3$, $Ti(AMA)_4$, $Zr(AMA)_4$, $Cr(AMA)_3$, $Mn(AMA)_2$, $Fe(AMA)_3$, $Co(AMA)_2$, $Ni(AMA)_2$, $Cu(AMA)_2$, $Ag(AMA)$, $Zn(AMA)_2$, $Al(AMA)_3$, $In(AMA)_3$, and $Bi(AMA)_3$ The following shows examples of complexes containing the oxide anion in addition to AMA ions.

$Zr(O)(AMA)_2$ and $V(O)(AMA)_2$

These examples may also be represented as a salt of AMA ion and counter cation formed from an atomic group containing a metal element and a non-metal element. Specifically, $Zr(O)(AMA)_2$ may also be represented by $ZrO(AMA)_2$ that means a salt of AMA ions and a ZrO ion, and $V(O)(AMA)_2$ may also be represented by $VO(AMA)_2$ that means a salt of AMA ions and a VO ion.

The following shows examples of complexes with a carboxylate anion in addition to a AMA ion (s). In the examples, Ac represents an acetate anion, AA represents an acrylate anion, and MAA represents a methacrylate anion.

$Ca(AMA)_1(Ac)_1$, $Ba(AMA)_1(AA)_1$, $Zr(AMA)_2(MAA)_2$, $Zn(AMA)_1(AA)_1$, and $In(AMA)_2(MAA)_1$ The following shows examples of complexes with a carbanion(s) in addition to AMA ions. In the examples, $n\text{-}C_4H_9$ represents a n-butyl carbanion.

$(n\text{-}C_4H_9)_2Sn(AMA)_2$, and $(n\text{-}C_4H_9)_2Pb(AMA)_2$

These may be individually considered as a salt of an AMA ion and a $(n\text{-}C_4H_9)_2Sn$ ion, and a salt of an AMA ion and a $(n\text{-}C_4H_9)_2Pb$ ion.

The following shows examples of complexes with the oxide anion and a carbanion(s) in addition to AMA ions.

$(CH_3)_4Sn_2(O)(ANA)_2$

This may be considered as a salt of AMA ions and a $(CH_3)_2Sn\text{—}O\text{—}Sn(CH_3)_2$ ion.

The following shows examples of complexes with multiple kinds of counter cations.

(La)$_1$(Cu)$_2$(AMA)$_7$ and ((C$_2$H$_5$)$_3$NH)$_1$(Ag)$_1$(AMA)$_2$

The following shows examples of complexes with an anionic ligand(s) other than a carboxylate anion, and shown here are examples containing a hydroxide ion, an alkoxide ion, and a halogen ion.

(Ph)$_2$Sn(OH)$_1$(AMA)$_1$. (n-C$_4$H$_9$O)$_2$Ti(AMA)$_2$, and Y(Cl)(AMA)$_2$

The following shows examples of complexes with a neutral molecule ligand(s), and shown here are examples containing water, methanol, and 2,2'-bipyridine. Here, 2,2'-bipyridine is represented as bpy.

(H$_2$O)$_2$Zn(AMA)$_2$, (H$_2$O)$_1$(CH$_3$OH)$_1$Zn(AMA)$_2$, and (bpy)$_2$Sm(AMA)$_3$ It is often difficult to know that whether a substance generally usable as a solvent, such as water, methanol, diethyl ether, or tetrahydrofuran, is contained in a salt as a neutral molecule ligand, or as a residual solvent in a mixture containing the salt.

Thus, the salt of a diene carboxylic acid of the claimed invention is shown by a combination of a chemical formula representing a diene carboxylate anion, a chemical formula representing a neutral molecule ligand and an anion other than the diene carboxylate anion, and a chemical formula representing a counter cation.

The above specific examples of the anion other than the diene carboxylate anion, the neutral molecule ligand, and the counter cation are just a part of the examples and do not represent a limitation to these substances. For example, the examples shown in Non Patent Literatures 3 to 5 may also be applied.

(5) Methods for producing the diene carboxylate anion of the claimed invention and the salt thereof are described.

The methods for producing a diene carboxylate anion of the claimed invention are categorized into two large groups:

(i) a method of reacting a diene carboxylic acid or an anhydride of a diene carboxylic acid with a basic substance or a potential basic substance; and (ii) a method of hydrolyzing an ester of a diene carboxylic acid or diene carboxylonitrile with a basic substance or a potential basic substance to produce a salt of a diene carboxylic acid, followed by optionally exchanging its cation with another cation. The method (i) is a kind of neutralization reaction and is also called as direct method. The method (ii) may require these two steps depending on the cases. In particular, the second step of exchanging the cation with another cation is also called as double decomposition method. Performing these methods in an electrolyte solution provides an ionized diene carboxylate anion. In addition, the diene carboxylate anion can be formed into a diene carboxylic acid salt by performing these methods in a non-electrolyte solution or an electrolyte solution, followed by removing or replacing a solvent or by extracting. The basic substance and the potential basic substance can generate hydroxide ions by reaction with water (optionally heated) and examples thereof include organic bases (e.g. ammonia and amines), various elemental metals, metal oxides, metal hydroxides, and metal alkoxides (hereinafter, also simply referred to as bases).

Therefore, a raw material of the diene carboxylate anion of the claimed invention is selected from one of a diene carboxylic acid, an anhydride of a diene carboxylic acid, an ester of a diene carboxylic acid, and diene carboxylonitrile.

However, production of the structure of a diene acyl group shown in FIG. 5 is industrially disadvantageous, except for the method of converting α-position of an acrylic ester or an acrylonitrile. Accordingly, in industrial production lines, as shown in FIG. 6, an acrylic ester or an acrylonitrile as a raw material is firstly converted into an ester of a diene carboxylic acid or diene carboxylonitrile. Then, the ester or the nitrile is hydrolyzed with a base to produce a diene carboxylic acid salt, or is hydrolyzed with an acid to produce a diene carboxylic acid. In the case of further exchanging with another cation, the exchange is carried out by the direct method or the double decomposition method. Hydrolysis of an ester of a diene carboxylic acid or a diene carboxylonitrile is more preferably performed with a base in terms of less side reactions and less erosion of a reactor. Hydrolysis with an acid using an erosion-resistant reactor may be more preferred in the case that even a slight contamination of an alkali metal is not allowed.

Specifically, a preferable embodiment is a method for producing a diene carboxylate anion of the claimed invention and a salt thereof, including the step of hydrolyzing an ester of 1,6-diene-2-carboxylic acid or a 1,6-diene-2-carboxylonitrile, an ester of 1,5-diene-2-carboxylic acid or a 1,5-diene-2-carboxylonitrile with a basic substance, a potential basic substance, or an acid.

The following describes an industrially advantageous method for producing a diene carboxylate anion of the claimed invention and a salt thereof. As representative examples of a diene carboxylate anion of the claimed invention and a salt thereof, an α-allyloxymethylacrylate anion (AMA ion) and a salt thereof (AMA salt) are given. Described in the first is the method for producing an AMA ion and an AMA salt by hydrolyzing an ester of α-allyloxymethyl acrylic acid (AMA ester) or α-allyloxymethylacrylonitrile (AMA nitrile) with a base. Described in the second is double decomposition method in which an AMA salt obtained by the hydrolysis with a base is converted into another cation salt. Described in the third is a method for converting an AMA salt obtained by the hydrolysis with a base into an α-allyloxymethyl acrylic acid (AMA carboxylic acid), followed by producing another cation salt by direct method. The method for producing a diene carboxylate anion of the claimed invention and a salt thereof is however not limited to these processes.

First, the method for producing an AMA ion and an AMA salt by hydrolyzing an AMA ester or an AMA nitrile with a base is described.

In this method, a basic substance or a potential basic substance is stirred with an AMA ester or an AMA nitrile preferably in the presence of water, whereby the reaction proceeds. The raw material is more preferably an AMA ester in terms of biological safety, and the basic substance or the potential basic substance is preferably a hydroxide of an alkali metal or an alkaline-earth metal in terms of availability and reactivity. Since most AMA esters naturally separate from an alkali metal/alkaline-earth metal hydroxide or hydroxides aqueous solutions, the mixture is a suspension at the initial stage of the reaction. The mixture is gradually emulsified as the reaction proceeds, and mostly results in a uniform and transparent liquid. Therefore, the progress of the reaction tends to be easily observed. Preferable examples of the alkali metal or the alkaline-earth metal include lithium hydroxide, sodium hydroxide, potassium hydroxide, magnesium hydroxide, calcium hydroxide, strontium hydroxide, and barium hydroxide, and particularly preferred are sodium hydroxide and potassium hydroxide, in terms of availability and an easy progression of the reaction. In the case that the hydroxide of an alkali metal/alkaline-earth metal is used in a state of an aqueous solution, the concentration of the solution may be appropriately selected according to the conditions such as the kind of the AMA ester and the reaction temperature, and is preferably 0.1 to 60 mass %, more preferably 1 to 50 mass %, and most preferably 3 to 40 mass %. The AMA ester is preferably a lower ester in terms of easy hydrolysis, and particularly preferably a C1 to C5 ester such as a methyl, ethyl, propyl, butyl, glycidyl, and tetrahydrofurfuryl ester. The reaction temperature may be appropriately selected according to the concentration of the alkali hydroxide and the kind of the AMA ester, and is preferably −20 to 120° C., more preferably −10 to 100° C., and most preferably 0 to 80° C.

Next, the production method by double decomposition method is described.

In this method, cations are exchanged between an AMA salt containing a cation $M_a^+$ (referred to as "an $M_a$ salt of an AMA") and a raw material salt containing a cation $M_b^+$ (simply referred to as "a raw material $M_b$ salt") in a solvent dissolving the both salts, and optionally in the presence of a catalyst, whereby another AMA salt (referred to as "an $M_b$ salt of an AMA") containing a cation $M_b^+$ is produced. The solvent should be one which can even partially dissolve both the $M_a$ salt of an AMA and the raw material $M_b$ salt, and is preferably water or an alcohol, and most preferably water. The $M_a$ salt of an AMA is preferably a salt of an alkali metal or an alkaline-earth metal, and particularly preferably a sodium salt or a potassium salt in terms of availability and an easy progression of the reaction. The raw material $M_b$ salt is preferably a salt of a metal other than alkali metals and alkaline-earth metals, or an ammonium salt or a phosphonium salt. In the case that $M_a$ is sodium or potassium, $M_b$ may be an alkali metal or an alkaline-earth metal other than sodium and potassium. The raw material $M_b$ salt may be a salt with various acids soluble in a solvent, and is particularly preferably a water-soluble salt. Such a salt may be appropriately selected according to the object metal, and examples thereof include sulfates, nitrates, hydrochlorides, sulfonates, phosphates, perchlorates, hydrobromates, carbonates, and acetates. Particularly preferable are sulfates, nitrates, and hydrochlorides (metal chlorides) in terms of availability, water solubility, stability, and easiness in replacing metals. The reaction temperature may be appropriately selected according to the kinds of each cation ($M_a^+$, $M_b^+$) and is preferably −20 to 120° C., more preferably −10 to 100° C., and most preferably 0 to 80° C. The object $M_b$ salt of an AMA may be separated without a specific operation, or can be extracted and separated with an appropriate organic solvent (such as diethyl ether, toluene, and chloroform).

Next, described is the method for converting the AMA salt obtained by the hydrolysis with a base into an α-allyloxymethyl acrylic acid (AMA carboxylic acid), and then producing another cation salt by the direct method.

This process may include two steps: the step of obtaining an AMA carboxylic acid (former step) and the following step of obtaining another cation salt by the direct method (latter step). The former step is a step of treating an AMA salt with an acid (preferably a strong acid) in the presence of water, and the most preferable and simple way is mixing an aqueous solution of an AMA salt with a strong acid. Preferable examples of the acid include sulfuric acid, nitric acid, hydrochloric acid, organic sulfonic acids (such as p-toluene sulfonic acid), trifluoroacetic acid, phosphoric acid, and acidic ion-exchange resins (particularly preferable are ones of sulfonic acids). The reaction temperature is preferably −20 to 120° C., more preferably −10 to 100° C., and most preferably 0 to 80° C. Optionally, an AMA carboxylic acid may be isolated and purified before the latter step. The method for isolation and purification is not particularly limited, and examples thereof include extracting and separating with an appropriate organic solvent (such as diethyl ether, toluene, or chloroform). The latter step is a kind of neutralization reaction, and may be a step of mixing the AMA carboxylic acid obtained in the former step and a base selected according to the object cation. The reaction temperature is preferably −20 to 120° C., more preferably −10 to 100° C., and most preferably 0 to 80° C. The direct method is particularly effective when the object AMA salt is hydrolytic and thereby the synthesis thereof in an aqueous solution is difficult, when the AMA salt is water soluble and thereby the extraction thereof is difficult, and when bases (such as a metal hydroxide, an amine, or a phosphine) as a raw material can be easily available.

The salt of a diene carboxylic acid of the claimed invention may contain an anion other than the diene carboxylate anion of the claimed invention or a neutral molecule ligand. Such a salt can be easily obtained by, for example, hydrolysis with the above base, double decomposition method, or direct method. A salt of another carboxylate anion can be obtained, for example, by performing the hydrolysis with a base or an acid in the presence of another carboxylic ester or carboxylonitrile, or by double decomposition method in which $M_a$ salt of another carboxylic acid is used together with a $M_a$ salt of an AMA. In addition, the direct method in which another carboxylic acid is used together is also available. A salt of another anion $X^-$ (such as a sulfuric acid ion, a nitric acid ion, or a halogen ion) may be obtained, for example, by the double decomposition method in which a salt (for example, a divalent salt of $M_b(X)_2$) containing anions $X^-$ and a multivalent $M_b$ ion is used as a $M_b$ salt, and the amount of the $M_a$ salt of an AMA (namely, the amount of the AMA ion) is set to be less than $M_b$ in terms of valence. A neutral molecule ligand may be coodinated by using a reaction solution containing the object neutral molecule ligand. For example, the object neutral molecule ligand may be used as a solvent or added to a reaction solution in the method for hydrolysis, double decomposition method, or direct method.

In addition, another preferable method for obtaining a salt of a diene carboxylic acid of the claimed invention is a method of mixing two or more kinds of salts, and a complex salt can be particularly easily obtained by the method. For example, only mixing a $M_a$ salt of acrylic acid with an $M_a$ salt of an AMA provides a complex $M_a$ salt of acrylic acid-AMA carboxylic acid, the ratio of which follows the mixed ratio. Ina similar manner, mixing an $M_a$ salt of an AMA with an $M_b$ salt of an AMA provides an $M_a$-$M_b$ complex salt of an AMA carboxylic acid.

<Composition Containing a Diene Carboxylate Anion of the Claimed Invention or a Salt Thereof>

Another aspect of the claimed invention is a polymerizable/curable composition containing the diene carboxylate anion and the salt thereof. The polymerizable/curable composition of the claimed invention may optionally contain various additives in addition to the diene carboxylate anion and the salt thereof.

The expression "polymerizable/curable" herein may be understood as "polymerization or curing". However, since there are cases in which both curing and polymerization occur simultaneously, the expression means "polymerization and/or curing".

The additives are not particularly limited, and examples thereof include curing accelerators, solvents, reactive diluents, stabilizers, binder resins, fillers, color materials, and dispersants. Among these, curing accelerators such as radical initiators and dryers are preferably added because curing accelerators can more effectively extract the performance of the polymerizable/curable composition of the claimed invention. Another preferable embodiment of the polymerizable/curable composition of the claimed invention is a composition further including a radical initiator and/or a dryer.

In the following, (A) radical initiator, (B) dryer, and (C) other additives are separatedly described.

(A) Radical Initiator

Radical polymerization of the diene carboxylate anion of the claimed invention and the salt thereof is initiated by heating and/or irradiating with active energy beams such as electromagnetic waves or electron beams, which leads to polymerization/curing. Additional use of a radical initiator enables more effective curing.

Examples of the radical initiator include thermal radical initiators which generate a radical by heating, and photoradical initiators which generate a radical by irradiating with active energy beams. One or more of general radical initiator(s) can be used.

Also, one or more of general additive (s), such as a radical polymerization accelerator and a photosensitizer, is/are preferably added as needed.

A suitable thermal radical initiator is an organic peroxide initiator or an azo initiator, and specific examples thereof are shown below.

Organic peroxide initiators such as methyl ethyl ketone peroxide, cyclohexanone peroxide, methyl cyclohexanone peroxide, methyl acetoacetate peroxide, acetyl acetate peroxide, 1,1-bis(t-hexyl peroxy)-3,3,5-trimethyl cyclohexane, 1,1-bis(t-hexyl peroxy) cyclohexane, 1,1-bis(t-butyl peroxy)-3,3,5-trimethyl cyclohexane, 1,1-bis(t-butyl peroxy)-2-methyl cyclohexane, 1,1-bis(t-butyl peroxy)cyclohexane, 1,1-bis(t-butyl peroxy)cyclo dodecane, 1,1-bis(t-butyl peroxy)butane, 2,2-bis(4,4-di-t-butyl peroxy cyclohexyl) propane, p-menthane hydroperoxide, diisopropyl benzene hydroperoxide, 1,1,3,3-tetramethyl butyl hydroperoxide, cumene hydroperoxide, t-hexyl hydroperoxide, t-butyl hydroperoxide, α,α-bis(t-butyl peroxy)diisopropyl benzene, dicumyl peroxide, 2,5-dimethyl-2,5-bis(t-butyl peroxy) hexane, t-butyl cumyl peroxide, di-t-butyl peroxide, 2,5-dimethyl-2,5-bis(t-butyl peroxy)hexyne-3, isobutyryl peroxide, 3,5,5-trimethyl hexanoyl peroxide, octanoyl peroxide, lauroyl peroxide, stearoyl peroxide, succinic acid peroxide, m-toluoyl benzoyl peroxide, benzoyl peroxide, di-n-propyl peroxy dicarbonate, diisopropyl peroxy dicarbonate, bis(4-t-butyl cyclohexyl) peroxy dicarbonate, di-2-ethoxy ethyl peroxy dicarbonate, di-2-ethoxy hexyl peroxy dicarbonate, di-3-methoxy butylperoxy dicarbonate, di-s-butylperoxy dicarbonate, di(3-methyl-3-methoxy butyl)peroxy dicarbonate, α,α'-bis(neo decanoyl peroxy)diisopropyl benzene, cumyl peroxy neodecanoate, 1,1,3,3,-tetramethylbutylperoxy neodecanoate, 1-cyclohexyl-1-methylethylperoxy neodecanoate, t-hexyl peroxy neodecanoate, t-butyl peroxy neodecanoate, t-hexyl peroxy pivalate, t-butyl peroxy pivalate, 1,1,3,3-tetramethyl butylperoxy-2-ethyl hexanoate, 2,5-dimethyl-2,5-bis(2-ethylhexanoylperoxy)hexanoate, 1-cyclohexyl-1-methylethylperoxy-2-ethyl hexanoate, t-hexyl peroxy-2-ethyl hexanoate, t-butyl peroxy-2-ethyl hexanoate, t-hexyl peroxy isopropyl monocarbonate, t-butyl peroxy isobutyrate, t-butyl peroxymalate, t-butyl peroxy-3,5,5-trimethyl hexanoate, t-butyl peroxylaurate, t-butyl peroxy isopropyl monocarbonate, t-butyl peroxy-2-ethylhexyl monocarbonate, t-butyl peroxyacetate, t-butyl peroxy-m-tolyl benzoate, t-butyl peroxybenzoate, bis(t-butyl peroxy) isophthalate, 2,5-dimethyl-2,5-bis(m-tolylperoxy)hexane, t-hexyl peroxybenzoate, 2,5-dimethyl-2,5-bis(benzoylperoxy)hexane, t-butyl peroxy allyl monocarbonate, t-butyl trimethylsilyl peroxide, 3,3',4,4'-tetra(t-butyl peroxycarbonyl)benzophenone, and 2,3-dimethyl-2,3-diphenylbutane.

Azo initiators such as 2-phenylazo-4-methoxy-2,4-dimethylvaleronitrile, 1-[(1-cyano-1-methylethyl) azo]formamide, 1,1'-azobis(cyclohexane-1-carbonitrile), 2,2'-azobis (2-methylbutyronitrile), 2,2'-azobis isobutyronitrile, 2,2'-azobis(2,4-dimethylvaleronitrile), 2,2'-azobis(2,4-dimethyl-4-methoxyvaleronitrile), 2,2'-azobis(2-methylpropionamidine) dihydrochloride, 2,2'-azobis(2-methyl-N-phenylpropionamidine) dihydrochloride, 2,2'-azobis[N-(4-chlorophenyl)-2-methylpropionamidine] dihydrochloride, 2,2'-azobis[N-(4-hydroxyphenyl)-2-methylpropionamidine]dihydrochloride, 2,2'-azobis[2-methyl-N-(phenylmethyl)propionamidine]dihydrochloride, 2,2'-azobis[2-methyl-N-(2-propenyl) propionamidine]dihydrochloride, 2,2'-azobis[N-(2-hydroxyethyl)-2-methylpropionamidine]dihydrochloride, 2,2'-azobis[2-(5-methyl-2-imidazolin-2-yl)propane]dihydrochloride, 2,2'-azobis[2-(2-imidazolin-2-yl)propane]dihydrochloride, 2,2'-azobis[2-(4,5,6,7-tetrahydro-1H-1,3-diazepine-2-yl) propane] dihydrochloride, 2,2'-azobis[2-(3,4,5,6-tetrahydropyrimidine-2-yl)propane]dihydrochloride, 2,2'-azobis[2-(5-hydroxy-3,4,5,6-tetrahydropyrimidine-2-yl) propane]dihydrochloride, 2,2'-azobis{2-[1-(2-hydroxyethyl)-2-imidazolin-2-yl]propane}dihydrochloride, 2,2'-azobis[2-(2-imidazolin-2-yl)propane], 2,2'-azobis{2-methyl-N-[1,1-bis(hydroxymethyl)-2-hydroxyethyl]propionamide}, 2,2'-azobis{2-methyl-N-[1,1-bis (hydroxymethyl) ethyl]propionamide}, 2,2'-azobis [2-methyl-N-(2-hydroxyethyl)propionamide], 2,2'-azobis(2-methylpropionamide), 2,2'-azobis(2,4,4-trimethylpentane), 2,2'-azobis(2-methylpropane), dimethyl-2,2-azobis(2-methyl propionate), 4,4' azobis(4-cyano-pentanoic acid), and 2,2'-azobis[2-(hydroxymethyl)propionitrile].

The radical polymerization accelerator usable with the thermal radical initiator may be a general accelerator which promotes decomposition of the thermal radical initiator (generation of an initiating radical), and is not particularly limited. Examples thereof include organic salts, inorganic salts, oxides, and metal complexes of metals such as cobalt, copper, tin, zinc, manganese, iron, zirconium, chromium, vanadium, calcium, potassium, cerium, and samarium; primary, secondary, and tertiary amine compounds; quaternary ammonium salts; thiourea compounds; and ketone compounds. Specific examples include cobalt octoate, cobalt naphthenate, zinc octoate, zinc naphthenate, zirconium octoate, zirconium naphthenate, copper octoate, copper naphthenate, manganese octoate, manganese naphthenate, dimethylaniline, triethanolamine, triethyl benzyl ammonium chloride, di(2-hydroxyethyl)p-toluidine, ethylene thiourea, acetylacetone, and methyl acetoacetate. In addition, the salt of a diene carboxylic acid of the claimed invention itself may also be used as such a radical polymerization accelerator.

Suitable examples of the photoradical initiator include alkylphenone compounds, benzophenone compounds, benzoin compounds, thioxanthone compounds, halomethylated triazine compounds, halomethylated oxadiazole compounds, biimidazole compounds, oxime ester compounds, titanocene compounds, benzoate compounds, and acridine compounds. Specific examples thereof are as follows.

Alkylphenone compounds such as 2,2-diethoxy acetophenone, 2,2-dimethoxy-2-phenylacetophenone, 1-hydroxycyclohexyl phenyl ketone, 2-hydroxy-2-methyl-1-phenylpropane-1-on, 1-[4-(2-hydroxyethoxy)phenyl]-2-hydroxy-2-methyl-1-propane-1-on, 2-hydroxy-1-{4-[4-(2-hydroxy-2- methylpropionyl) benzyl]phenyl}-2-methylpropane-1-on, 2-methyl-1-(4-methylthio phenyl)-2-morpholino propane 1-on, 2-benzyl-2-dimethylamino-1-(4-morpholino phenyl)-butanone-1, and 2-(dimethylamino)-2-[(4-methyl phenyl) methyl]-1-[4-(4-morpholinyl)phenyl]-1-butanone; benzophenone compounds such as benzophenone, 4,4'-bis (dimethylamino)benzophenone, and 2-carboxy benzophenone; benzoin compounds such as benzoin methyl ether, benzoin ethyl ether, benzoin isopropyl ether, and benzoin isobutyl ether; thioxanthone compounds such as thioxanthone, 2-ethyl thioxanthone, 2-isopropyl thioxanthone, 2-chloro thioxanthone, 2,4-dimethyl thioxanthone, and 2,4-diethyl thioxanthone; and halomethyl triazine compounds such as 2-(4-methoxyphenyl)-4,6-bis(trichloromethyl)-s-triazine, 2-(4-methoxynaphthyl)-4,6-bis (trichloromethyl)-s-triazine, 2-(4-ethoxynaphthyl)-4,6-bis (trichloromethyl)-s-triazine, and 2-(4-ethoxycarbonylnaphthyl)-4,6-bis(trichloromethyl)-s-triazine.

Halomethylated oxadiazole compounds such as 2-trichloromethyl-5-(2'-benzofuryl)-1,3,4-oxadiazole, 2-trichloromethyl-5-[β-(2'-benzofuryl)vinyl]-1,3,4-oxadiazo le, 4-oxadiazole, and 2-trichloromethyl-5-furyl-1,3,4-oxadiazole; biimidazole compounds such as 2,2'-bis(2-chlorophenyl)-4, 4',5,5'-tetraphenyl-1,2'-biimidazole, 2,2'-bis(2,4-dichlorophenyl)-4,4',5,5'-tetraphenyl-1,2'-biimidazole, and 2,2'-bis (2,4,6-trichlorophenyl)-4,4',5,5'-tetraphenyl-1,2'-biimidazole; oxime ester compounds such as 1,2-octanedion,1-[4-(phenylthio)-,2-(O-benzoyloxime)], and ethanone,1-[9-ethyl-6-(2-methylbenzoyl)-9H-carbazole-3-yl]-,1-(O-acetyloxime); titanocene compounds such as bis (η5-2,4-cyclopentadiene-1-yl)-bis(2,6-difluoro-3-(1H-pyrrole-1-yl)-phenyl)titanium; benzoic acid compounds such as p-dimethylamino benzoic acid and p-diethyl amino benzoic acid; and acridine compounds such as 9-phenyl acridine.

Use of a photosensitizer and a radical polymerization accelerator in addition to the photoradical initiator improves sensitivity and curability. The photosensitizer and the radical polymerization accelerator may be the one generally used and are not particularly limited. Preferably used are dye compounds, dialkylaminobenzene compounds, and mercaptan hydrogen donors. Examples thereof include dye compounds such as xanthene dyes, coumarin dyes, 3-ketocoumarin compounds, and pyrromethene dyes; dialkyl amino benzene compounds such as ethyl 4-dimethylaminobenzoate and 2-ethylhexyl 4-dimethylaminobenzoate; and mercaptan hydrogen donors such as 2-mercaptobenzothiazole, 2-mercaptobenzoxazole, and 2-mercaptobenzimidazole.

The total amount of the radical initiator may be appropriately set according to the purpose and the application, or the radical initiator does not have to be added. If the radical initiator is added, the amount is not particularly limited, and is preferably 0.01 to 30 mass % based on 100 mass % of the diene carboxylate anion of the claimed invention or the salt thereof, in terms of polymerizability/curability, the adverse effects of decomposition products, and a balance of economic efficiency. The amount is more preferably 0.05 to 20 mass %, and further preferably 0.1 to 15 mass %.

The total amount of the radical polymerization accelerator and the photosensitizer may be appropriately set according to the purpose and the application and is not particularly limited. In terms of factors such as polymerizability/curability and a balance of economic efficiency, the total amount is preferably 0.001 to 20 mass % based on 100 mass % of the diene carboxylate anion of the claimed invention or the salt thereof. The total amount is more preferably 0.05 to 10 mass %, and further preferably 0.01 to 10 mass %.

(B) Dryer

A dryer is a compound that promotes decomposition of peroxides, and namely decomposes peroxides to generate an oxide radical or a peroxide radical by a redox mechanism. One or more general dryer (s) may be used.

The dryer is not particularly limited, and examples thereof include organic salts, inorganic salts, oxides, and metal complexes of a metal such as cobalt, copper, tin, zinc, manganese, iron, zirconium, chromium, vanadium, calcium, potassium, cerium, and samarium; primary, secondary, and tertiary amine compounds; quaternary ammonium salts; thiourea compounds; and ketone compounds. Specific examples thereof include cobalt octoate, cobalt naphthenate, copper octoate, copper naphthenate, manganese octoate, manganese naphthenate, vanadium octoate, vanadium naphthenate, dimethylaniline, triethanolamine, triethyl benzyl ammonium chloride, di(2-hydroxyethyl)p-toluidine, ethylene thiourea, acetylacetone, and methyl acetoacetate. Also, the salt of a diene carboxylic acid of the claimed invention itself may have a function as a dryer.

The total amount of the dryer may be appropriately set according to the purpose and the application, or the dryer does not have to be added. If the dryer is added, the amount is not particularly limited, and is preferably 0.001 to 20 mass % based on 100 mass % of the diene carboxylate anion of the claimed invention or the salt thereof in terms of factors such as curability and a balance of economic efficiency. The amount is more preferably 0.05 to 10 mass %, and further preferably 0.01 to 10 mass %.

(C) Other Additives

Additives other than the above (A) radical initiator and (B) dryer are not particularly limited, and examples thereof include products such as a curing accelerator except for the radical initiator and the dryer, a solvent, a reactive diluent, a stabilizer, a binder resin, a color material (i.e. pigment, dye), a dispersant, a filler, an adhesion accelerator, a mold lubricant, a plasticizer, an ultraviolet absorber, an infrared absorbing agent, a matting agent, a defoaming agent, a leveling agent, an antistatic agent, a slip agent, a surface modifier, a silane, aluminum, or titanium coupling agent, and an acid generator. Major products among these are described below.

<Curing Accelerator Other than the Radical Initiator and the Dryer>

Examples of a curing accelerator other than the radical initiator and the dryer include multifunctional thiols. A multifunctional thiol may be used as a multifunctional chain transfer agent for radical curing. In addition, if the salt of a diene carboxylic acid of the claimed invention is a salt of an α-(meth)allyloxymethyl carboxylic acid, the salt of a diene carboxylic acid can also serve as a crosslinking agent in ene-thiol reaction because of its (meth)allyl ether group, whereby the curability of the salt of a diene carboxylic acid of the claimed invention is improved. The multifunctional thiol is not particularly limited as long as two or more of mercapto groups are included in a molecule. Examples thereof include trimethylol propane tris(3-mercaptopropionate), pentaerythritol tetrakis(3-mercaptopropionate), pentaerythritol tetrakis(3-mercaptobutyrate), dipentaerythritol hexakis(3-mercaptopropionate), 1,4-bis(3-mercaptobutyryloxy)butane, and 1,3,5-tris(3-mercaptobutyloxyethyl)-1,3,5-triazine-2,4,6-(1H,3H,5H)-trion. Each of these may be used alone, or two or more of them may be used in combination.

The total amount of the curing accelerator other than the radical initiator and the dryer may be appropriately set according to the purpose and the application and is not particularly limited. The total amount is preferably 0 to 150 mass % based on 100 mass % of the diene carboxylate anion of the claimed invention or the salt thereof. The total amount is more preferably 0 to 100 mass %, and further preferably 0 to 80 mass %.

The curing accelerator other than the radical initiator and the dryer is not an essential component of the polymerizable/curable composition of the claimed invention and is preferably not used depending on conditions such as the application and curing conditions. Thus, the total amount thereof may be 0 mass %.

<Solvent>

Solvents are used for lowering the viscosity of the polymerizable/curable composition by dilution, control of the thickness of coating, uniform mixing/dispersion of the components in the polymerizable/curable composition, and the like. The solvent may be a low-viscosity organic solvent or water which dissolves or disperses the components in the polymerizable/curable composition, may be the one generally used for polymerizable/curable compositions, and is not particularly limited. Examples thereof include the following substances.

Monoalcohols such as methanol, ethanol, isopropanol, n-butanol, and s-butanol; glycols such as ethylene glycol and propylene glycol; cyclic ethers such as tetrahydrofuran and dioxane; glycol monoethers such as ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, propylene glycol monomethyl ether, propylene glycol monoethyl ether, propylene glycol monobutyl ether, and 3-methoxybutanol; glycol ethers such as ethylene glycol dimethyl ether, ethylene glycol diethyl ether, ethylene glycol ethyl methyl ether, diethylene glycol dimethyl ether, diethylene glycol diethyl ether, diethylene glycol ethyl methyl ether, propylene glycol dimethyl ether, and propylene glycol diethyl ether; and esters of glycol monoethers, such as ethylene glycol monomethyl ether acetate, ethylene glycol monoethyl ether acetate, ethylene glycol monobutyl ether acetate, diethylene glycol monomethyl ether acetate, diethylene glycol monoethyl ether acetate, diethylene glycol monobutyl ether acetate, propylene glycol monomethyl ether acetate, propylene glycol monoethyl ether acetate, propylene glycol monobutyl ether acetate, dipropylene glycol monomethyl ether acetate, dipropylene glycol monoethyl ether acetate, dipropylene glycol monobutyl ether acetate, and 3-methoxy butyl acetate.

Alkyl esters such as methyl acetate, ethyl acetate, propyl acetate, isopropyl acetate, butyl acetate, methyl propionate, ethyl propionate, butyl propionate, methyl lactate, ethyl lactate, butyl lactate, methyl 3-methoxy propionate, ethyl 3-methoxy propionate, methyl 3-ethoxy propionate, ethyl 3-ethoxy propionate, methyl acetoacetate, and ethyl acetoacetate; ketones such as acetone, methyl ethyl ketone, methyl isobutyl ketone, and cyclo hexanone; aromatic hydrocarbons such as benzene, toluene, xylene, and ethyl benzene; aliphatic hydrocarbons such as hexane, cyclohexane, and octane; amides such as dimethylformamide, dimethylacetamide, and N-methylpyrrolidone; amines such as triethylamine, dibutylamine, tributylamine, octylamine, and pyridine; and water.

Each of these may be used alone, or two or more of them may be used in combination. Appropriate solvent(s) may be selected according to the purpose and the application.

The total amount of the solvent(s) may be appropriately set under considering the viscosity and the coatability of the polymerizable/curable composition and the like, according to the purpose and the application, and is not particularly limited. The total amount is preferably 0 to 2,000 mass % based on 100 mass % of the diene carboxylate anion of the claimed invention or the salt thereof. The total amount is more preferably 0 to 1,500 mass %, and further preferably 0 to 1,000 mass %.

The solvent is not an essential component of the polymerizable/curable composition, and is preferably not used depending on the conditions such as the applications and curing conditions. Thus, the total amount may be 0 mass %.

<Reactive Diluent>

A reactive diluent is a low-molecular compound containing a polymerizable group that is polymerized by heating or irradiating with active energy beams or the like. Particularly, reactive diluents being in a liquid state/having a low-viscosity at normal temperature have viscosity control function as well. Therefore, such a reactive diluent may be used instead of a solvent and is suitably used for solvent-free applications. General examples thereof include compounds containing a radically polymerizable group such as a group containing a carbon-carbon unsaturated bond; compounds containing a cationic polymerizable group such as an epoxy group, an oxetanyl group, and a vinyl ether group; and hybrid compounds containing both a radically polymerizable group and a cationic polymerizable group. If the curable composition of the claimed invention includes a reactive diluent, the reactive diluent may be the one generally used. One or more of reactive diluent (s) may be selected according to the purpose and the application, and no particular limitation is imposed. Since the metal salt of a diene carboxylic acid of the claimed invention is radically polymerizable, a reactive diluent is one containing a radically polymerizable group which can be cured by the same mechanism as the salt is preferably used to easily produce multiplier effects.

Radically polymerizable reactive diluents can be categorized into two groups: a group of monofunctional radically polymerizable monomers, containing only one radically polymerizable unsaturated group in a molecule; and a group of polyfunctional radically polymerizable monomers, containing two or more radically polymerizable groups in a molecule.

These radically polymerizable reactive diluents may also be used as monomers to be copolymerized to obtain a soluble polymer or crosslinked fine particles.

Specific examples of the monofunctional radically polymerizable monomer include the following.

(Meth)acrylate esters such as methyl (meth)acrylate, ethyl (meth)acrylate, n-propyl (meth)acrylate, i-propyl(meth) acrylate, n-butyl (meth)acrylate, s-butyl (meth)acrylate, t-butyl (meth)acrylate, n-amyl (meth)acrylate, s-amyl (meth)acrylate, t-amyl (meth)acrylate, n-hexyl (meth)acrylate, 2-ethylhexyl (meth)acrylate, isodecyl (meth)acrylate, tridecyl (meth)acrylate, cyclohexyl (meth)acrylate, cyclohexylmethyl (meth)acrylate, octyl (meth)acrylate, lauryl (meth)acrylate, stearyl (meth)acrylate, benzyl (meth)acrylate, phenyl (meth)acrylate, isobornyl (meth)acrylate, adamantyl (meth)acrylate, tricyclodecanyl (meth)acrylate, 2-hydroxyethyl (meth)acrylate, 2-hydroxypropyl (meth) acrylate, 3-hydroxypropyl (meth)acrylate, 2-hydroxybutyl (meth)acrylate, 3-hydroxybutyl (meth)acrylate, 4-hydroxybutyl (meth)acrylate, 2-methoxyethyl (meth)acrylate, 2-ethoxyethyl (meth)acrylate, phenoxyethyl (meth)acrylate, tetrahydrofurfuryl (meth)acrylate, glycidyl (meth)acrylate, β-methylglycidyl (meth)acrylate, β-ethylglycidyl (meth) acrylate, (3,4-epoxycyclohexyl)methyl (meth)acrylate, N,N-dimethylaminoethyl (meth)acrylate, methyl α-hydroxymethyl acrylate, and ethyl α-hydroxymethyl acrylate.

(Meth)acrylamides such as N,N-dimethyl (meth)acrylamide and N-methylol (meth)acrylamide; unsaturated monocarboxylates such as (meth)acrylate, crotonic acid, cinnamic acid, and vinyl benzoic acid; unsaturated multivalent carboxylic acids such as maleic acid, fumaric acid, itaconic acid, citraconic acid, and mesaconic acid; unsaturated monocarboxylates, wherein one or more repeating unit exist between an unsaturated group and a carboxyl group, such as mono(2-acryloyloxyethyl) succinate and mono(2-methacryloyloxyethyl) succinate; unsaturated acid anhydrides such as maleic anhydride and itaconic acid anhydride; aromatic vinyls such as styrene, α-methyl styrene, vinyl toluene, and methoxy styrene; N-substituted maleimides such as methylmaleimide, ethylmaleimide, isopropylmaleimide, cyclohexyl maleimide, phenylmaleimide, benzylmaleimide, and naphthylmaleimide; conjugated dienes such as 1,3-butadiene, isoprene, and chloroprene; vinyl esters such as vinyl acetate, vinyl propionate, vinyl butyrate, and vinyl benzoate; vinyl ethers such as methyl vinyl ether, ethyl vinyl ether, propyl vinyl ether, butyl vinyl ether, 2-ethylhexyl vinyl ether, n-nonyl vinyl ether, lauryl vinyl ether, cyclohexyl vinyl ether, methoxy ethyl vinyl ether, ethoxy ethyl vinyl ether, methoxyethoxy ethyl vinyl ether, methoxy polyethylene glycol vinyl ether, 2-hydroxyethyl vinyl ether, and 4-hydroxybutyl vinyl ether; N-vinyl compounds such as N-vinyl pyrrolidone, N-vinyl caprolactam, N-vinyl imidazole, N-vinyl morpholine, and N-vinyl acetamide; and unsaturated isocyanates such as isocyanatoethyl(meth)acrylate and allyl isocyanate.

Alternatively, the reactive diluent is preferably a carboxylic acid or an ester having the same structure as that of the diene carboxylate anion of the claimed invention, namely a compound represented by any of the following formulas.

[Chem. 7]

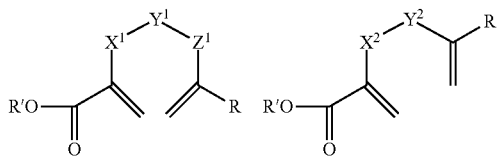

In the formula, Rs each represent a hydrogen atom or a methyl group. $X^1$, $Y^1$, $Z^1$, $X^2$, and $Y^2$ are the same as or different from one another, and each represent a methylene group, a methylene group in which a hydrogen atom is replaced by a methyl group, an oxygen atom, a sulfur atom, or an imino group. Here, at least one of $X^1$, $Y^1$, and $Z^1$ is an oxygen atom, a sulfur atom, or an imino group, and at least one of $X^2$ and $Y^2$ is an oxygen atom, a sulfur atom, or an imino group. R' represents a hydrogen atom or a monovalent organic group.

For excellent dilution ability, R' is particularly preferably a hydrogen atom, or a monovalent organic group with a hydrocarbon backbone having 12 or less carbon atoms and optionally an oxygen atom, such as a methyl, ethyl, propyl, butyl, 2-ethylhexyl, cyclohexyl, isobornyl, dicyclopentanyl, dicyclopentenyloxyethyl, benzyl, methoxy ethyl, or tetrahydrofurfuryl group.

Specific examples of the polyfunctional radically polymerizable monomer include the following.

Polyfunctional (meth)acrylates such as ethylene glycol di(meth)acrylate, diethylene glycol di(meth)acrylate, polyethylene glycol di(meth)acrylate, propylene glycol di(meth)acrylate, butylene glycol di(meth)acrylate, hexanediol di(meth)acrylate, cyclohexanedimethanol di(meth)acrylate, bisphenol A alkylene oxide di(meth)acrylate, bisphenol F alkylene oxide di(meth)acrylate, trimethylolpropane tri (meth)acrylate, ditrimethylolpropane tetra(meth)acrylate, glycerin tri(meth)acrylate, pentaerythritol tetra(meth)acrylate, dipentaerythritol penta(meth)acrylate, dipentaerythritol hexa(meth)acrylate, ethylene oxide adducts of trimethylol propane tri(meth)acrylate, ethylene oxide adducts of ditrimethylol propane tetra(meth)acrylate, ethylene oxide adducts of pentaerythritol tetra(meth)acrylate, ethylene oxide adducts of dipentaerythritol hexa(meth)acrylate, propylene oxide adducts of trimethylol propane tri(meth)acrylate, propylene oxide adducts of ditrimethylol propane tetra(meth) acrylate, propylene oxide adducts of pentaerythritol tetra (meth)acrylate, propylene oxide adducts of dipentaerythritol hexa(meth)acrylate, ε-caprolactone adducts of trimethylol propane tri(meth)acrylate, ε-caprolactone adducts of ditrimethylol propane tetra(meth)acrylate, ε-caprolactone adducts of pentaerythritol tetra(meth)acrylate, and ε-caprolactone adducts of dipentaerythritol hexa(meth)acrylate.

Polyfunctional vinyl ethers such as ethylene glycol divinyl ether, diethylene glycol divinyl ether, polyethylene glycol divinyl ether, propylene glycol divinyl ether, butylene glycol divinyl ether, hexanediol divinyl ether, bisphenol A alkylene oxide divinyl ether, bisphenol F alkylene oxide divinyl ether, trimethylol propane trivinyl ether, ditrimethylol propane tetravinyl ether, glycerin trivinyl ether, pentaerythritol tetravinyl ether, dipentaerythritol pentavinyl ether, dipentaerythritol hexavinyl ether, ethylene oxide adducts of trimethylol propane trivinyl ether, ethylene oxide adducts of ditrimethylol propane tetravinyl ether, ethylene oxide adducts of pentaerythritol tetravinyl ether, and ethylene oxide adducts of dipentaerythritol hexavinyl ether; and vinyl ether group-containing (meth)acrylate esters such as 2-vinyloxyethyl (meth)acrylate, 3-vinyloxypropyl (meth) acrylate, 1-methyl-2-vinyloxyethyl (meth)acrylate, 2-vinyloxypropyl (meth)acrylate, 4-vinyloxybutyl (meth)acrylate, 4-vinyloxycyclohexyl (meth)acrylate, 5-vinyloxypentyl (meth)acrylate, 6-vinyloxyhexyl (meth)acrylate, 4-vinyloxymethylcyclohexylmethyl (meth)acrylate, p-vinyloxymethylphenylmethyl (meth)acrylate, 2-(vinyloxyethoxy)ethyl (meth)acrylate, and 2-(vinyloxyethoxyethoxy)ethyl (meth)acrylate.

Polyfunctional allyl ethers such as ethylene glycol diallyl ether, diethylene glycol diallyl ether, polyethylene glycol diallyl ether, propylene glycol diallyl ether, butylene glycol diallyl ether, hexanediol diallyl ether, bisphenol A alkylene oxide diallyl ether, bisphenol F alkylene oxide diallyl ether, trimethylol propane triallyl ether, ditrimethylol propane tetraallyl ether, glycerin triallyl ether, pentaerythritol tetraallyl ether, dipentaerythritol pentaallyl ether, dipentaerythritol hexaallyl ether, ethylene oxide adducts of trimethylol propane triallyl ether, ethylene oxide adducts of ditrimethylol propane tetraallyl ether, ethylene oxide adducts of pentaerythritol tetraallyl ether, and ethylene oxide adducts of dipentaerythritol hexaallyl ether; allyl group-containing (meth)acrylate esters such as allyl (meth)acrylate; polyfunctional (meth)acryloyl group-containing isocyanurates such as tri(acryloyloxyethyl) isocyanurate, tri(methacryloyloxyethyl) isocyanurate, alkylene oxide adducts of tri(acryloyloxyethyl) isocyanurate, and alkylene oxide adducts of tri (methacryloyloxyethyl) isocyanurate; polyfunctional allyl group-containing isocyanurates such as triallyl isocyanurate; polyfunctional urethane(meth)acrylates obtainable by a reaction between a polyfunctional isocyanate (e.g. tolylene diisocyanate, isophorone diisocyanate, and xylylene diisocyanate) with a hydroxyl group-containing (meth)acrylate ester (e.g. 2-hydroxyethyl (meth)acrylate and 2-hydroxypropyl (meth)acrylate); polyfunctional aromatic vinyls such as divinyl benzene.

Alternatively, the reactive diluent is preferably an ester having the same structure as that of the diene carboxylate anion of the claimed invention, namely a compound represented by any of the following formulas.

[Chem. 8]

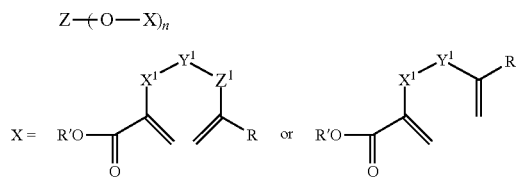

In the formula, Rs each represent a hydrogen atom or a methyl group. $X^1$, $Y^1$, $Z^1$, $X^2$, and $Y^2$ are the same as or different from one another, and each represent a methylene group, a methylene group in which a hydrogen atom is replaced by a methyl group, an oxygen atom, a sulfur atom, or an imino group. Here, at least one of $X^1$, $Y^1$, and $Z^1$ is an oxygen atom, a sulfur atom, or an imino group, and at least one of $X^2$ and $Y^2$ is an oxygen atom, a sulfur atom, or an imino group. Z represents an organic group with two or more valences, and n represents an integer of two or more.

In the present description and drawings, "or (in Japanese)" is also described as "or (in English)".

The total amount of the reactive diluent may be appropriately set according to the purpose and the application, under considering the viscosity, coatability, and curing characteristics of the polymerizable/curable composition, and physical properties of the resulting polymerized/cured product. Therefore, the total amount is not particularly limited, and is preferably 0 to 1,500 mass % based on 100 mass % of the diene carboxylate anion of the claimed invention or the salt thereof. The total amount is more preferably 0 to 1,000 mass %, and further preferably 0 to 800 mass %.

The reactive diluent is not an essential component of the polymerizable/curable composition. The total amount thereof may be 0 mass % because the reactive diluent is preferably not to be used depending on applications and curing conditions.

<Stabilizer>

A stabilizer is a compound that prevents radical polymerization and oxidative polymerization in order to improve handleability and storage stability. One or more of general polymerization inhibitor(s) or general antioxidant(s) may be used, and no particular limitation is imposed.

Examples of the stabilizer include compounds such as phenol compounds, copper salts of organic acids, phenothiazines, phosphites, phosphines, thioethers, hindered amine compounds, ascorbic acid compounds, thiocyanates, thiourea derivatives, nitrites, sulfites, thiosulfates, and hydroxylamine derivatives. Preferable among these are phenol compounds in terms of pigmentation and compatibility. Specific examples include hydroquinone, methyl hydroquinone, trimethyl hydroquinone, t-butyl hydroquinone, p-methoxy phenol, 6-t-butyl-2,4-xylenol, 2,6-di-t-butylphenol, 2,6-di-t-butyl-4-methoxyphenol, and 2,2'-methylene bis (4-methyl-6-t-butylphenol). Combination use of a phenol compound and a so-called secondary antioxidant represented by phosphites and thioethers is more preferable because thereby anti-polymerization effect and anti-pigmentation effect are enhanced.

The total amount of the stabilizer may be appropriately set according to the purpose and the application and no particular limitation is imposed. Preferably, the total amount is 0.001 to 20 mass % based on 100 mass % of the diene carboxylate anion of the claimed invention or the salt thereof in terms of factors such as curability and a balance of economic efficiency. The total amount is more preferably 0.05 to 10 mass %, and further preferably 0.01 to 5 mass %. The total amount of the stabilizer may be 0 mass % because the diene carboxylate anion of the claimed invention or the salt thereof may be stable enough depending on the kind of the metal and the storage conditions, and depending on the structure of the anion or the salt and the use conditions.

<Binder Resin>

A binder resin is an oligomer or a polymer that provides/improves the film-forming ability of the composition and prevents deformation, just like a filler. A binder resin further provides various properties such as alkaline developability, dispersibility of color materials, and heat resistance, according to purposes and applications. One or more of binder resin (s) may be selected from various kinds of oligomers and polymers generally used as binder resins, and no particular limitation is imposed.

For example, if the binder resin is an alkali-soluble oligomer or polymer, such as a carboxyl group-added vinyl ester resin or a (meth)acrylate copolymer, the polymerizable/curable composition of the claimed invention can be used for applications for alkaline-developable resist such as solder resist, resist for color filters, and resist for protective film layer. The metal salt of a diene carboxylic acid of the claimed invention itself may have water solubility, alkali solubility, and solubility in acidic water and have some extent of film-forming ability, depending on the kind of the metal. Therefore, such a metal salt can be used as negative resist which is developable with various developing solutions even in the presence of no or a slight amount of a binder resin. Also, if the binder resin is a polymer such as a (meth)acrylic ester polymer, having a proper glass-transition temperature and compatibility with color materials and dispersants, the polymerizable/curable composition of the claimed invention can be used for paints and inks.

The total amount of the binder resin may be appropriately set under considering the above properties according to the purpose and the application, and no particular limitation is imposed. The total amount is preferably 0 to 1,000 mass % based on 100 mass % of the diene carboxylate anion of the claimed invention or the salt thereof. The total amount is more preferably 0 to 800 mass %, and further preferably 0 to 500 mass %.

The binder resin is not an essential component of the polymerizable/curable composition. The total amount thereof may be 0 mass % because binder resins are preferably not to be used depending on applications and curing conditions.

<Method for Polymerizing/Curing the Diene Carboxylate Anion of the Claimed Invention, the Salt Thereof, and the Composition Containing the Anion or the Salt>

Another aspect of the claimed invention is a method for polymerizing/curing the diene carboxylate anion, the salt thereof, or the polymerizable/curable composition containing the diene carboxylate anion or the salt thereof. As mentioned above, the diene carboxylate anion of the claimed invention, the salt thereof, or the polymerizable/curable composition can be polymerized by two polymerization mechanisms: radical polymerization mechanism and oxidative polymerization mechanism. These mechanisms can be triggered by three curing methods, which are heating, iraddiating with active energy beams, and exposing to an atmosphere including oxygen. Only one of these may be employed, or two or more of these may be employed in combination.

Specifically, another aspect of the claimed invention is a method for polymerizing/curing a diene carboxylate anion, a salt thereof, or a polymerizable/curable composition containing the diene carboxylate anion or the salt thereof, including at least one step selected from the group consisting of heating, iraddiating with active energy beams, and exposing to an atmosphere including oxygen.

Heating conditions, that is, the polymerization/curing temperature in the polymerization/curing method by heating may be appropriately selected according to the kind of the diene carboxylate anion or the salt thereof and the combination of the polymerizable/curable compositions. In the case that a curing accelerator is not used, the temperature is preferably 30 to 400° C., more preferably 70 to 350° C., and still more preferably 100 to 350° C. Curing at such a temperature enables easy curing without a curing accelerator and prevention of pyrolysis caused by excessive heating.

In the case that a curing accelerator is used, curing is possible at lower temperatures than in the case of not using a curing accelerator, and the temperature is preferably 0 to 400° C., more preferably 10 to 350° C., and still more preferably 20 to 350° C.

Curing by heating may be carried out in one stage or in two or more stages, and may be carried out before or after the curing by iraddiating with active energy beams and/or exposing to an atmosphere including oxygen. Preferable is, for example, curing by a process called post-bake process or post curing process, in which an required treatment like development is carried out after the composition is first crosslinked to some extent by heating at a low temperature or by active energy irradiation for a short time, and then the composition is cured at a high temperature, preferably 150° C. or higher, more preferably 180° C., and still more preferably 200° C. or higher. Thereby, the crosslinking reaction proceeds further.

The active energy beams used in the polymerization/curing method by iraddiating with active energy beams may be general beams. Examples thereof include electromagnetic waves such as gamma rays, X-rays, ultraviolet rays, visible rays, and infrared rays; and corpuscular beams such as electron beams, neutron beams, and proton beams. Preferable among these are gamma rays, X-rays, ultraviolet rays, visible rays, and electron beams, more preferably ultraviolet rays, visible rays, and electron beams, and most preferably ultraviolet rays, in terms of the intensity of the energy, factors relating to an energy beam generator, and the like. In the case of not using a curing accelerator, active energy beams having a high energy, such as gamma rays, X-rays, and electron beams, are preferred. Whereas, in the case of using a curing accelerator, active energy beams such as ultraviolet rays and visible rays, which have a relatively low energy but can be easily and economically generated, can be preferably used.

The curing method by exposing to an atmosphere including oxygen means a polymerization/curing method in which the diene carboxylate anion of the claimed invention, the salt thereof, or the polymerizable/curable composition containing the anion or the salt is exposed to an atmosphere including oxygen. The concentration of the oxygen in the atmosphere is preferably 5% by volume or more, more preferably 10% by volume or more, and most preferably 18% by volume or more. In other words, a concentration similar to or higher than the oxygen concentration in the air is most preferable.

This method may be used in combination with the polymerization/curing method by heating and/or by iraddiating with active energy beams. Particularly preferred is performing the polymerization/curing method by heating and/or by iraddiating with active energy beams in the air, because it is an easy way for the combination use.

<Polymerized/Cured Product of the Diene Carboxylate Anion of the Claimed Invention, the Salt Thereof, or the Composition Containing the Anion or the Salt>

Another aspect of the claimed invention is a polymerized/cured product produced by polymerizing/curing the diene carboxylate anion, the salt thereof, or the polymerizable/curable composition containing the diene carboxylate anion or the salt thereof, according to the above mentioned polymerization/curing method. The polymerized/cured product of the claimed invention contains many ionic bonds. Particularly, if the salt of a diene carboxylic acid is a metal salt, the polymerized/cured product also contains a metal. Accordingly, the polymerized/cured product provides various properties according to these ionic bonds and/or a metal. Examples of the properties include hardness, scratch resistance, anti-fingerprint property, gas-barrier property, water vapor barrier property, oxygen absorption property, ultraviolet protection, infrared protection, color development and coloring, high refractive index, adhesion, various catalytic abilities, fluorescence ability and light-emitting ability, optical amplification, dispersibility, and antistatic properties. Therefore, the polymerized/cured product may be used in various applications using these properties. In addition, the polymerized/cured product may be used as a raw material for functional fine particles and composite materials including nanoparticles, and in addition, may be appropriately used as a MOD material.

Advantageous Effects of Invention

The claimed invention provides a diene carboxylate anion or a salt thereof, that is easily dissolved in various general solvents such as organic solvents, reactive diluents, and resins, can be in a liquid state at normal temperature depending on the structure, and has a high polymerizability; a polymerizable/curable composition containing the anion or the salt; and a method for polymerizing/curing the anion, the salt, and the polymerizable/curable composition. The claimed invention also provides a polymerized/cured product by the polymerization/curing method. The polymerized/cured product contains ionic bonds, and also a metal in some cases, and thereby provides various properties (e.g. hardness, scratch resistance, anti-fingerprint property, gas-barrier property, water vapor barrier property, oxygen absorption property, ultraviolet protection, infrared protection, color development and coloring, high refractive index, adhesion, various catalytic abilities, fluorescence ability and light-emitting ability, optical amplification, dispersibility, and antistatic properties) according to the ionic bonds and/or the metal. Accordingly, the diene carboxylate anion of the claimed invention or the salt thereof, the polymerizable/curable composition, and the polymerized/cured product can be widely applied in various fields such as fields of information technology (IT), automobiles, architecture, medical treatment, and commodities. Examples of the applications include coating materials, ionomer resins, adhesives, sealing materials, tackifiers, paints, pigment dispersion, reactive emulsifiers, reactive surfactants, dispersion of fine particles of metals or metal oxides, inks, resists, MOD materials, molding materials, gas barrier materials, water vapor barrier materials, oxygen absorption materials, lenses, dental materials, antimicrobial agents, rubbers, tires, lightings, solar cells, wiring materials, electrode materials, undercoat for plating, optical fibers, optical waveguides, superconducting materials, semiconductor chips, magnetic materials, memories, capacitors, and piezoelectrics.

BRIEF DESCRIPTION OF DRAWINGS

FIG. 3(i) shows a schematic diagram of the cyclic polymerization mechanism of a diene carboxylate anion represented by Formula (1).

FIG. 7-1 shows the result of $^1$H-NMR measurement of Me-AMA obtained in Synthesis Example 1.

FIG. 7-2 shows the result of IR measurement of Me-AMA obtained in Synthesis Example 1.

FIG. 8-1 shows the result of $^1$H-NMR measurement of Me-MAMA obtained in Synthesis Example 2.

FIG. 8-2 shows the result of IR measurement of Me-MAMA obtained in Synthesis Example 2.

FIG. 10-1 shows the result of $^1$H-NMR measurement of H-AMA obtained in Example 1-1.

FIG. 10-2 shows the result of IR measurement of H-AMA obtained in Example 1-1.

FIG. 11-1 shows the result of $^1$H-NMR measurement of H-MAMA obtained in Example 1-2.

FIG. 11-2 shows the result of IR measurement of H-MAMA obtained in Example 1-2.

FIG. 12-1 shows the result of $^1$H-NMR measurement of $Zn(AMA)_2$ obtained in Example 1-4.

FIG. 12-2 shows the result of IR measurement of $Zn(ANA)_2$ obtained in Example 1-4.

FIG. 13-1 shows the result of $^1$H-NMR measurement of $Zn(MAMA)_2$ obtained in Example 1-5.

FIG. 13-2 shows the result of IR measurement of $Zn(MAMA)_2$ obtained in Example 1-5.

FIG. 14-1 shows the result of $^1$H-NMR measurement of $(C_2H_5)_3NH(AMA)$ obtained in Example 1-6.

FIG. 14-2 shows the result of IR measurement of $(C_2H_5)_3NE(AMA)$ obtained in Example 1-6.

FIG. 15-1 shows the result of $^1$H-NMR measurement of $(CH_3)_2Sn(AMA)_2$ obtained in Example 1-9.

FIG. 15-2 shows the result of IR measurement of $(CH_3)_2Sn(AMA)_2$ obtained in Example 1-9.

FIG. 16-1 shows the result of $^1$H-NMR measurement of $In(AMA)_2(MAA)_1$ obtained in Example 1-13.

FIG. 16-2 shows the result of IR measurement of $In(AMA)_2(MAA)_1$ obtained in Example 1-13.

FIG. 17-1 shows the result of $^1$H-NMR measurement of $ZrO(AMA)_2$ obtained in Example 1-14.

FIG. 17-2 shows the result of IR measurement of $ZrO(AMA)_2$ obtained in Example 1-14.

FIG. 18-1 shows the result of $^1$H-NMR measurement of $(n-C_3H_7O)_2Zr(AMA)_2$ obtained in Example 1-15.

FIG. 18-2 shows the result of IR measurement of $(n-C_3H_7O)_2Zr(AMA)_2$ obtained in Example 1-15.

FIG. 19-1 shows the result of $^1$H-NMR measurement of Ag(AMA) obtained in Example 1-23.

FIG. 19-2 is the result of IR measurement of Ag(AMA) obtained in Example 1-23.

FIG. 20-1 shows a graph of the measurement of the light transmittance in Example 9-1.

FIG. 20-2 shows a graph of the measurement of the light transmittance in Example 9-2.

FIG. 20-3 shows a graph of the measurement of the light transmittance in Example 9-3.

FIG. 20-4 shows a graph of the measurement of the light transmittance in Comparative Example 9-1.

FIG. 21-1 shows a graph of the measurement of the light transmittance in Example 9-4.

FIG. 21-2 shows a graph of the measurement of the light transmittance in Example 9-5.

FIG. 21-3 shows a graph of the measurement of the light transmittance in Example 9-6.

FIG. 21-4 shows a graph of the measurement of the light transmittance in Example 9-7.

DESCRIPTION OF EMBODIMENTS

The following describes the details of the claimed invention with reference to the examples. The claimed invention is, however, not limited to these examples. Here, "part" means "part by weight", and "%" means "mass %", unless otherwise stated.

<Synthesis/Analysis of Each Compound>

The following describes synthesis and analysis of an ester of α-(meth)allyloxymethyl acrylic acid, α-(meth)allyloxymethyl acrylic acid, and a salt of α-(meth)allyloxymethyl acrylic acid.

The devices and conditions used in the analysis are shown below.

[HPLC Analysis]

The analysis was performed using the high performance liquid chromatography (HPLC) device and the conditions shown below.

The device and the conditions enables to detect an ester of α-(meth)allyloxymethyl acrylic acid and α-(meth)allyloxymethyl acrylic acid. The α-(meth)allyloxymethylacrylate anions are detected in a state of α-(meth)allyloxymethyl acrylic acid by the action of the phosphoric acid in an elution solvent.

HPLC device: Combination of DGU-20A5, LC-20AD, SIL-20A, SPD-20A, and CTO-20A (all are produced by Shimadzu Corporation)

Dilution solvent: Acetonitrile/methanol=2/1 (by mass)

Elution solvent: A mixed solvent of 0.1 mol % phosphoric acid aqueous solution/acetonitrile/methanol Separation column: CAPCELL PACK C18, TYPE AQ (produced by Shiseido Co., Ltd.)

[$^1$H-NMR Spectrum Measurement]

A nuclear magnetic resonance apparatus (400 MHz/produced by Varian Inc.) was used.

[IR Transmission Spectrum Measurement]

An infrared spectrometer (Name: NEXUS-670, produced by Thermo Nicolet Corporation) was used.

[ICP Atomic Emission Spectrometry]

ICP spectrometer (Name: CIROS120, produced by SPECTRO) was used.

[Fluorescent X-ray Analysis]

Fluorescent X-ray analysis equipment (Type: PW-2404, produced by Royal Philips Electronics) was used.

Synthesis Example 1

Synthesis of methyl α-allyloxy methyl acrylate (Me-AMA)

Figure 1:
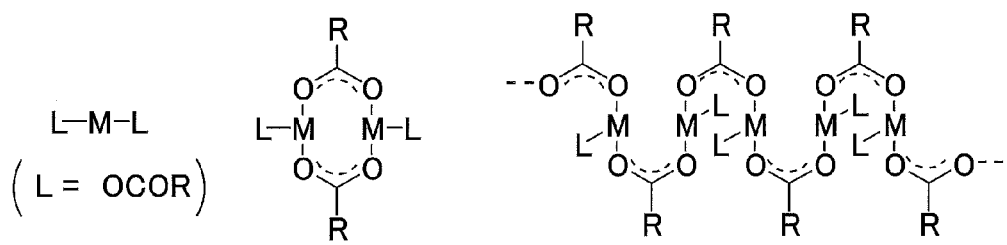
FIG. 1 shows an example of possible coordinate structures of a salt represented by the chemical formula $(RCOO)_2M$.
Figure 2:
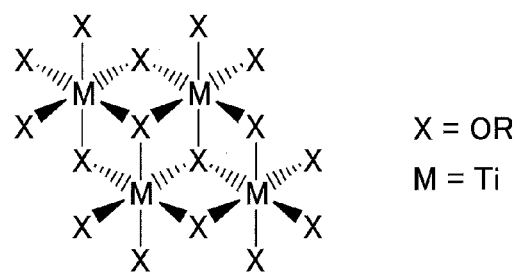
FIG. 2 shows a possible tetrameric structure of a titanium tetra-alkoxide.
Figures 1, 7:
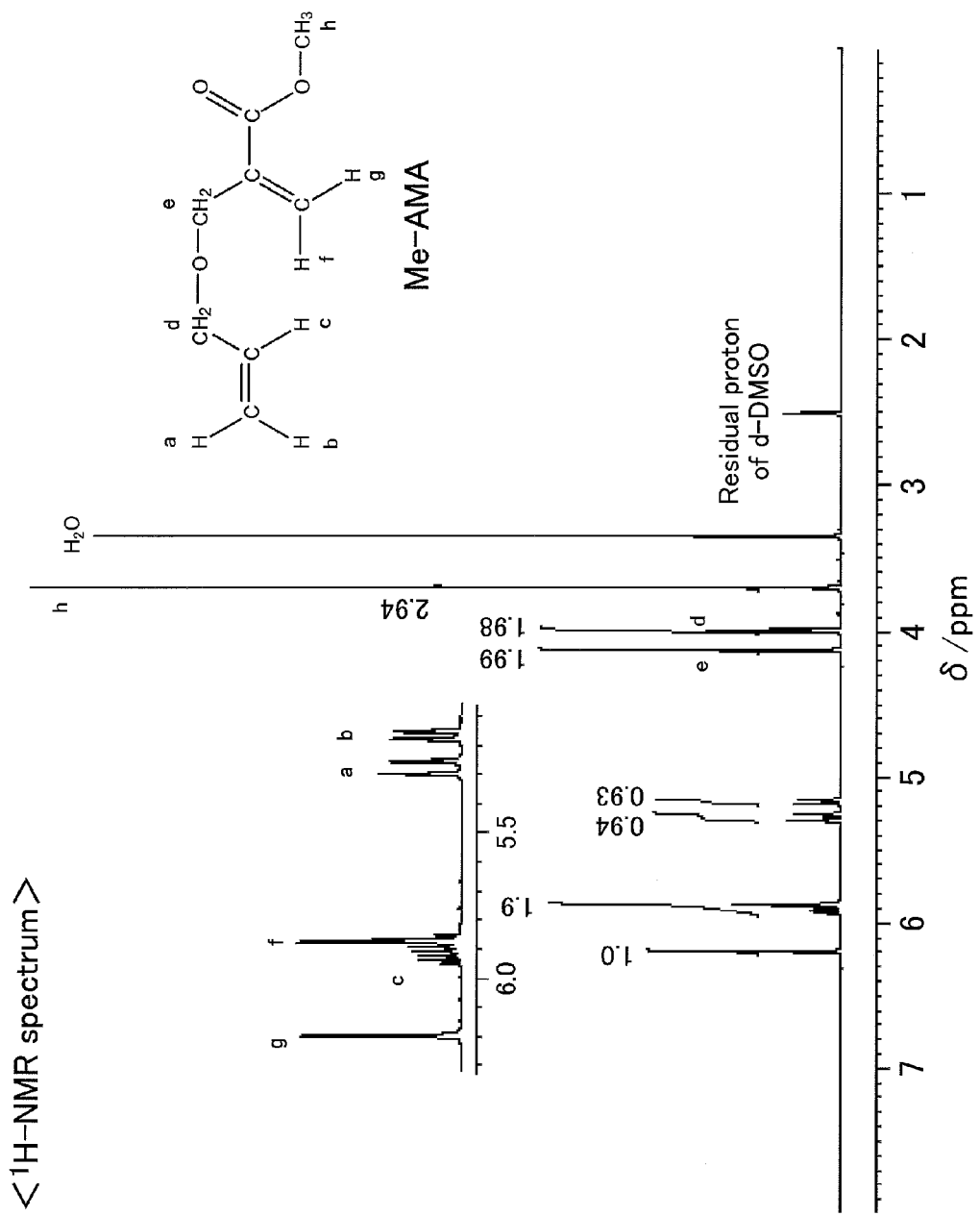
Figures 2, 7:
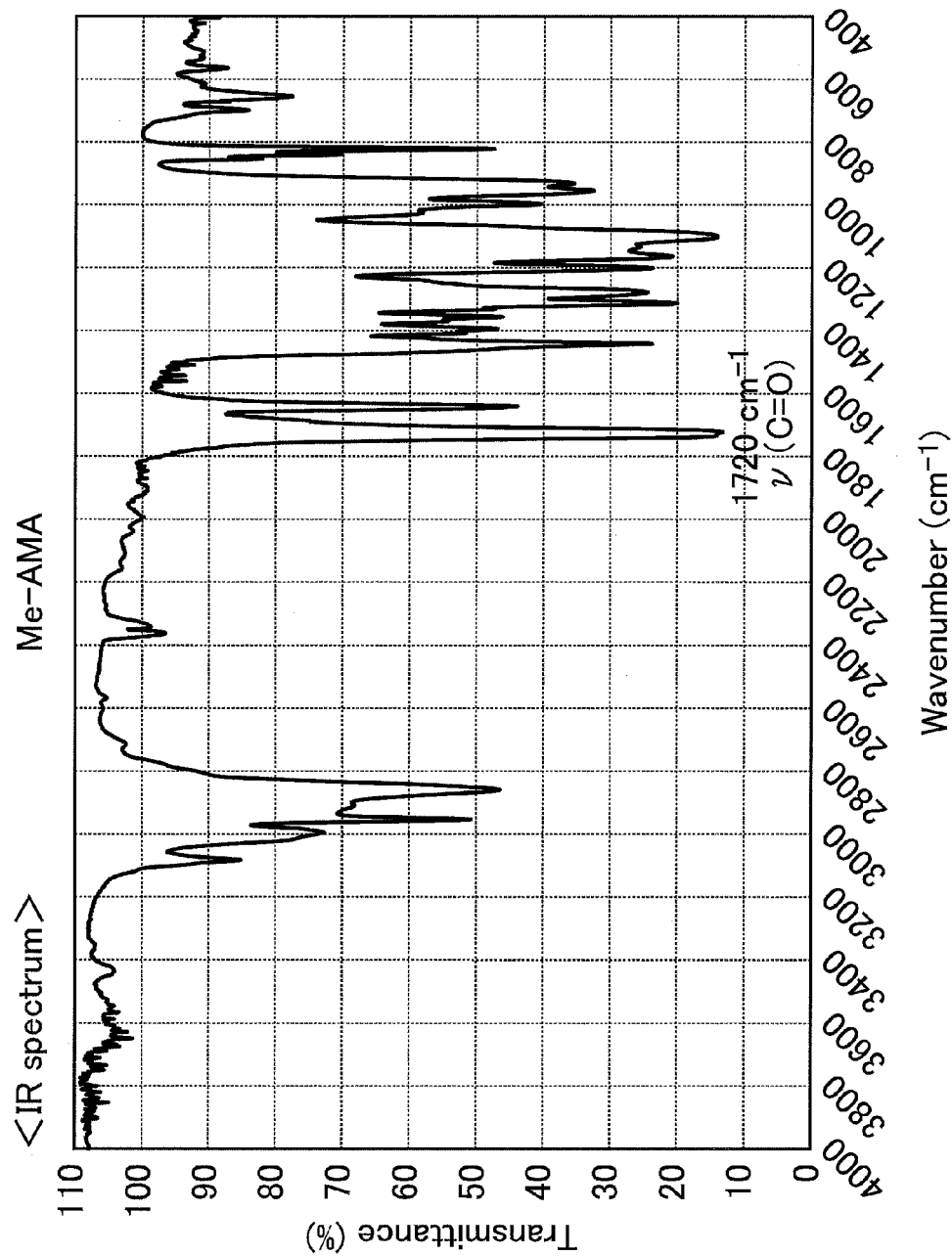

The synthesis was carried out with methyl α-hydroxymethyl acrylate and allyl alcohol in the presence of 1,4-diazabicyclo[2.2.2]octane as a catalyst based on JP 10-226669 A. The obtained colorless transparent liquid was dissolved in deuterated dimethyl sulfoxide (d-DMSO) and the $^1$H-NMR spectrum of the liquid was measured. FIG. 7-1 shows the obtained NMR spectrum and the assignment of the peaks. Also, the IR transmission spectrum of the liquid was measured by liquid membrane technique using a potassium bromide (KBr) plate. The result showed no absorption band assigned to a carboxylate anion but showed an absorption band assigned to the C=O stretching vibration of a carboxylic acid or a carboxylic ester. The wavenumber (hereinafter, referred to as ν(C=O)) at which the absorption shows the maximum value within the absorption band was 1720 cm$^{-1}$. FIG. 7-2 shows the obtained IR spectrum and the assignment of the peak.

Synthesis Example 2

Synthesis of methyl α-methallyl oxymethyl acrylate (Me-MAMA)

Figures 1, 8:
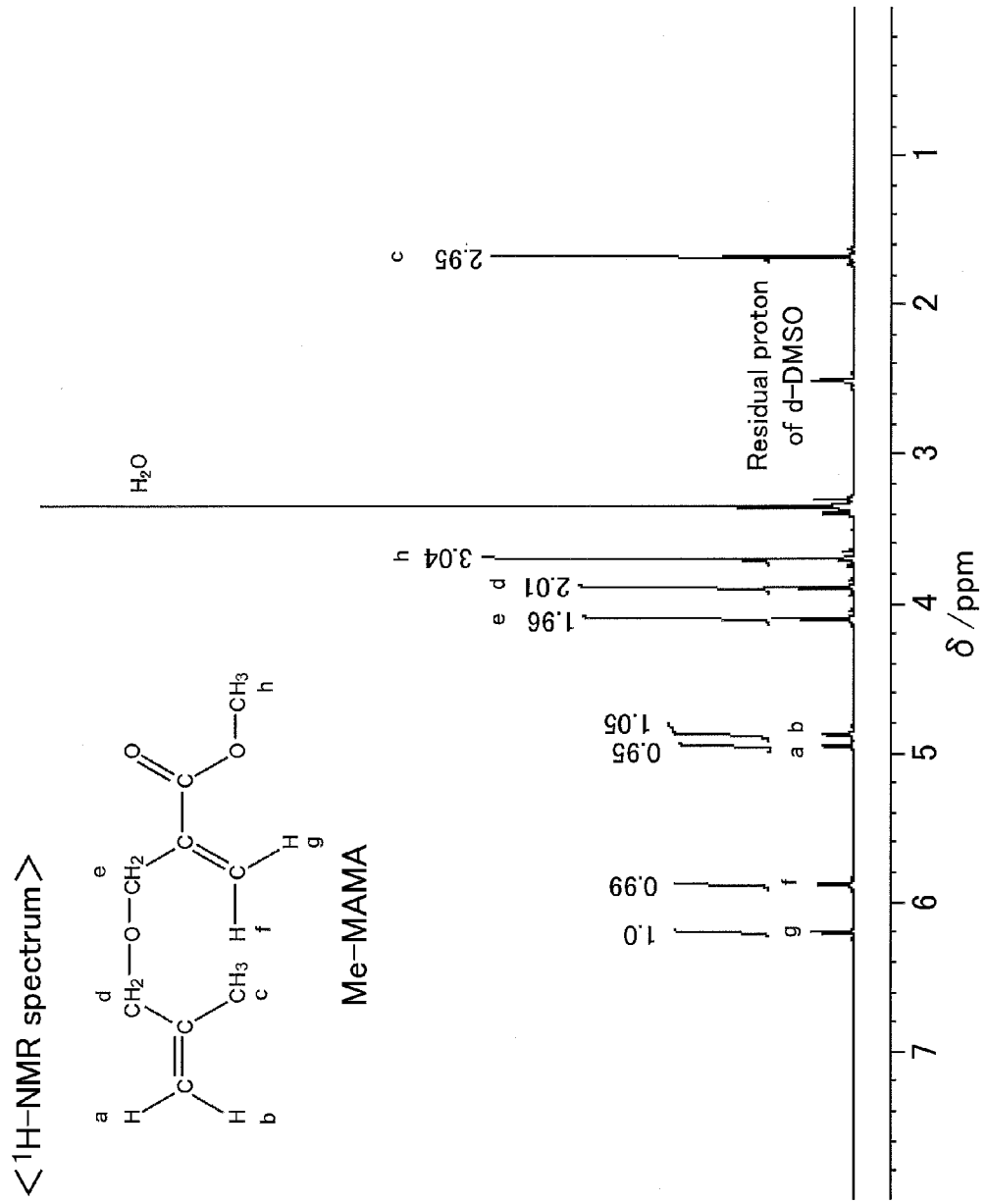
Figures 2, 8:
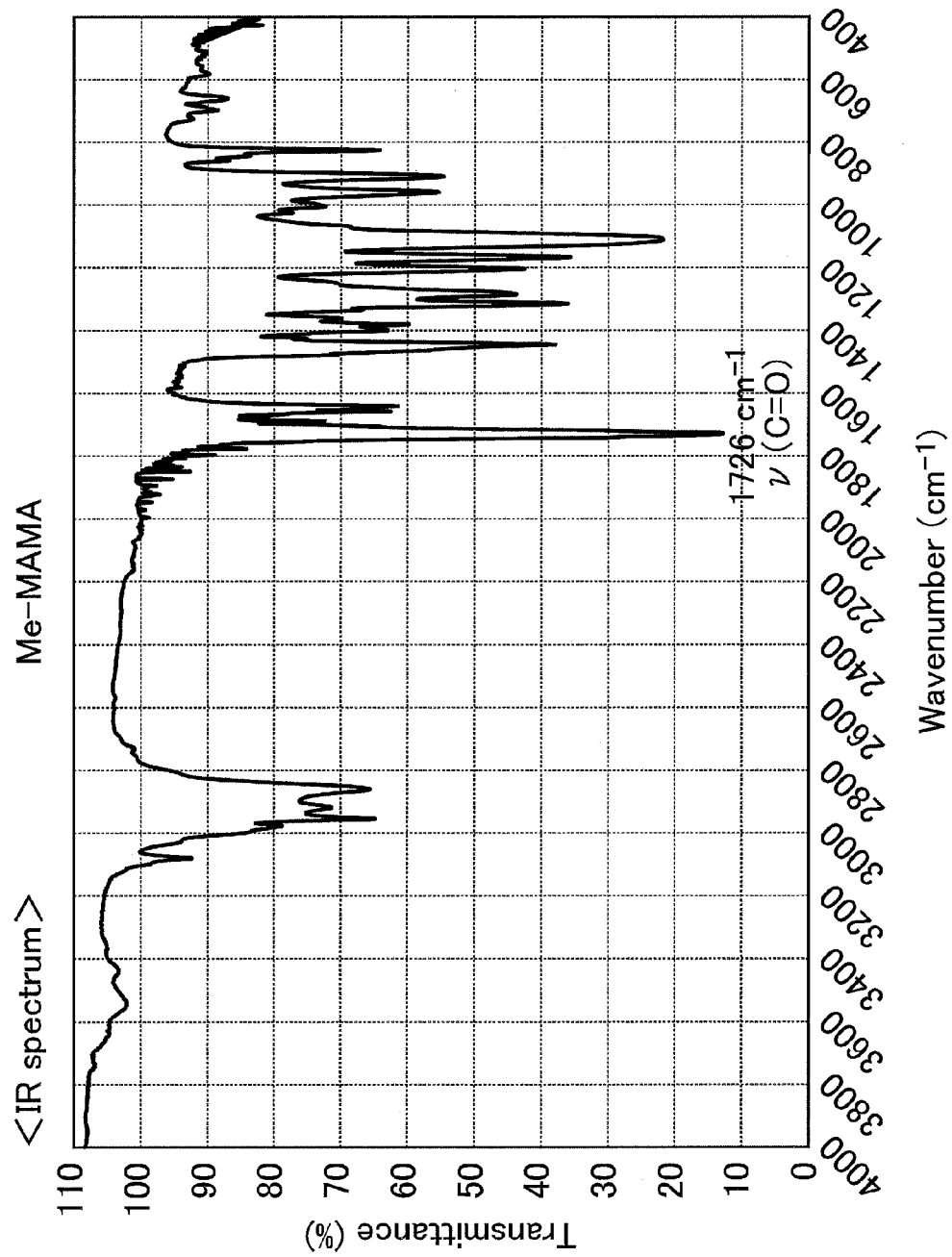

The synthesis was carried out with methyl α-hydroxymethyl acrylate and methallyl alcohol in the same manner as in Synthesis Example 1. $^1$H-NMR and IR spectra of the obtained colorless transparent liquid were measured in the same manner as in Synthesis Example 1. FIGS. 8-1 and 8-2 show the NMR and IR spectra with the assignment of the peaks. The value of ν(C=O) was 1726 cm$^{-1}$.

Synthesis Example 3

Synthesis of the Compound Represented by the Following Formulas (neopentyl glycol di(α-allyloxymethyl acrylate) (NPG-AMA)

The synthesis was carried out in accordance with JP 2011-74068 A.

[Chem. 9]

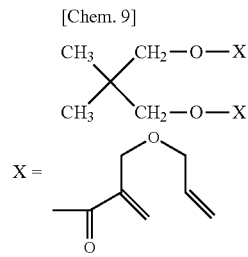

Synthesis Example 4

Synthesis of the Compound Represented by the Following Formulas (diethylene glycol di(α-allyloxymethyl acrylate) (DEG-AMA)

The synthesis was carried out in accordance with JP 2011-74068 A.

[Chem. 10]

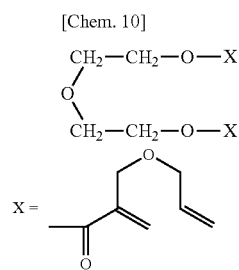

Synthesis Example 5

Synthesis of the Compound Represented by the Following Formulas (trimethylol propane tri(α-allyloxymethyl acrylate) (TMP-AMA)

The synthesis was carried out in accordance with JP 2011-74068 A.

[Chem. 11]

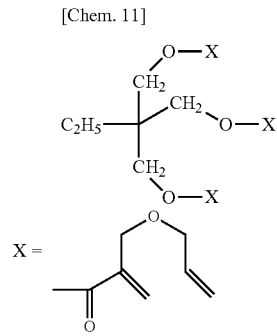

Example 1-1

Synthesis of an Aqueous Solution of a Salt (Na (AMA)) of α-allyloxymethylacrylate anion (AMA$^-$) and sodium ion (Na$^+$), and α-allyloxymethyl acrylic acid (H-AMA)

A reaction vessel containing a stirrer was charged with a 10% sodium hydroxide (NaGH) aqueous solution (100.0 parts) and Me-AMA (37.2 parts), and the mixture was stirred with a magnetic stirrer while cooled in a water bath. The stirring was continued until Me-AMA disappeared, and thereby a Na(AMA) aqueous solution that was an electrolyte containing ionized AMA⁻ and ionized Na⁺ was obtained. The disappearance of Me-AMA was confirmed by HPLC analysis.

Figure 9:
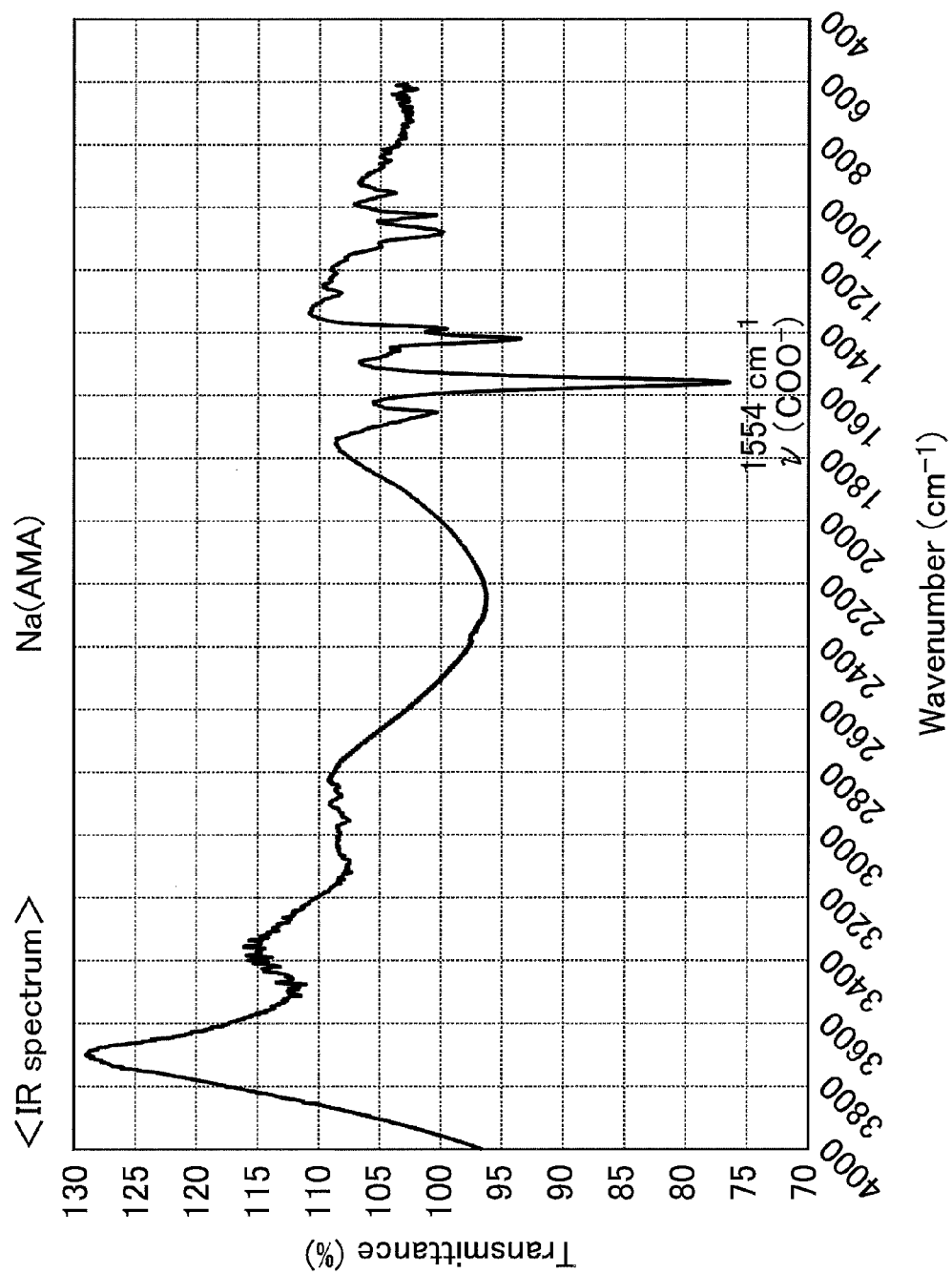
FIG. 9 shows the result of IR measurement of Na(AMA) aqueous solution obtained in Example 1-1.

A small amount of the aqueous solution was collected and was subjected to IR measurement by liquid membrane technique using a KBr plate, and subsequently the Na(AMA)/water difference spectrum was measured. The result showed absorption assigned to the antisymmetric stretching of a carboxylate anion, and the wavenumber (hereinafter, referred to as ν(COO⁻)) at which the absorption shows the maximum value within the absorption band was 1554 cm⁻¹. FIG. 9 shows the IR spectrum and the assignment of the peak, and Table 1 shows the value of ν(COO⁻).

Figures 1, 10:
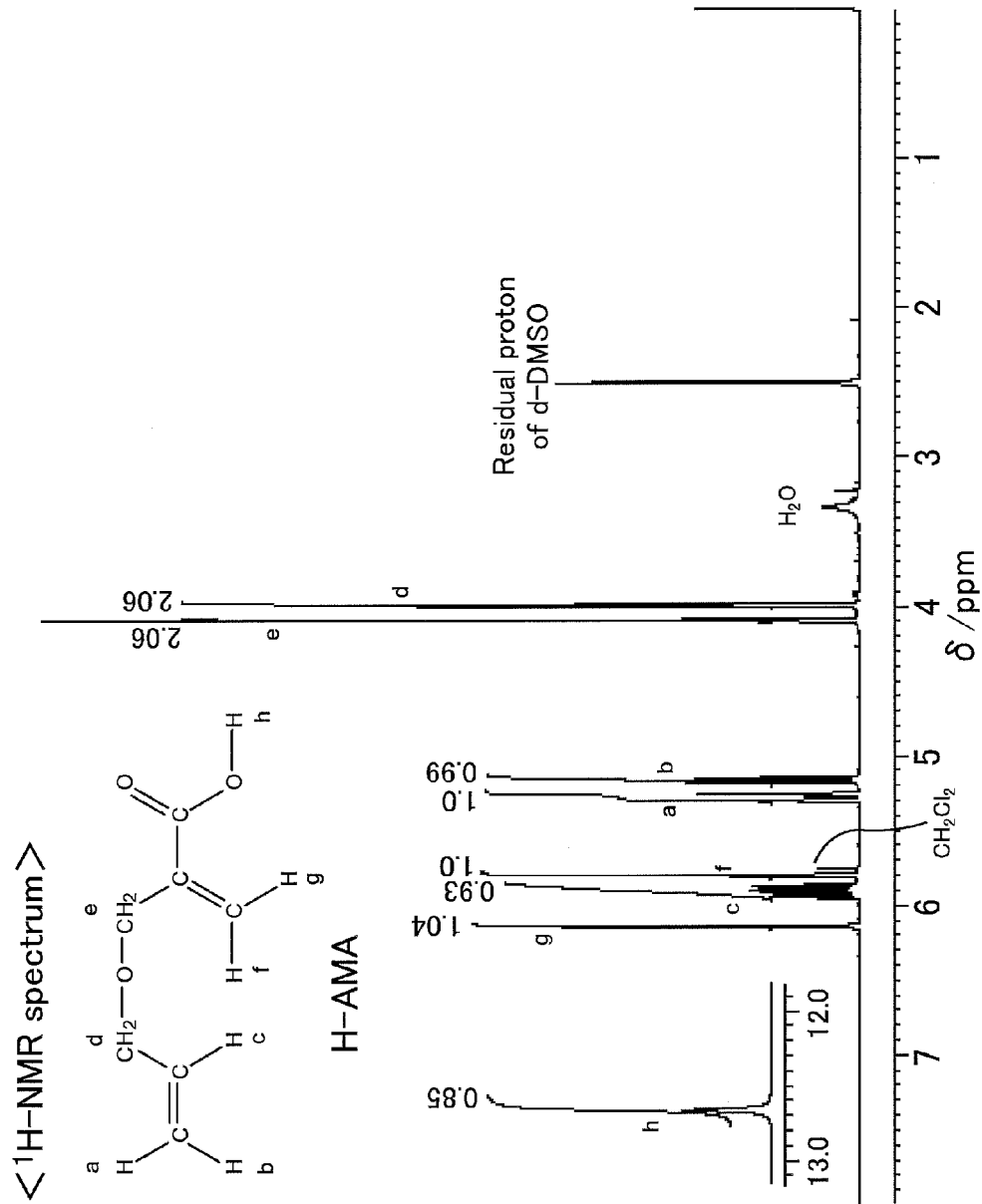
Figures 2, 10:
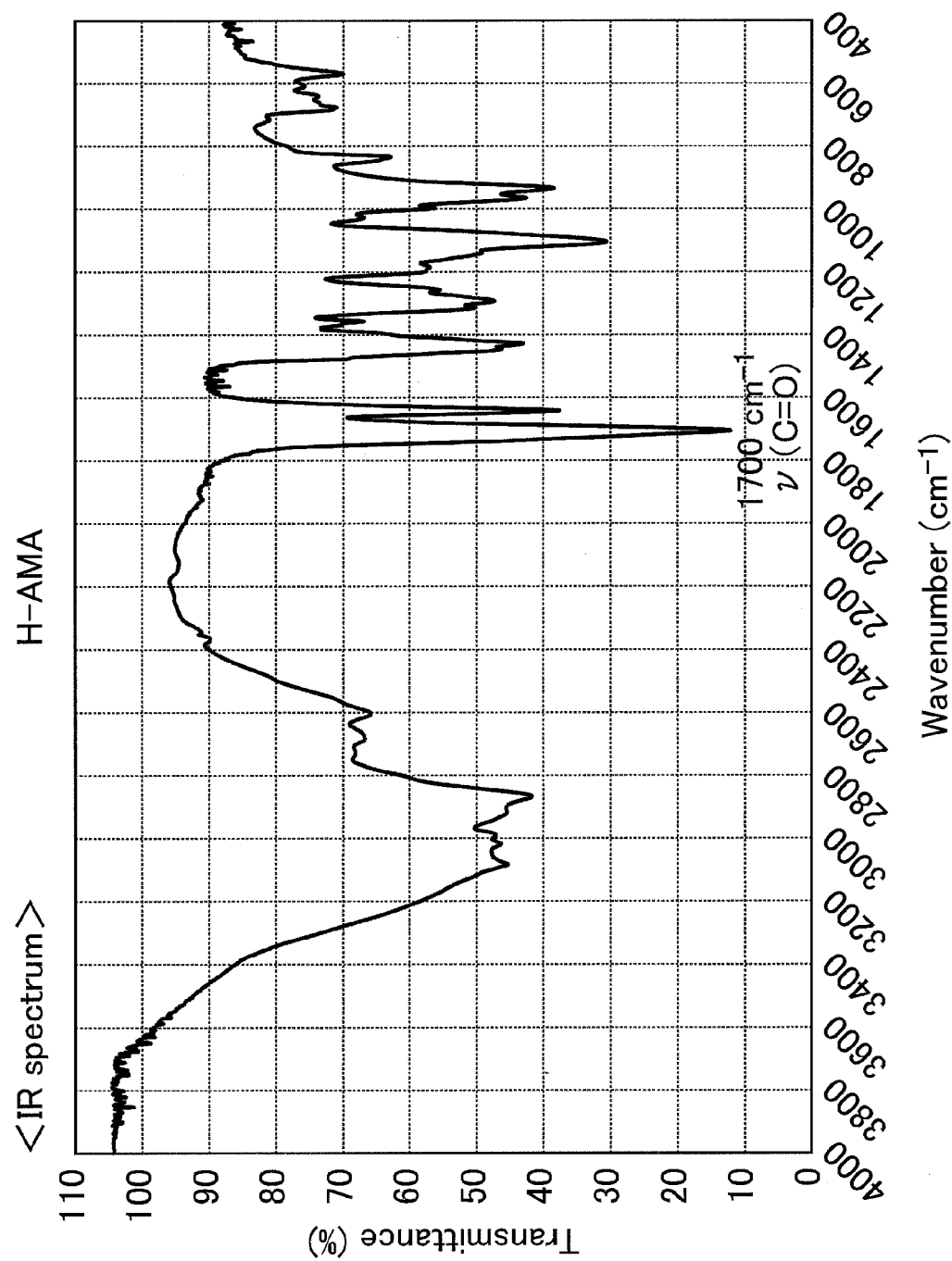

Next, to the Na(AMA) aqueous solution being stirred and cooled in a water bath was added dropwise a 15% sulfuric acid aqueous solution (116.8 parts). The stirring was continued for 30 minutes after the completion of the dropwise addition, and then the contents were transferred to a dropping funnel. The contents were extracted and separated with dichloromethane. Most of the dichloromethane was evaporated with an evaporator, and anhydrous magnesium sulfate was added to the obtained low-viscosity liquid. The mixture was stirred for one hour and then dehydrated. The anhydrous magnesium sulfate was removed by filtering, and the resulting product was further dried with a vacuum pump. Thereby, 30.1 parts of H-AMA was obtained in a state of a colorless transparent liquid. To the liquid were added 6-t-butyl-2,4-xylenol (hereinafter, abbreviated as TPA) and Adekastab 2112 (produced by Adeka Corporation, hereinafter abbreviated as AS2112) such that the concentrations thereof were 300 ppm and 1,000 ppm, respectively. The resulting mixture was dissolved in d-DMSO, and ¹H-NMR measurement was carried out. FIG. 10-1 shows the obtained spectrum and the assignment of the peaks. In addition, IR measurement was carried out by liquid membrane technique (KBr plate). The result showed no absorption band assigned to a carboxylate anion and ν(C=O) was observed at 1700 cm⁻¹. FIG. 10-2 shows the IR spectrum and the assignment of the peak.

Example 1-2

Synthesis of an aqueous solution of a salt (Na (MAMA)) of α-methallyloxymethylacrylate anion (MAMA⁻) and sodium ion (Na⁺), and α-methallyl oxymethyl acrylic acid (H-MAMA)

A reaction vessel containing a stirrer was charged with a 10% NaOH aqueous solution (10.0 parts) and Me-MAMA (4.1 parts), and the mixture was stirred with a magnetic stirrer while cooled in a water bath. The stirring was continued until Me-MAMA disappeared, and thereby a Na(MAMA) aqueous solution that was an electrolyte containing ionized MAMA⁻ and ionized Na⁺ was obtained. The disappearance of Me-MAMA was confirmed by HPLC analysis.

Figures 1, 11:
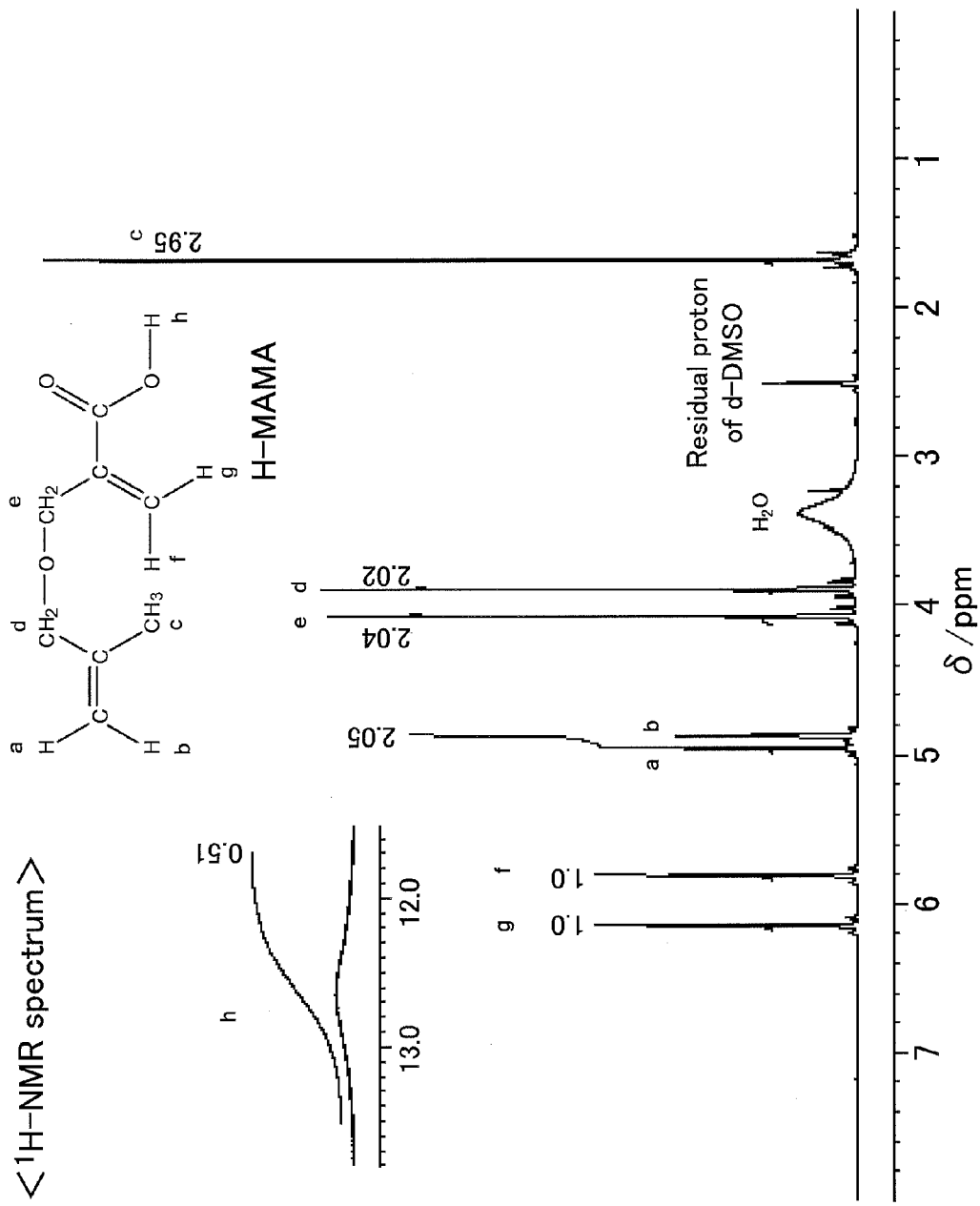
Figures 2, 11:
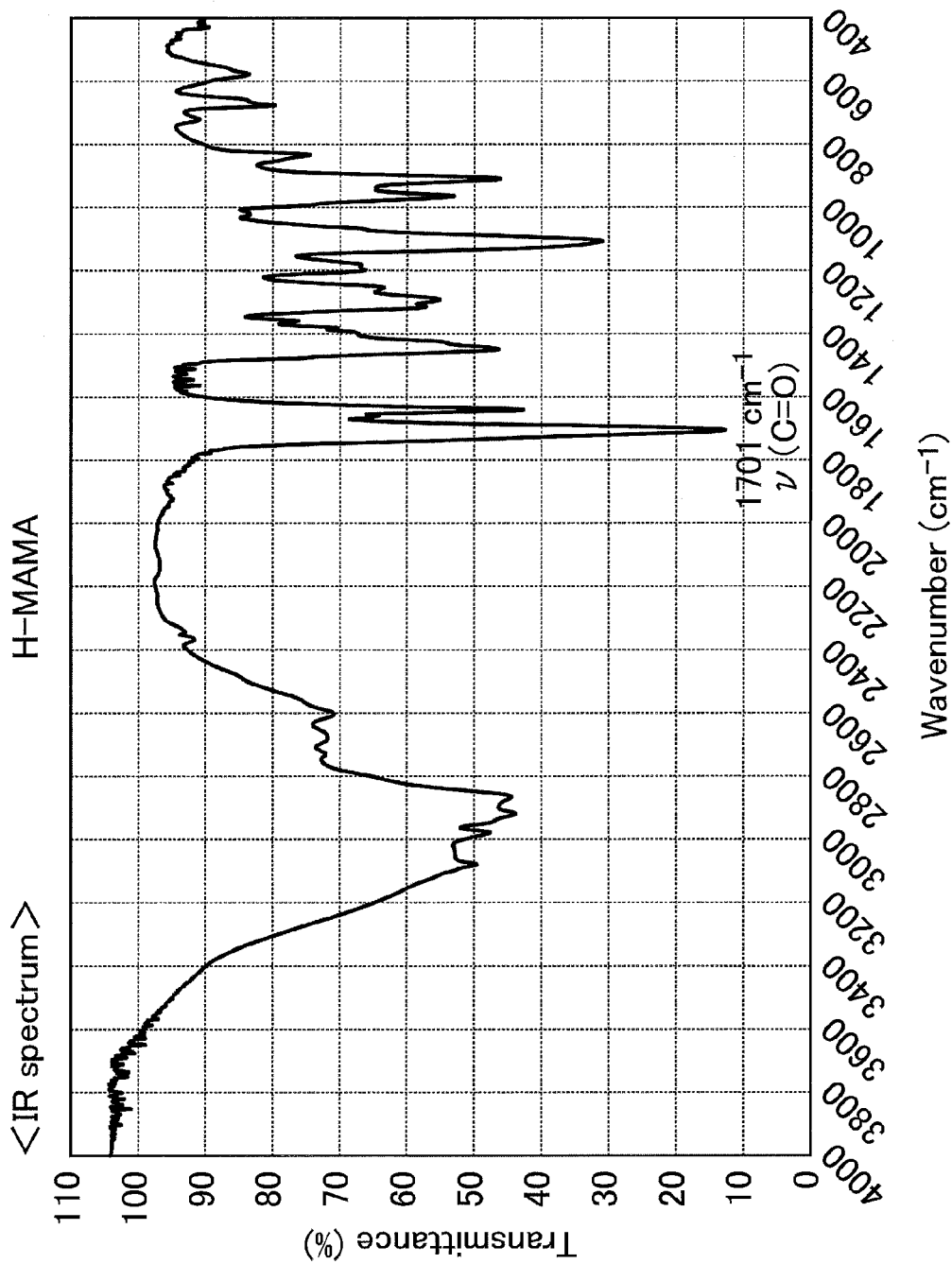

Next, to the Na (MAMA) aqueous solution being stirred and cooled in a water bath was added dropwise a 15% sulfuric acid aqueous solution (11.7 parts). The stirring was continued for 30 minutes after the completion of the dropwise addition, and then the contents were transferred to a dropping funnel. The contents were extracted and separated with dichloromethane. Most of the dichloromethane was evaporated with an evaporator, and anhydrous magnesium sulfate was added to the obtained low-viscosity liquid. The mixture was stirred for one hour and then dehydrated. The anhydrous magnesium sulfate was removed by filtering, and the resulting product was further dried with a vacuum pump. Thereby 3.2 parts of H-MAMA was obtained in a state of a colorless transparent liquid. To the obtained H-MAMA were added TPA and AS2112 such that the concentrations thereof were 300 ppm and 1,000 ppm, respectively. FIG. 11-1 shows the spectrum and the assignment of the peaks obtained by ¹H-NMR measurement (deuterated solvent: d-DMSO). In addition, IR measurement was carried out by liquid membrane technique (KBr plate). The result showed no absorption band assigned to a carboxylate anion, and ν(C=O) was observed at 1701 cm⁻¹. FIG. 11-2 shows the IR spectrum and the assignment of the peak.

Example 1-3

Synthesis of an aqueous solution of a salt (K(AMA)) of α-allyloxymethylacrylate anion (AMA⁻) and potassium ion (K⁺), and H-AMA A reaction vessel containing a stirrer was charged with a 10% potassium hydroxide aqueous solution (15.0 parts) and Me-AMA (4.0 parts), and the mixture was stirred with a magnetic stirrer while cooled in a water bath. The stirring was continued until Me-AMA disappeared, and thereby a K(AMA) aqueous solution that was an electrolyte containing ionized AMA⁻ and ionized K⁺ was obtained. The disappearance of Me-AMA was confirmed by HPLC analysis.

A small amount of the aqueous solution was collected and was subjected to IR measurement by liquid membrane technique using a KBr plate, and thereby the K(AMA)/water difference spectrum was measured. Then, ν(COO⁻) was observed at 1558 cm⁻¹.

Operations in the same manner as in Example 1-2, except for using a 15% sulfuric acid aqueous solution (12.5 parts), yielded 3.2 parts of a colorless transparent liquid. The spectra obtained by ¹H-NMR measurement and the IR spectra obtained by IR measurement corresponded to those of H-AMA obtained in Example 1-1.

Example 1-4

Synthesis of a salt (Zn(AMA)₂) of α-allyloxymethylacrylate anion (AMA⁻) and zinc ion (Zn²⁺)

A reaction vessel containing a stirrer was charged with a 10% sodium hydroxide aqueous solution (20.0 parts) and Me-AMA (7.4 parts), and the mixture was stirred with a magnetic stirrer while cooled in a water bath. The stirring was continued until Me-AMA disappeared (the disappearance was confirmed by HPLC analysis). To the resulting mixture was added toluene (30 ml), followed by addition of zinc sulfate heptahydrate (6.7 parts). Then, the mixture was stirred for one hour.

The contents were transferred to a dropping funnel, and were extracted and separated with toluene. To the toluene layer were added TPA (0.005 parts) and AS2112 (0.016 parts). The toluene was evaporated with an evaporator and the solution was concentrated. Thereby, a toluene solution (44.7 parts) of Zn(AMA)₂ was obtained in a state of a colorless transparent liquid.

Figures 1, 12:
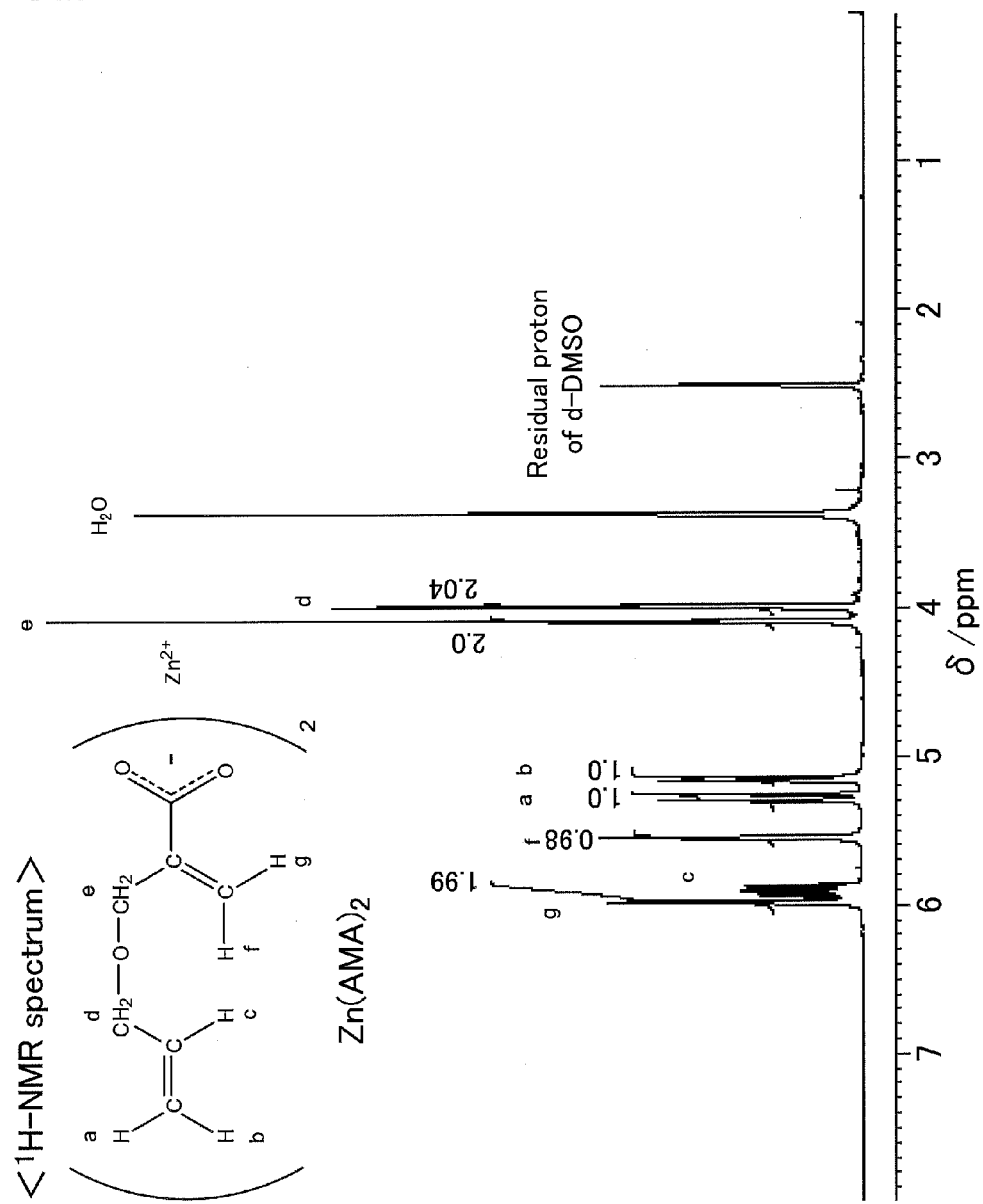
Figures 2, 12:
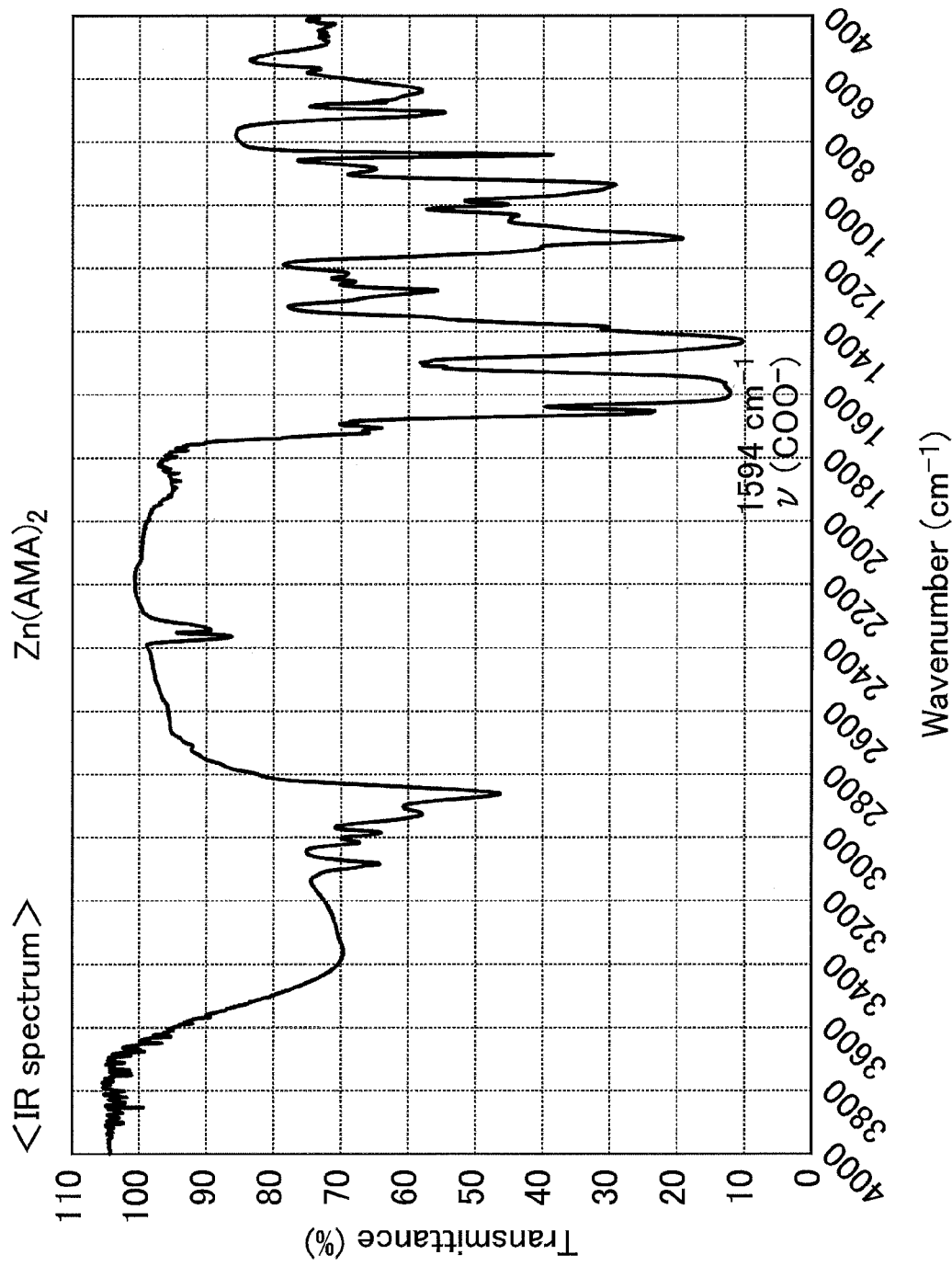

A small amount of the toluene solution was collected and dried with a vacuum pump. The resulting product was dissolved in d-DMSO and the resulting solution was measured by $^1$H-NMR. FIG. 12-1 shows the obtained spectrum and the assignment of the peaks. In addition, a small amount of the sample similarly dried with a vacuum pump was dissolved in dichloromethane. The resulting solution was applied to a KBr plate and the plate was left at room temperature to dry. The resulting plate was measured by IR. FIG. 12-2 shows the obtained spectrum and the assignment of the peaks, and Table 1 shows the value of $\nu(COO^-)$. In addition, the toluene solution was diluted with xylene. The resulting solution was analyzed by ICP atomic emission spectrometry and a strong peak assigned to zinc was observed.

Example 1-5

Synthesis of a salt (Zn (MAMA)$_2$) of α-methallyloxymethylacrylate anion (MAMA$^-$) and zinc ion (Zn$^{2+}$)

A reaction vessel containing a stirrer was charged with a 10% sodium hydroxide aqueous solution (5.0 parts) and Me-MAMA (2.0 parts), and the mixture was stirred with a magnetic stirrer while cooled in a water bath. The stirring was continued until Me-MAMA disappeared (the disappearance was confirmed by HPLC analysis). To the resulting mixture was added toluene (15 ml), followed by addition of zinc sulfate heptahydrate (1.7 parts), and the mixture was stirred for one hour.

The contents were transferred to a dropping funnel. The contents were extracted and separated with toluene. To the toluene layer were added TPA (0.001 parts) and AS2112 (0.004 parts). The toluene was evaporated with an evaporator and the solution was concentrated. Thereby, a toluene solution (10.4 parts) of Zn(MAMA)$_2$ was obtained in a state of a colorless transparent liquid.

Figures 1, 13:
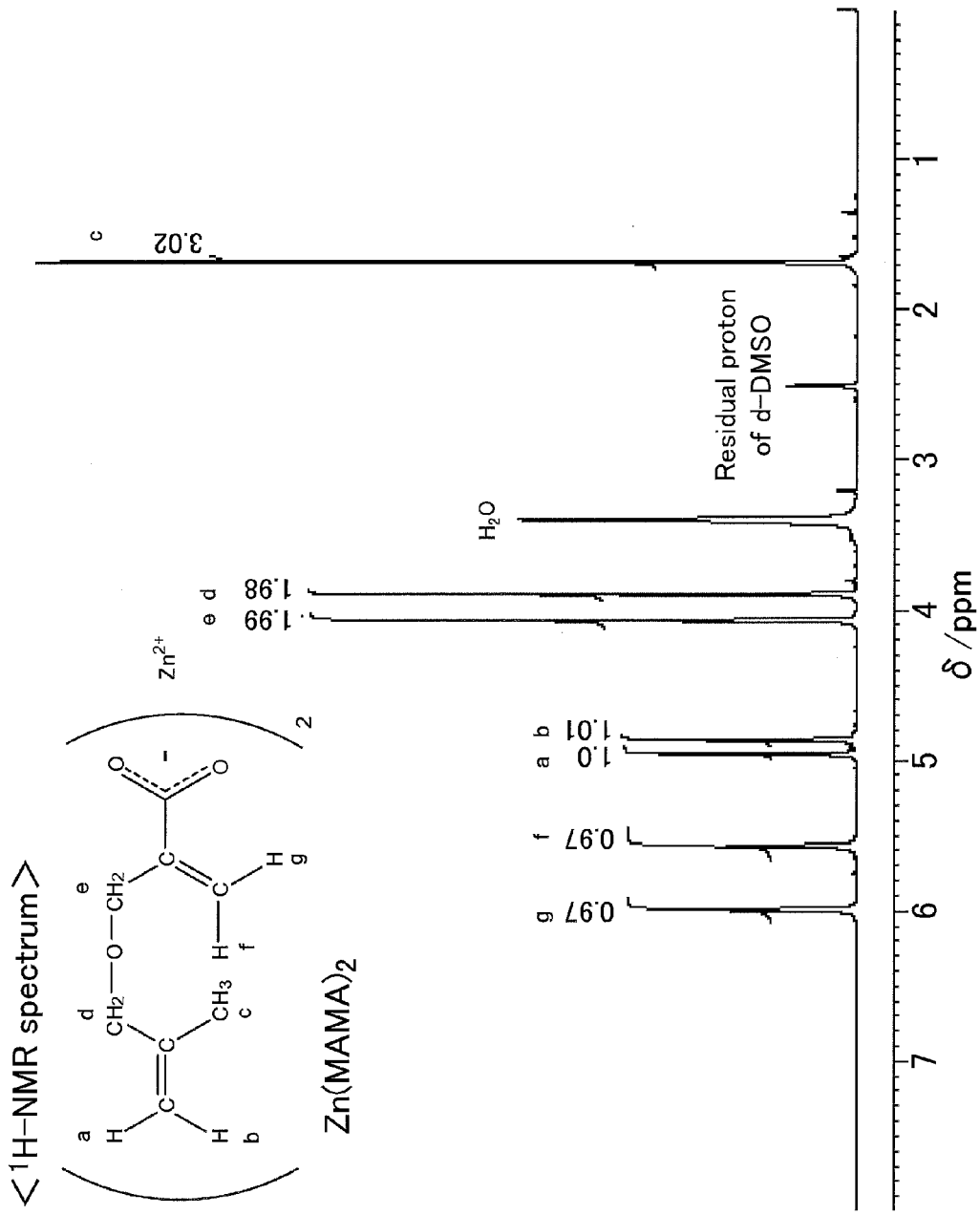
Figures 2, 13:
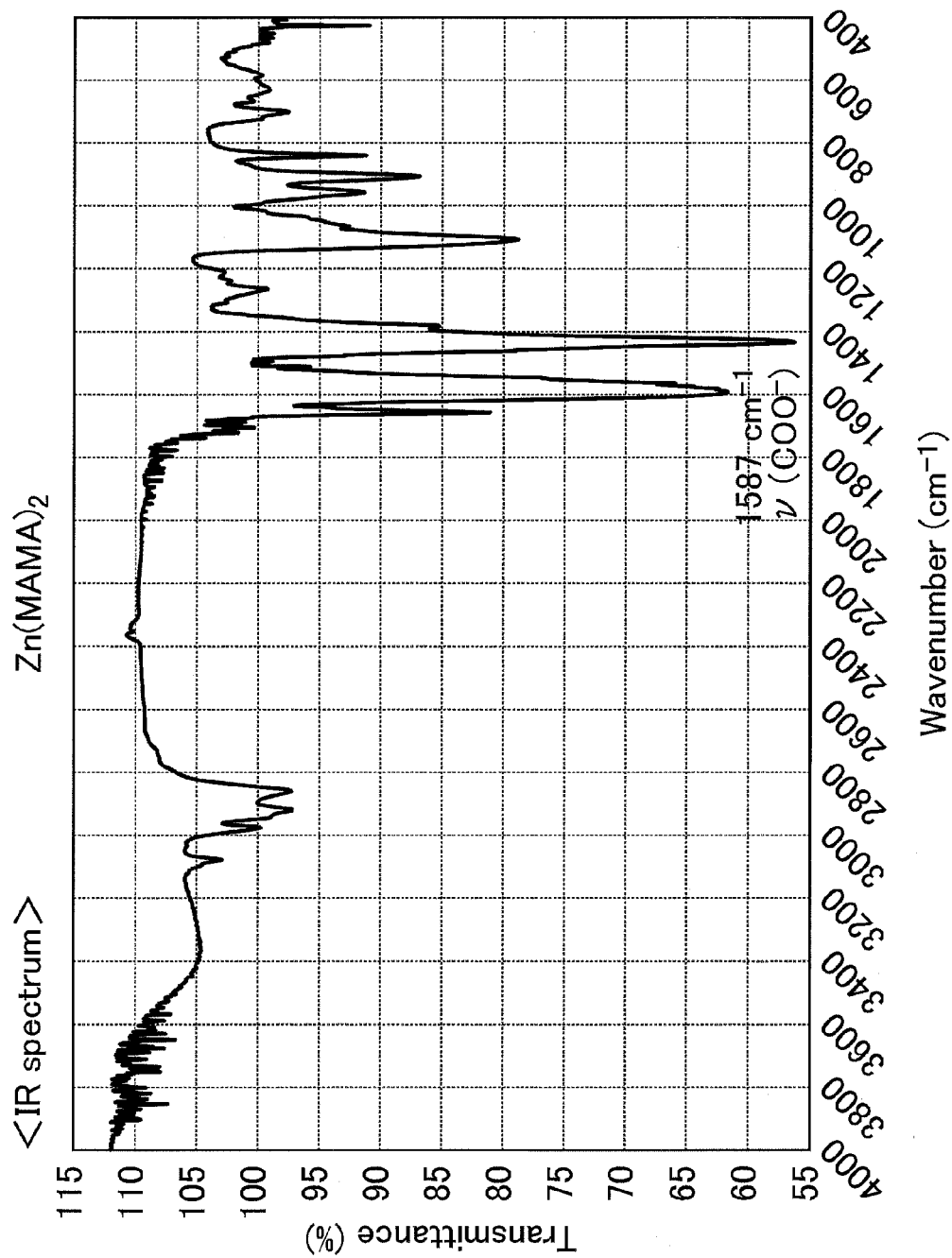

The obtained toluene solution was measured by $^1$H-NMR and IR in the same manner as in Example 1-4. FIGS. 13-1 and 13-2 show the obtained spectra and the assignment of the peaks in NMR measurement and in IR measurement. Table 1 shows the value of $\nu(COO^-)$. In addition, analysis using ICP atomic emission spectrometry was carried out in the same manner as in Example 1-4, and a strong peak assigned to zinc was observed.

Example 1-6

Synthesis of a salt (($C_2H_5$)$_3$NH(AMA)) of α-allyloxymethylacrylate anion (AMA$^-$) and ammonium ion (($C_2H_5$)$_3$NH$^+$)

A reaction vessel containing a stirrer was charged with toluene (10.0 parts) and triethyl amine (2.1 parts). While the mixture was cooled in a water bath and stirred with a magnetic stirrer, a dilute solution of H-AMA (2.9 parts) in toluene (10.0 parts) was added dropwise thereto. The stirring was continued for 30 minutes after the completion of the dropwise addition, and then toluene was evaporated with an evaporator. The toluene was completely removed using a vacuum pump, and thereby ($C_2H_5$)$_3$NH(AMA) (5.0 parts) was obtained in a state of a colorless transparent liquid with a low-viscosity.

Figures 1, 14:
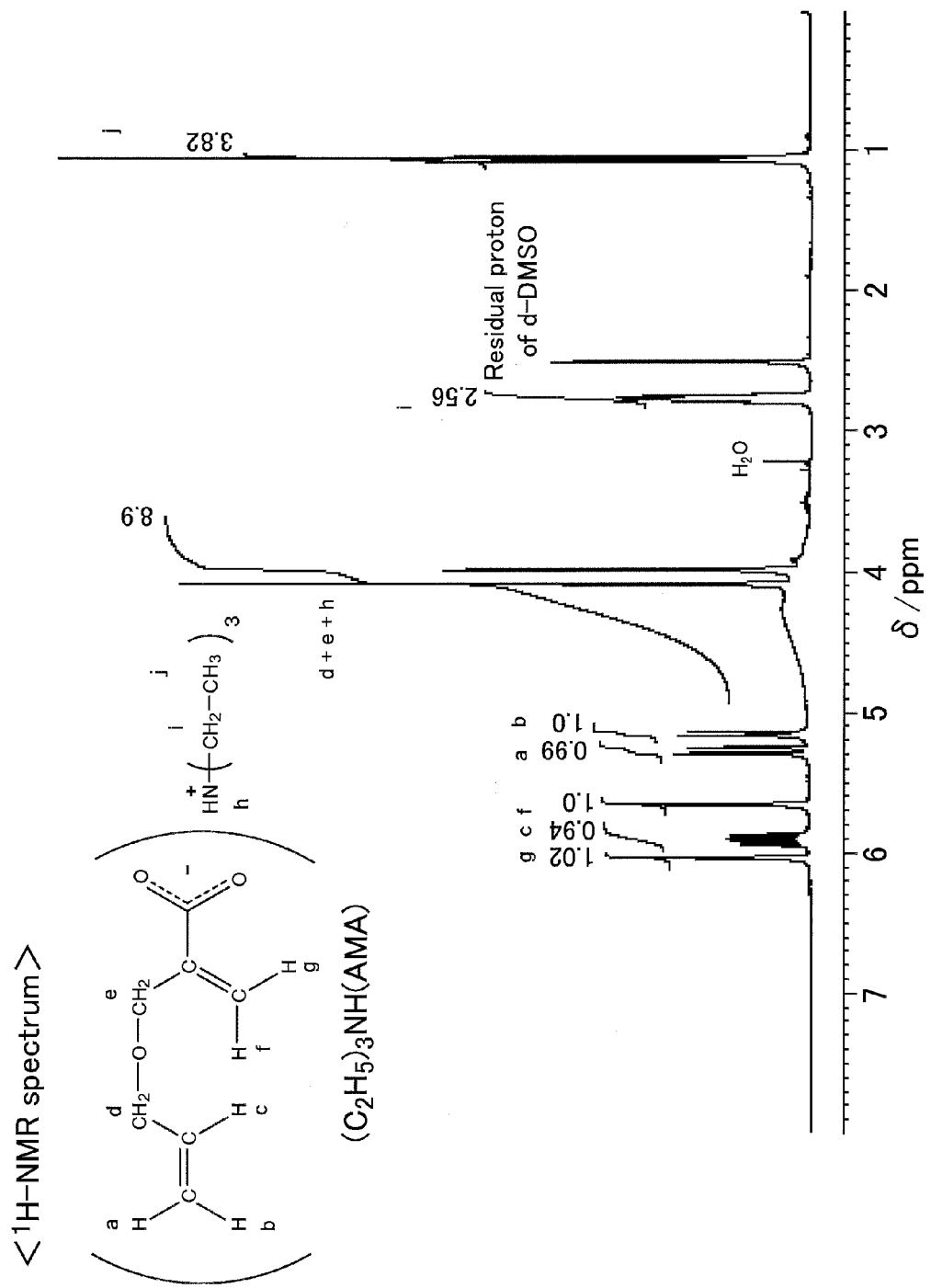
Figures 2, 14:
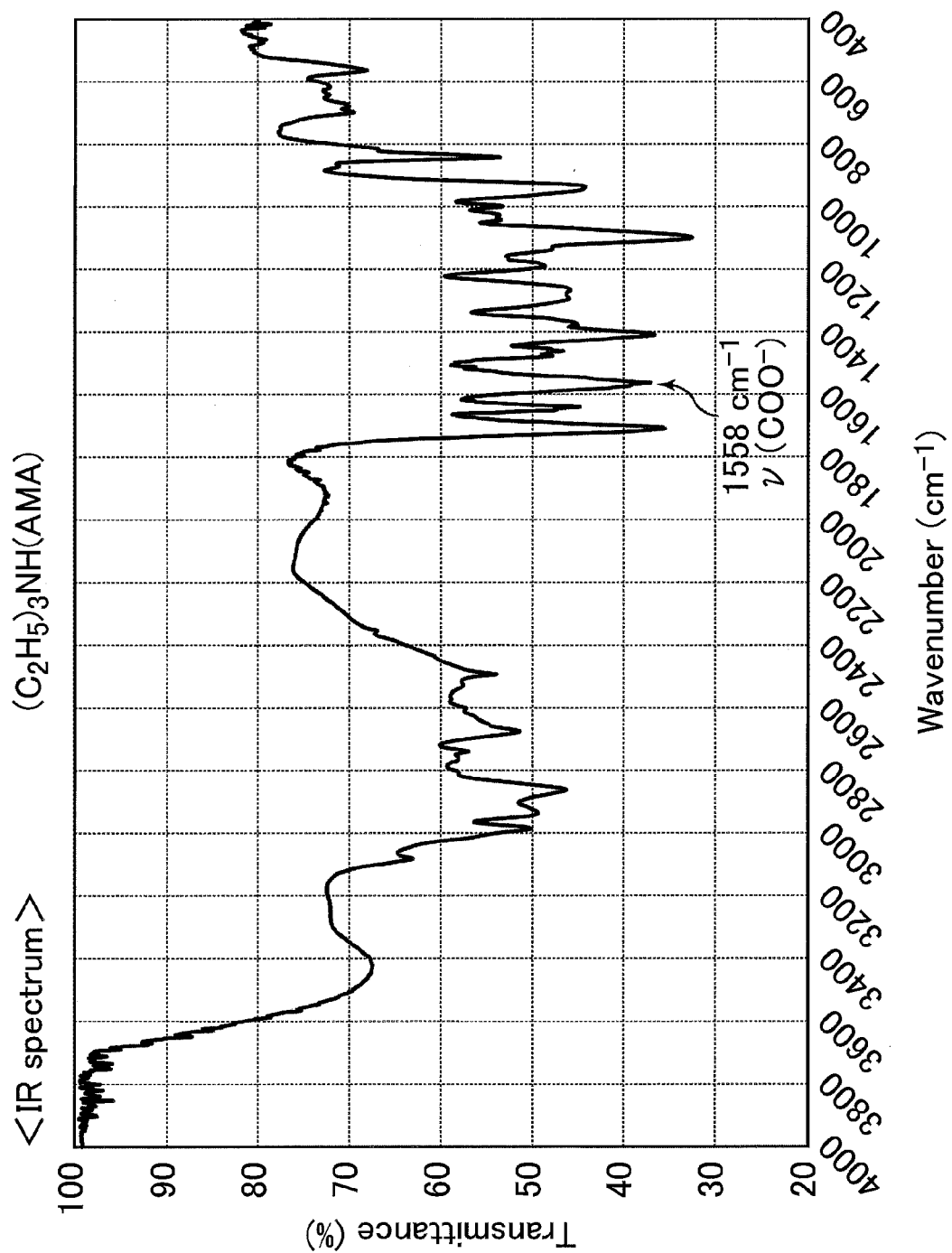

The obtained ($C_2H_5$)$_3$NH(AMA) was measured by $^1$H-NMR and IR in the same manner as in Synthesis Example 1. FIGS. 14-1 and 14-2 show the obtained spectra and the assignment of the peaks in NMR measurement and in IR measurement. Table 1 shows the value of $\nu(COO^-)$.

Example 1-7

Synthesis of a salt (Ba (AMA)$_2$) of α-allyloxymethylacrylate anion (AMA$^-$) and barium ion (Ba$^{2+}$)

A reaction vessel containing a stirrer was charged with toluene (15.0 parts) and H-AMA (4.6 parts). While the mixture was cooled in a water bath and stirred with a magnetic stirrer, barium hydroxide octahydrate (5.1 parts) was added thereto, and the resulting mixture was stirred for one hour. To the mixture was added toluene (30.0 parts), and the toluene and generated water were evaporated with an evaporator and the solution was concentrated. Thereby, a toluene solution (18.5 parts) of Ba (AMA)$_2$ was obtained in a state of a colorless transparent liquid.

The obtained toluene solution was measured by $^1$H-NMR and IR in the same manner as in Example 1-4, and the obtained spectrum was found to be assigned to AMA. Table 1 shows the value of $\nu(COO^-)$ obtained in the IR measurement.

Example 1-8

Synthesis of a salt (Bi(AMA)$_3$) of α-allyloxymethylacrylate anion (AMA$^-$) and bismuth ion (Bi$^{3+}$)

A reaction vessel containing a stirrer was charged with a 10% NaOH aqueous solution (20.2 parts) and Me-AMA (7.6 parts), and the mixture was stirred with a magnetic stirrer while cooled in a water bath. The stirring was continued until Me-AMA disappeared (the disappearance was confirmed by HPLC analysis). Then, H-AMA (0.2 parts) was added to the mixture and the resulting mixture was stirred for 30 minutes, thereby neutralizing an excessive amount of NaOH. Dichloromethane (30 ml) was added thereto, followed by addition of bismuth nitrate pentahydrate (8.0 parts), and the resulting mixture was stirred for one hour.

The contents were transferred to a dropping funnel. The contents were extracted and separated with dichloromethane, and TPA (0.002 parts) and AS2112 (0.008 parts) were added to the dichloromethane layer. Toluene was added to the dichloromethane layer, and dichloromethane was evaporated with an evaporator to concentrate the solution. Such operations were repeated, and thereby toluene solution (21.0 parts) of Bi (AMA)$_3$ was obtained in a state of a colorless to pale yellow transparent liquid.

The obtained toluene solution was measured by $^1$H-NMR and IR in the same manner as in Example 1-4, and the obtained spectrum was found to be assigned to AMA$^-$. Table 1 shows the value of $\nu(COO^-)$ measured by IR measurement. Analysis by ICP atomic emission spectrometry was carried out in the same manner as in Example 1-4, and thereby a strong peak assigned to bismuth was observed.

Example 1-9

Synthesis of a salt (($CH_3$)$_2$Sn (AMA)$_2$) of α-allyloxymethylacrylate anion (AMA$^-$) and dialkyltin ion (($CH_3$)$_2$Sn$^{2+}$)

A reaction vessel containing a stirrer was charged with a 10% NaOH aqueous solution (31.9 parts) and Me-AMA (12.2 parts), and the mixture was stirred with a magnetic stirrer while cooled in a water bath. The stirring was continued until Me-AMA disappeared (the disappearance was confirmed by HPLC analysis). Then, H-AMA (0.3 parts) was added thereto and the mixture was stirred for 30 minutes, thereby neutralizing an excess amount of NaOH. Dichloromethane (30 ml) was added thereto, followed by addition of dimethyltin chloride (8.7 parts), and the mixture was stirred for one hour.

The contents were transferred to a dropping funnel. The contents were extracted and separated with dichloromethane, and TPA (0.004 parts) and AS2112 (0.014 parts) were added to the dichloromethane layer. Toluene was added to the dichloromethane layer, and dichloromethane was evaporated with an evaporator to concentrate the solution. Such operations were repeated, and thereby a toluene solution (32.6 parts) of $(CH_3)_2Sn\,(AMA)_2$ was obtained in a state of a colorless transparent liquid.

Figures 1, 15:
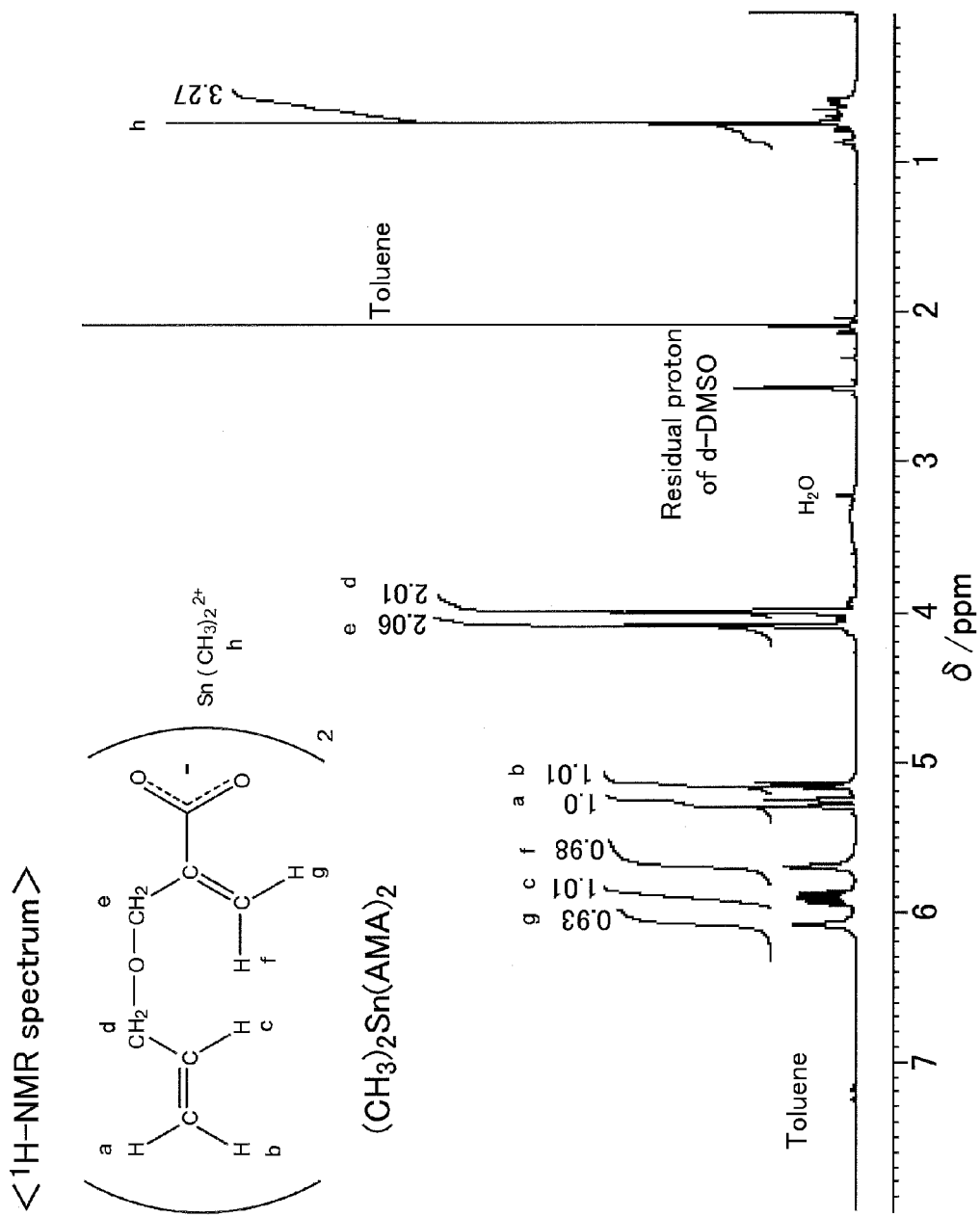
Figures 2, 15:
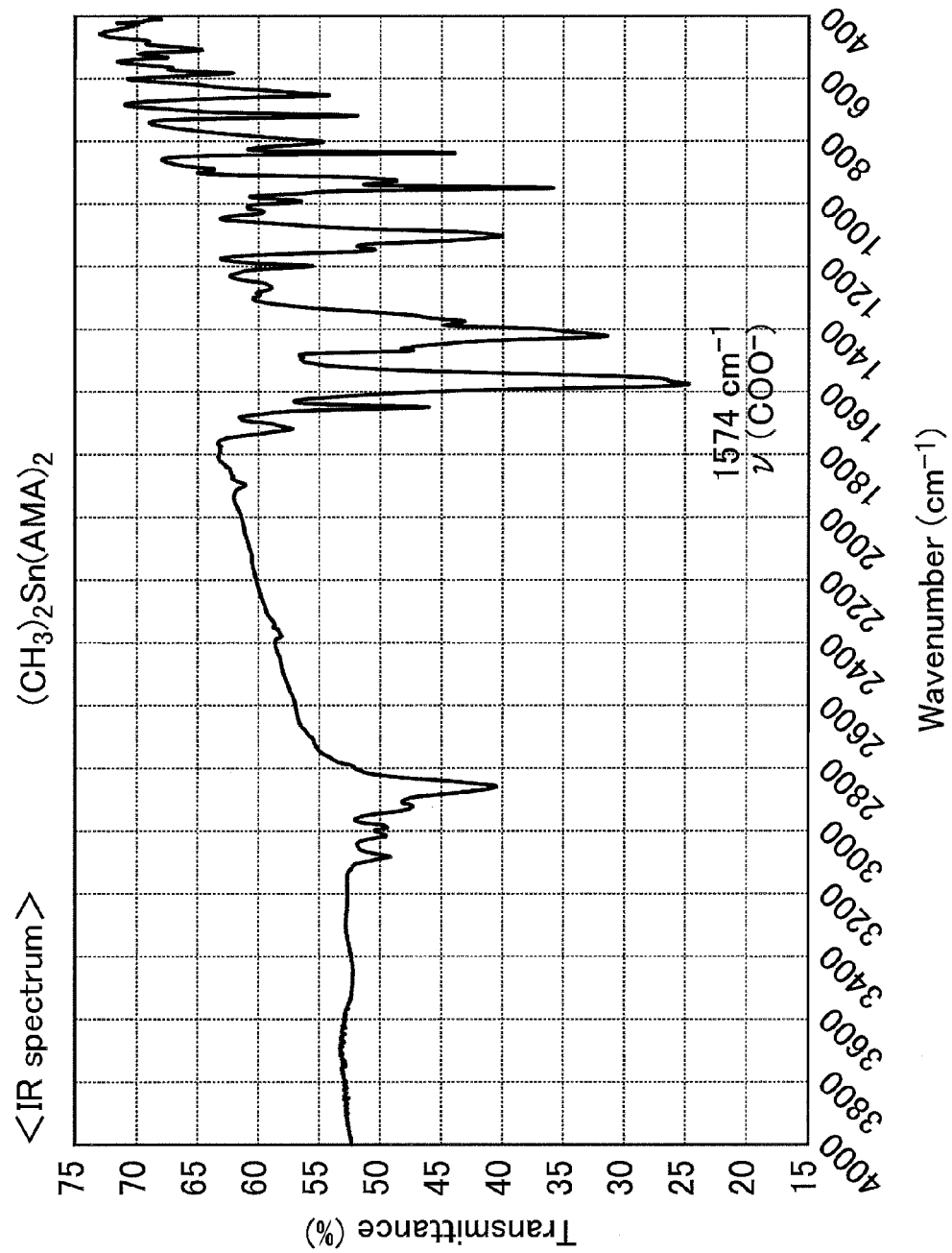

The obtained toluene solution was measured by $^1$H-NMR and IR in the same manner as in Example 1-4. FIGS. 15-1 and 15-2 show the spectra and the assignment of the peaks in NMR measurement and in IR measurement. Table 1 shows the value of $v(COO^-)$. In addition, ICP atomic emission spectrometry analysis was carried out in the same manner as in Example 1-4, and thereby a strong peak assigned to tin was observed.

Example 1-10

Synthesis of a salt $((CH_3)_2Sn\,(AMA)_1(MAA)_1)$ of α-allyloxymethylacrylate anion (AMA), methacrylate anion (MAA$^-$), and dialkyltin ion $((CH_3)_2 Sn^{2+})$ A reaction vessel containing a stirrer was charged with a 10% NaOH aqueous solution (50.2 parts) and Me-AMA (9.8 parts), and the mixture was stirred with a magnetic stirrer while cooled in a water bath. The stirring was continued until Me-AMA disappeared (the disappearance was confirmed by HPLC analysis). Then, methacrylic acid (MAA) (5.4 parts) was added and the mixture was stirred for 30 minutes, thereby neutralizing an excess amount of NaOH. Dichloromethane (30 ml) was added thereto, followed by addition of dimethyltin chloride (13.6 parts), and the mixture was stirred for one hour.

The contents were transferred to a dropping funnel. The contents were extracted and separated with dichloromethane, and TPA (0.005 parts) and AS2112 (0.016 parts) were added to the dichloromethane layer. Toluene was added to the dichloromethane layer, and dichloromethane was evaporated with an evaporator to concentrate the solution. Such operations were repeated, and thereby a toluene solution (49.8 parts) of $(CH_3)_2Sn(AMA)_1(MAA)_1$ was obtained in a state of a colorless transparent liquid.

The obtained toluene solution was measured by $^1$H-NMR and IR in the same manner as in Example 1-4, and thereby the obtained spectra were found to be assigned to AMA$^-$ and MAA$^-$, and the ratio between these was 1/1. Table 1 shows the value of $v(COO^-)$ obtained by IR measurement.

Example 1-11

Synthesis of a salt $(Al(AMA)_3)$ of α-allyloxymethylacrylate anion (AMA$^-$) and aluminum ion $(Al^{3+})$ A reaction vessel containing a stirrer was charged with a 10% NaOH aqueous solution (27.6 parts) and Me-AMA (9.0 parts), and the mixture was stirred with a magnetic stirrer while cooled in a water bath. The stirring was continued until Me-AMA disappeared (the disappearance was confirmed by HPLC analysis). Then, H-AMA (1.6 parts) was added and the mixture was stirred for 30 minutes, thereby neutralizing an excessive amount of NaOH. Dichloromethane (50 ml) was added to the mixture, followed by addition of aluminum nitrate nonahydrate (8.4 parts), and then the resulting mixture was stirred for 30 minutes.

The contents were transferred to a dropping funnel. The contents were extracted and separated with dichloromethane, and TPA (0.002 parts) and AS2112 (0.008 parts) were added to the dichloromethane layer. Dichloromethane was evaporated with an evaporator to concentrate the solution, such that the total amount of the solution was about 60 ml, and thereby a dichloromethane solution of $Al(AMA)_3$ was obtained.

A small amount of the dichloromethane solution was collected, d-DMSO was added thereto, and then dichloromethane was removed using a vacuum pump. The resulting product was measured by $^1$H-NMR measurement. Separately, a small amount of the dichloromethane solution was collected and the solution was measured by IR in the same manner as in Example 1-4. The obtained NMR spectrum and the IR spectrum were found to be assigned to AMA$^-$. Table 1 shows the value of $v(COO^-)$ obtained by IR measurement.

To the residual dichloromethane solution of $Al(AMA)_3$ was added a propylene glycol monomethyl ether (PGM) and the mixture was concentrated by evaporating the dichloromethane with an evaporator. Such operations were repeated, and thereby a PGM solution (21.0 parts) of $Al(AMA)_3$ was obtained in a state of a colorless transparent liquid. In order to prevent gradual hydrolysis by the moisture in the air, the obtained PGM solution was sealed in a glass container, and the glass container was stored in a metal container with dry silica gel spread in the bottom.

Example 1-12

Synthesis of a salt $(In\,(AMA)_3)$ of α-allyloxymethylacrylate anion (AMA$^-$) and indium ion $(In^{3+})$ A reaction vessel containing a stirrer was charged with a 10% NaOH aqueous solution (9.5 parts) and Me-AMA (3.1 parts), and the mixture was stirred with a magnetic stirrer while cooled in a water bath. The stirring was continued until Me-AMA disappeared (the disappearance was confirmed by HPLC analysis), and then H-AMA (0.6 parts) was added and the mixture was stirred for 30 minutes, thereby neutralizing an excessive amount of NaOH. Then, toluene (50 ml) was added thereto, followed by addition of indium nitrate trihydrate (2.8 parts), and the resulting mixture was stirred for one hour.

The contents were transferred to a dropping funnel, and were extracted and separated with toluene. To the toluene layer were added TPA (0.001 parts) and AS2112 (0.003 parts). Toluene was evaporated with an evaporator and $In(AMA)_3$ was thereby precipitated. $In(AMA)_3$ was dissolved again in THF (80 ml).

A small amount of the THF solution was collected and measured by $^1$H-NMR and IR in the same manner as in Example 1-4. The obtained NMR spectrum and the IR spectrum were found to be assigned to AMA$^-$. Table 1 shows the value of $v(COO^-)$ obtained by IR measurement.

The THF in the residual THF solution of $In(AMA)_3$ was evaporated with an evaporator, and the solution was concentrated and thereby a THF solution (20.6 parts) of In(AMA)$_3$ was obtained in a state of a colorless transparent liquid.

Example 1-13

Synthesis of a salt (In (AMA)$_2$(MAA)$_1$) of α-allyloxymethylacrylate anion (AMA$^-$), metacrylate anion (MAA$^-$), and indium ion (In$^{3+}$)

A reaction vessel containing a stirrer was charged with a 10% NaOH aqueous solution (14.9 parts) and Me-AMA (2.9 parts), and the mixture was stirred with a magnetic stirrer while cooled in a water bath. The stirring was continued until Me-AMA disappeared (the disappearance was confirmed by HPLC analysis). Then, MAA (1.6 parts) was added and the mixture was stirred for 30 minutes, thereby neutralizing an excessive amount of NaOH. Then, toluene (50 ml) was added thereto, followed by addition of indium nitrate trihydrate (4.3 parts), and the resulting mixture was stirred for one hour.

The contents were transferred to a dropping funnel. The contents were extracted and separated with toluene, and TPA (0.001 parts) and AS2112 (0.003 parts) were added to the toluene layer. Then, toluene was evaporated with an evaporator to concentrate the solution until the total amount was about 50 ml.

Figures 1, 16:
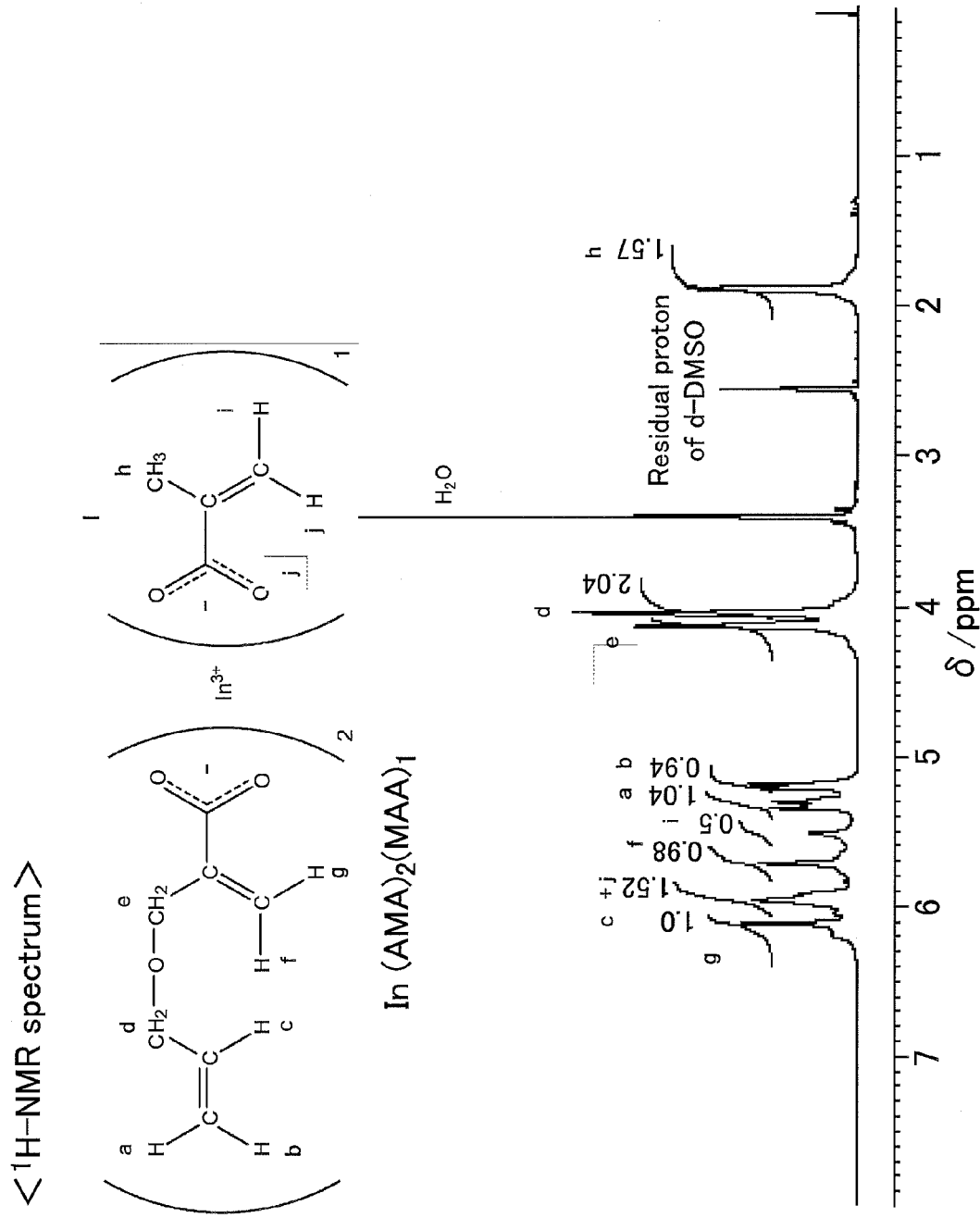
Figures 2, 16:
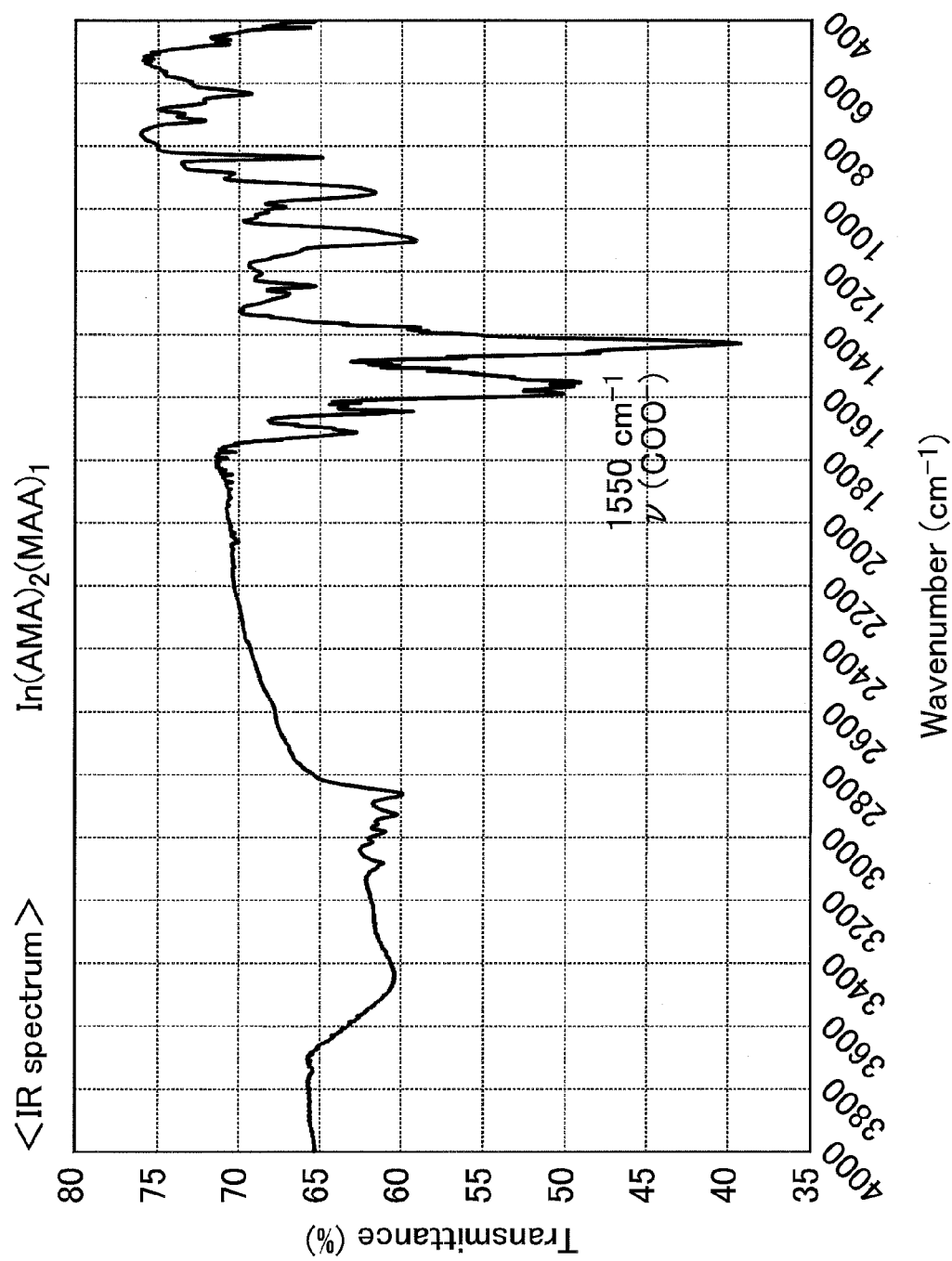

The obtained toluene solution was measured by $^1$H-NMR and IR in the same manner as in Example 1-4. FIGS. 16-1 and 16-2 show the spectra and the assignment of the peaks by NMR and by IR. Table 1 shows the value of ν(COO$^-$). In addition, ICP atomic emission spectrometry analysis was carried out in the same manner as in Example 1-4, and thereby a strong peak assigned to indium was observed.

The toluene in the residual toluene solution was evaporated with an evaporator, and the solution was concentrated and thereby a toluene solution (12.6 parts) of In(AMA)$_2$(MAA)$_1$ was obtained in a state of a colorless transparent liquid.

Example 1-14

Synthesis of a salt (ZrO(AMA)$_2$) of α-allyloxymethylacrylate anion (AMA$^-$) and zirconium oxide ion (ZrO$^{2+}$)

A reaction vessel containing a stirrer was charged with a 10% sodium hydroxide aqueous solution (35.3 parts) and Me-AMA (13.4), and the mixture was stirred with a magnetic stirrer while cooled in a water bath. The stirring was continued until Me-AMA disappeared (the disappearance was confirmed by HPLC analysis). Then, toluene (50 ml) was added, followed by addition of zirconium oxychloride octahydrate (13.7 parts), and then the resulting mixture was stirred for one hour.

The contents were transferred to a dropping funnel. The contents were extracted and separated with toluene, and TPA (0.005 parts) and AS2112 (0.016 parts) were added to the toluene layer. Toluene was evaporated with an evaporator to concentrate the solution, and thereby a toluene solution (43.7 parts) of ZrO(AMA)$_2$ was obtained in a state of a colorless transparent liquid.

Figures 1, 17:
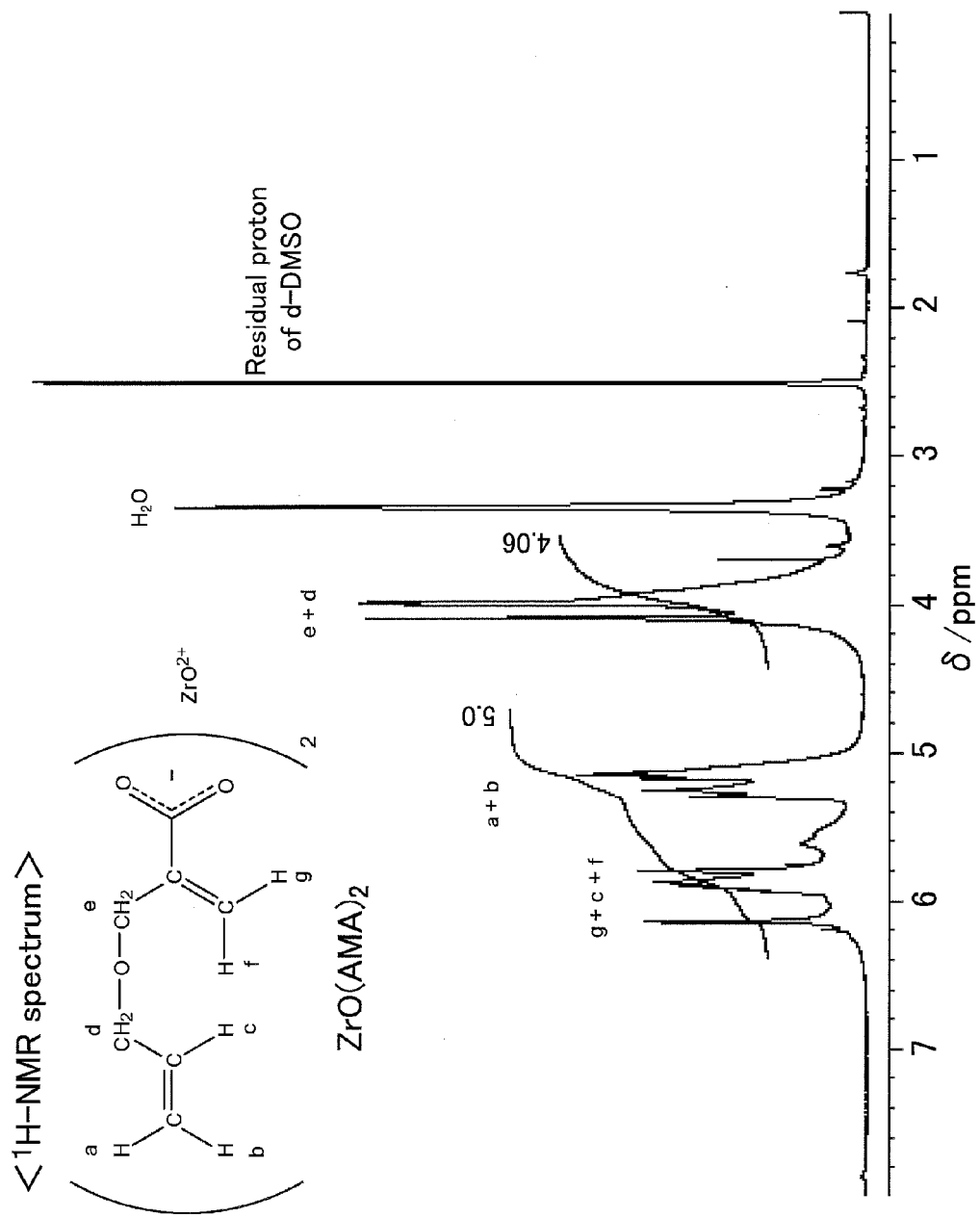
Figures 2, 17:
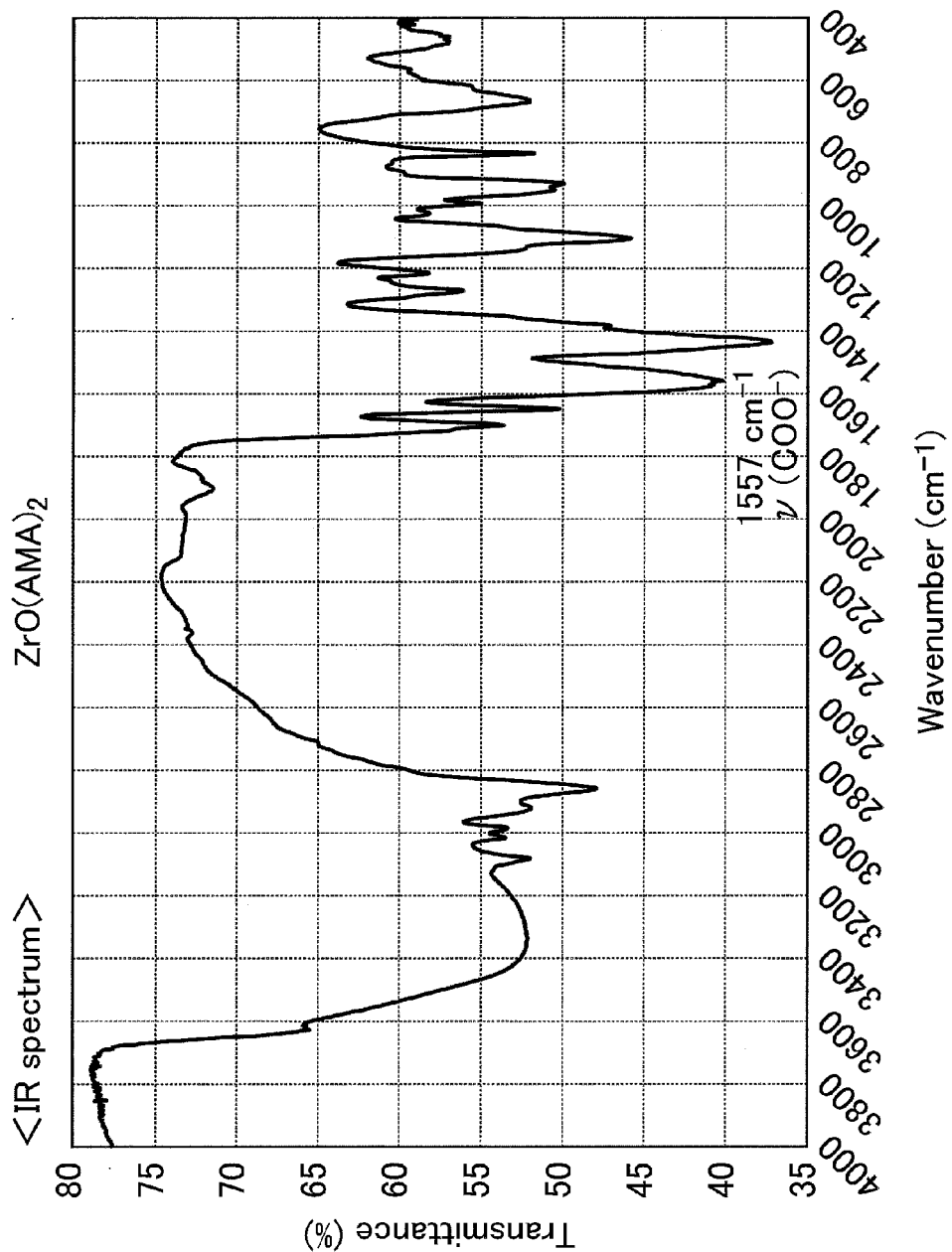

The obtained toluene solution was measured by $^1$H-NMR and IR in the same manner as in Example 1-4. FIGS. 17-1 and 17-2 show the spectra and the assignment of the peaks by NMR and by IR. Table 1 shows the value of ν(COO$^-$). In addition, ICP atomic emission spectrometry analysis was carried out in the same manner as in Example 1-4, whereby a strong peak assigned to zirconium was observed.

Example 1-15

Synthesis of a salt ((n-C$_3$H$_7$O)$_2$Zr (AMA)$_2$) of α-allyloxymethylacrylate anion (AMA$^-$) and zirconium alkoxide ion ((n-C$_3$H$_7$O)$_2$Zr$^{2+}$)

A reaction vessel equipped with a dropping funnel and a stirrer was prepared. Under a stream of dry nitrogen, the reaction vessel was charged with a n-propanol solution (25.2 parts) of 75% zirconium tetra-n-propoxide and dichloromethane (50.0 parts), and the dropping funnel was charged with a dilute solution of H-AMA (16.4 parts) in dichloromethane (40.0 parts)

While the system was cooled in a water bath and the mixture in the reaction vessel was stirred with a magnetic stirrer, the dichloromethane solution of H-AMA was added dropwise from the dropping funnel. Then, dichloromethane which was a solvent and generated n-propanol were removed with a vacuum pump, whereby a pale yellow liquid (29.6 parts) was obtained.

Figures 1, 18:
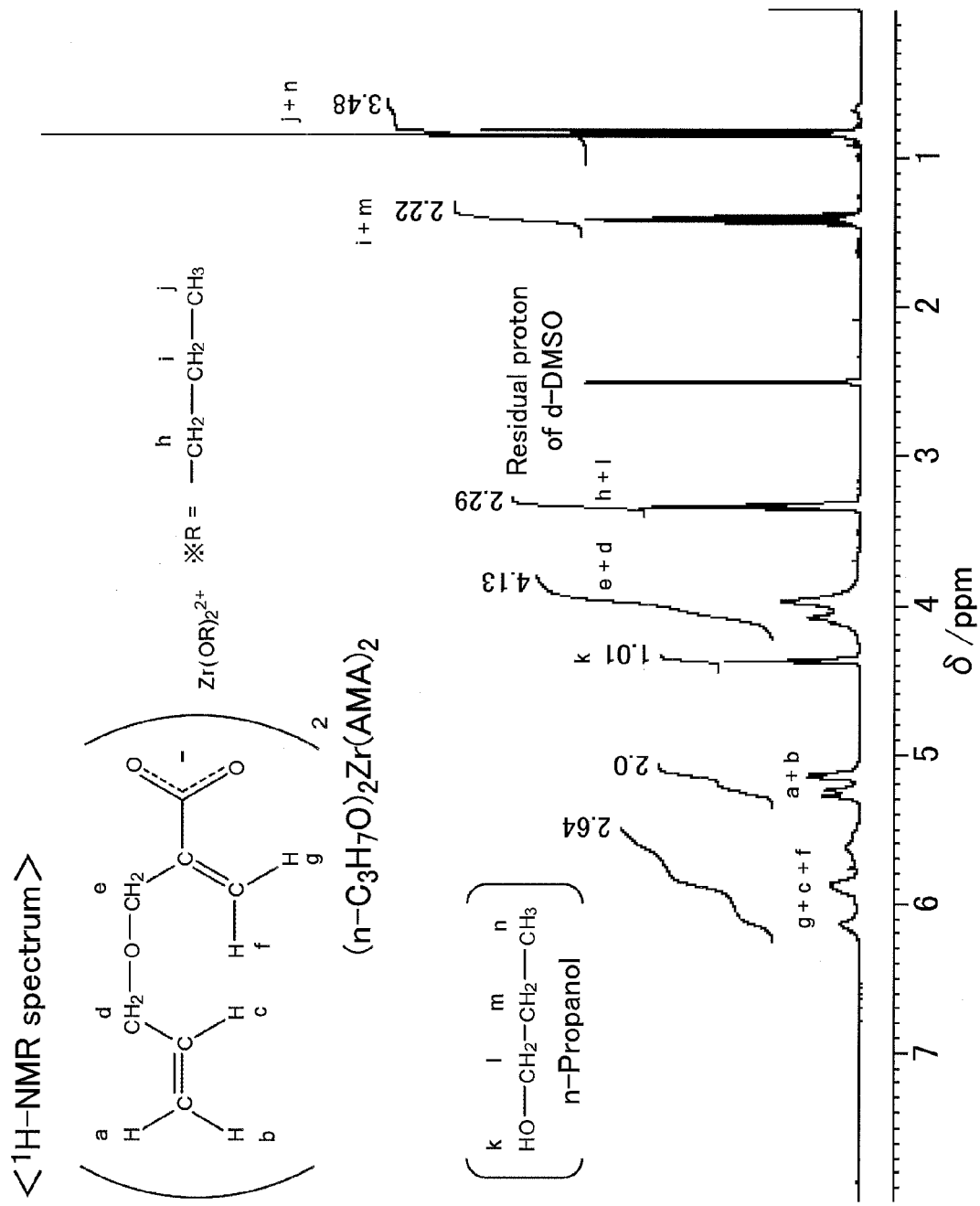
Figures 2, 18:
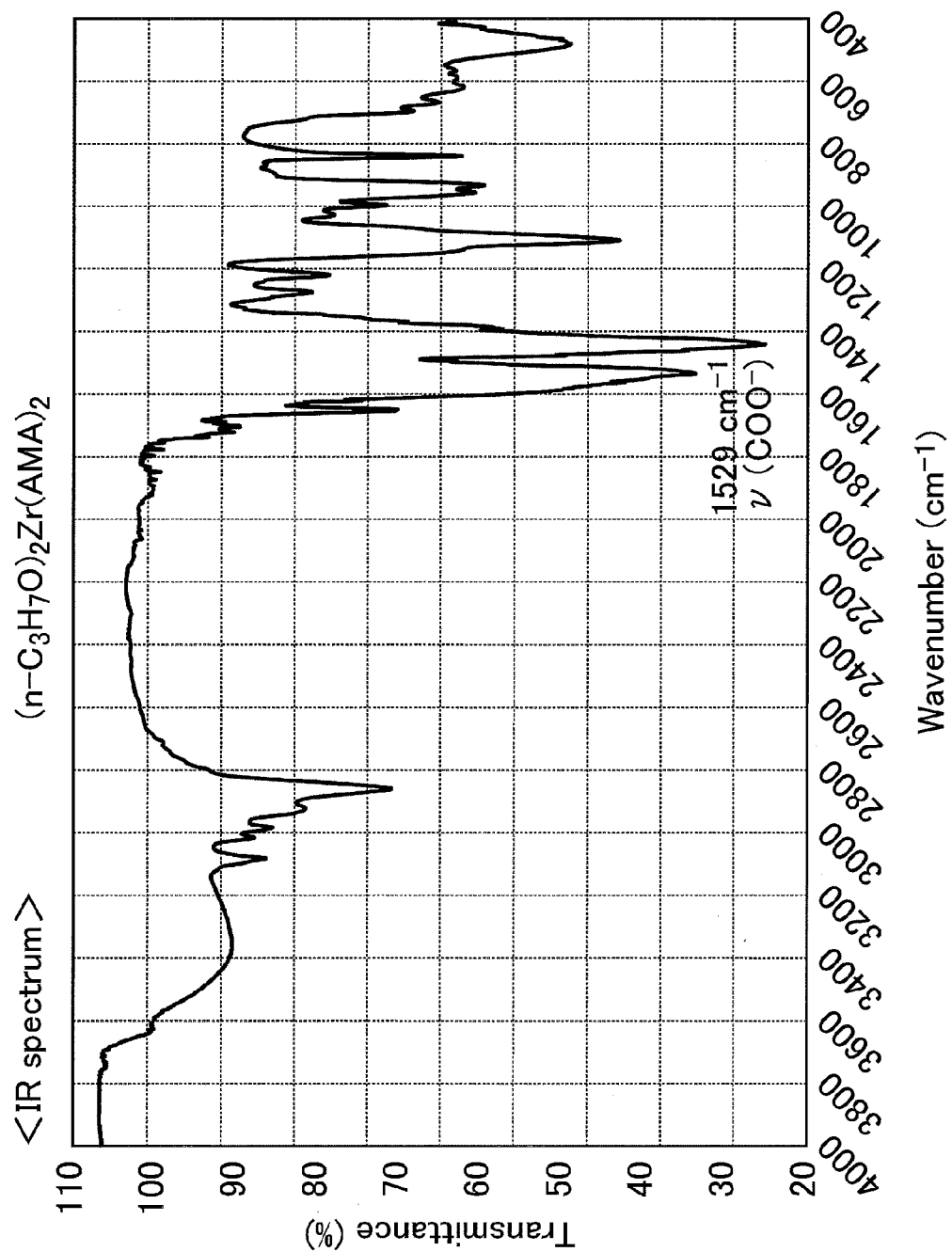

The obtained liquid was measured by $^1$H-NMR and IR in the same manner as in Synthesis Example 1. Thereby, the obtained liquid was found to be (n-C$_3$H$_7$O)$_2$Zr(AMA)$_2$ containing a small amount of n-propanol. FIGS. 18-1 and 18-2 show the spectra and the assignment of the peaks by NMR and by IR. Table 1 shows the value of ν(COO$^-$).

Example 1-16

Synthesis of a salt that contains α-allyloxymethylacrylate anion (AMA$^-$) and zirconoxane oligomer ion and is represented by the following formula

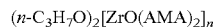

(n-C$_3$H$_7$O)$_2$[ZrO(AMA)$_2$]$_n$

A reaction vessel equipped with a dropping funnel and a stirrer was prepared. Under a stream of dry nitrogen, the reaction vessel was charged with (n-C$_3$H$_7$O)$_2$Zr (AMA)$_2$ (10.0 parts) containing a small amount of n-propanol obtained in Example 1-15 and toluene (20 parts). Under stirring with a magnetic stirrer, distilled water (0.35 parts) was added and the mixture was heated in a hot water bath such that the internal temperature was 50° C. After stirring the mixture for one hour, toluene and generated n-propanol were removed, and thereby a high viscous yellow liquid (8.5 parts) was obtained.

The obtained high viscous liquid was measured by $^1$H-NMR and IR in the same manner as in Example 1-4, whereby the liquid was found to be a salt of AMA$^-$ and a zirconoxane oligomer ion, containing a small amount of n-propanol. Table 1 shows the value of ν(COO$^-$). It was estimated from the $^1$H-NMR spectrum that n is about 3, in other words, the resulting salt was a trimer.

[Chem. 12]

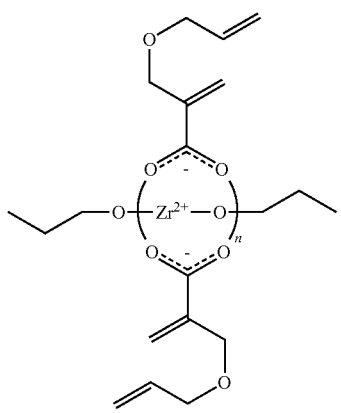

In the formula, n represents an integer of 2 or more, and the formula indicates that this substance has a zirconoxane structure in which —Zr—O— is repeated.

Example 1-17

Synthesis of a salt ((i-C$_3$H$_7$O)$_2$Ti(AMA)$_2$) of α-allyloxymethylacrylate anion (AMA$^-$) and titanium alkoxide ion ((i-C$_3$H$_7$O)$_2$Ti$^{2+}$)

A reaction vessel equipped with a dropping funnel and a stirrer was prepared. Under a stream of dry nitrogen, the reaction vessel was charged with titanium tetraisopropoxide (16.7 parts) and dichloromethane (20.0 parts), and the dropping funnel was charged with a dilute solution of H-AMA (16.7 parts) in dichloromethane (30.0 parts). While the system was cooled in a water bath and the mixture in the reaction vessel was stirred with a magnetic stirrer, the dichloromethane solution of H-AMA was added dropwise from the dropping funnel. Then, dichloromethane which is a solvent and generated isopropanol were removed with a vacuum pump, and thereby a yellow liquid (27.9 parts) was obtained.

The obtained liquid was measured by $^1$H-NMR and IR in the same manner as in Synthesis Example 1, and thereby the liquid was found to be (i-C$_3$H$_7$O)$_2$Ti(AMA)$_2$ that includes a small amount of isopropanol. Table 1 shows the value of ν(COO$^-$).

Example 1-18

Synthesis of a salt that contains α-allyloxymethylacrylate anion (AMA$^-$) and titanoxane oligomer ion and is represented by the following formula (i-C$_3$H$_7$O)$_2$[TiO(AMA)$_2$]$_n$ A reaction vessel equipped with a dropping funnel and a stirrer was prepared. Under a stream of dry nitrogen, the reaction vessel was charged with (i-C$_3$H$_7$O)$_2$Ti(AMA)$_2$ (4.7 parts) containing a small amount of isopropanol obtained in Example 1-17, and toluene (20 parts). Under stirring with a magnetic stirrer, distilled water (0.19 parts) was added thereto and the mixture was heated in a hot water bath such that the internal temperature was 50° C. After stirring the mixture for one hour, toluene and generated isopropanol were removed, and thereby a high viscous yellowish brown liquid (4.0 parts) was obtained.

The obtained high viscous liquid was measured by $^1$H-NMR and IR in the same manner as in Example 1-4, and thereby the liquid was found to be a salt of AMA$^-$ and a titanoxane oligomer ion, containing a small amount of isopropanol. Table 1 shows the value of ν(COO$^-$). It was estimated from the $^1$H-NMR spectrum that n is about 10, in other words, the resulting salt was a decamer.

[Chem. 13]

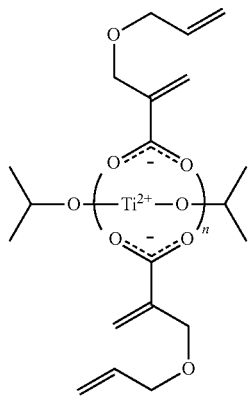

In the formula, n represents an integer of 2 or more, and the formula indicates that this substance has a titanoxane structure in which —Ti—O— is repeated.

Example 1-19

Synthesis of a salt (La(AMA)$_3$) of α-allyloxymethylacrylate anion (AMA$^-$) and lanthanum ion (La$^{3+}$)

A reaction vessel containing a stirrer was charged with a 10% NaOH aqueous solution (30.7 parts) and Me-AMA (11.7 parts), and the mixture was stirred with a magnetic stirrer while cooled in a water bath. The stirring was continued until Me-AMA disappeared (the disappearance was confirmed by HPLC analysis). Then, toluene (40 ml) was added, followed by addition of lanthanum chloride heptahydrate (9.2 parts), and then the resulting mixture was stirred for one hour.

The contents were transferred to a dropping funnel. The contents were extracted and separated with toluene, and TPA (0.003 parts) and AS2112 (0.01 parts) were added to the toluene layer. Toluene was evaporated with an evaporator to concentrate the solution, and thereby a toluene solution (50.3 parts) of La(AMA)$_3$ was obtained in a state of a colorless transparent liquid.

The obtained toluene solution was measured by $^1$H-NMR and IR in the same manner as in Example 1-4, and thereby the obtained spectrum was found to be assigned to AMA. Table 1 shows the value of ν(COO$^-$) obtained by IR measurement. In addition, ICP atomic emission spectrometry analysis was carried out in the same manner as in Example 1-4, whereby a strong peak assigned to lanthanum was observed.

Example 1-20

Synthesis of a salt (Eu(AMA)$_3$) of α-allyloxymethylacrylate anion (AMA$^-$) and europium ion (Eu$^{3+}$)

A reaction vessel containing a stirrer was charged with a 10% NaOH aqueous solution (1.9 parts) and Me-AMA (0.7 parts), and the mixture was stirred with a magnetic stirrer while cooled in a water bath. The stirring was continued until Me-AMA disappeared (the disappearance was confirmed by HPLC analysis). Then, toluene (20 ml) was added thereto, followed by addition of europium nitrate hexahydrate (0.6 parts), and then the resulting mixture was stirred for one hour.

The contents were transferred to a dropping funnel. The contents were extracted and separated with toluene. Toluene was evaporated with an evaporator to concentrate the solution, and thereby a toluene solution (6.2 parts) of Eu(AMA)$_3$ was obtained in a state of a colorless transparent liquid.

The obtained toluene solution was measured by $^1$H-NMR and IR in the same manner as in Example 1-4, and thereby the obtained spectrum was found to be assigned to AMA$^-$. Table 1 shows the value of ν(COO$^-$) obtained by IR measurement. In addition, ICP atomic emission spectrometry analysis was carried out in the same manner as in Example 1-4, and thereby a strong peak assigned to europium was observed.

Example 1-21

Synthesis of a salt (Er(AMA)$_3$) of α-allyloxymethylacrylate anion (AMA) and erbium ion (Er$^{3+}$)

A reaction vessel containing a stirrer was charged with a 10% NaOH aqueous solution (10.8 parts) and Me-AMA (3.7 parts), and the mixture was stirred with a magnetic stirrer while cooled in a water bath. The stirring was continued until Me-AMA disappeared (the disappearance was confirmed by HPLC analysis). Then, H-AMA (0.5 parts) was added and the mixture was stirred for 30 minutes, thereby neutralizing an excessive amount of NaOH. Then, toluene (60 ml) was added thereto, followed by addition of erbium chloride hexahydrate (3.4 parts), and the resulting mixture was stirred for one hour.

The contents were transferred to a dropping funnel. The contents were extracted and separated with toluene, and toluene was evaporated with an evaporator to precipitate Er (AMA)$_3$. The obtained Er (AMA)$_3$ was dissolved again in THF (80 ml), and then THF was evaporated to concentrate the solution, whereby a THF solution (29.0 parts) of Er(AMA)$_3$ was obtained in a state of a pale pink transparent liquid.

The obtained THF solution was measured by $^1$H-NMR and IR in the same manner as in Example 1-4. In the NMR measurement, the magnetic field was less likely to be locked, and therefore the obtained spectrum showed broad peaks. Table 1 shows the value of ν(COO$^-$) obtained by the IR measurement. In addition, H-AMA was observed by HPLC analysis (this is because phosphoric acid included in the elution solvent turned AMA$^-$ into H-AMA). Moreover, a strong peak assigned to erbium was observed by ICP atomic emission spectrometry analysis carried out in the same manner as in Example 1-4.

Example 1-22

Synthesis of a salt ((C$_2$H$_5$O)$_2$Nb (AMA)$_3$) of α-allyloxymethylacrylate anion (AMA$^-$) and niobium alkoxide ion ((C$_2$H$_5$O)$_2$Nb$^{3+}$)

A reaction vessel equipped with a dropping funnel and a stirrer was prepared. Under a stream of dry nitrogen, the reaction vessel was charged with niobium pentaethoxide (1.6 parts) and toluene (20.0 parts), and the dropping funnel was charged with a dilute solution of H-AMA (2.1 parts) in toluene (20.0 parts). While the mixture in the reaction vessel was cooled in a water bath and was stirred with a magnetic stirrer, the toluene solution of H-AMA was added dropwise from the dropping funnel. Then, toluene which was a solvent and generated ethanol were evaporated, and the solution was concentrated using a vacuum pump, whereby an yellow transparent toluene solution (9.7 parts) was obtained.

The obtained toluene solution was measured by $^1$H-NMR and IR in the same manner as in Example 1-4. Thereby, the solution was found to be (C$_2$H$_5$O)$_2$Nb(AMA)$_3$ containing a small amount of ethanol. Table 1 shows the value of ν(COO$^-$).

Example 1-23

Synthesis of a salt (Ag(AMA)) of α-allyloxymethylacrylate anion (AMA) and silver ion (Ag$^+$)

A reaction vessel containing a stirrer was charged with a 10% NaOH aqueous solution (10.5 parts) and Me-AMA (3.3 parts), and the mixture was stirred with a magnetic stirrer while cooled in a water bath. The stirring was continued until Me-AMA disappeared (the disappearance was confirmed by HPLC analysis). Then, H-AMA (0.9 parts) was added and the mixture was stirred for 30 minutes, thereby neutralizing an excessive amount of NaOH. To the mixture was added a 10% silver nitrate aqueous solution, and the resulting mixture was stirred for one hour.

The resulting precipitate was separated by filtering, washed with distilled water and acetone, and then dried with a vacuum pump, whereby white powder (2.9 parts) was obtained.

Figures 1, 19:
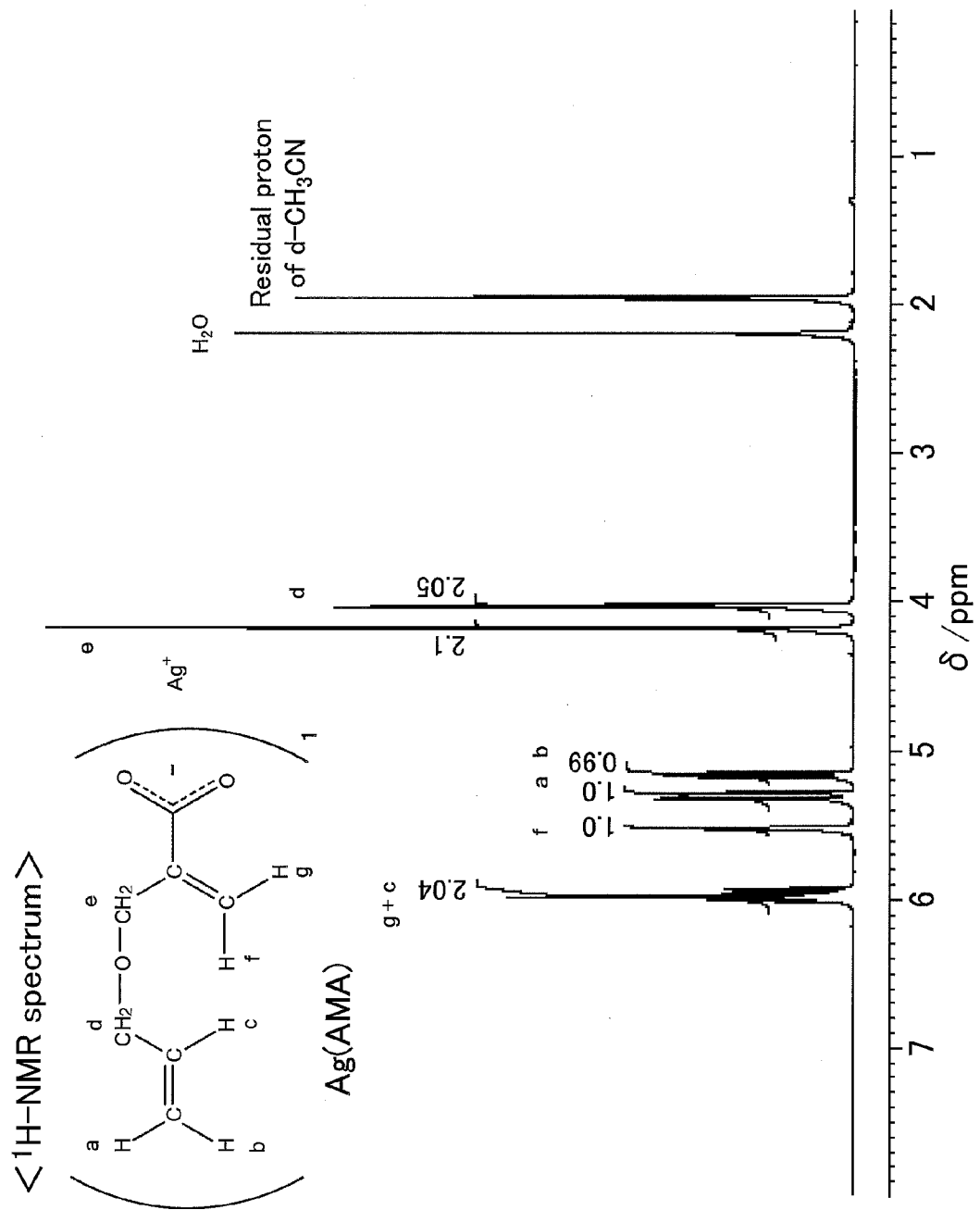
Figures 2, 19:
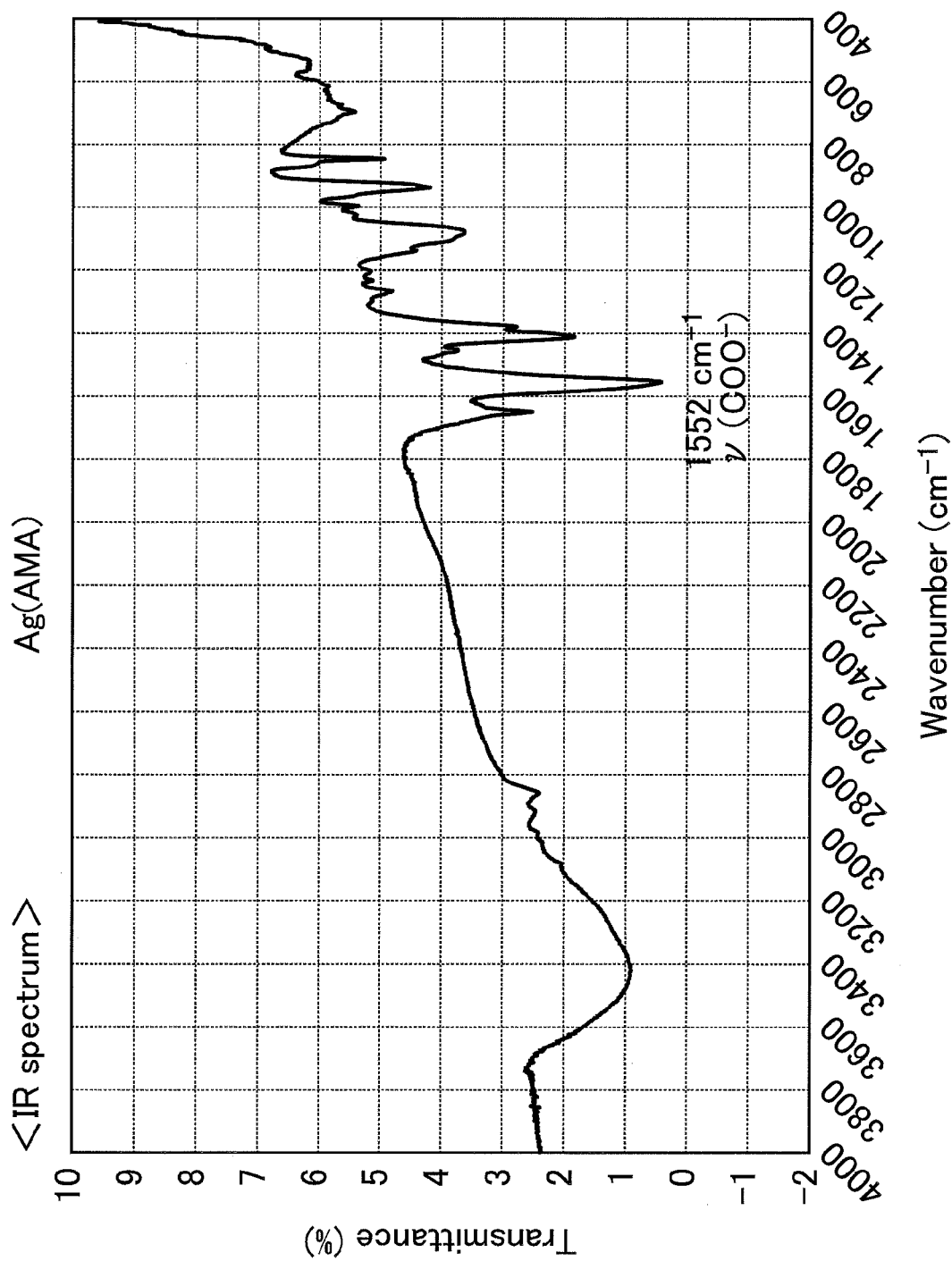

The obtained powder was dissolved in deuterated acetonitrile, and the resulting solution was measured by $^1$H-NMR. FIG. 19-1 shows the obtained spectrum and the assignment of the peaks. In addition, IR measurement was carried out by KBr tablet method. FIG. 19-2 shows the obtained spectrum and the assignment of the peaks, and Table 1 shows the value of ν(COO$^-$).

In addition, the obtained powder was analyzed by X-ray fluorescence, and a strong peak assigned to silver was observed.

Example 1-24

Synthesis of a salt (Au(AMA)$_3$) of α-allyloxymethylacrylate anion (AMA$^-$) and gold ion (Au$^{3+}$)

A reaction vessel containing a stirrer was charged with a 10% NaOH aqueous solution (3.0 parts) and Me-AMA (1.0 part), and the mixture was stirred with a magnetic stirrer while cooled in a water bath. The stirring was continued until Me-AMA disappeared (the disappearance was confirmed by HPLC analysis). Then, H-AMA (0.2 parts) was added and the mixture was stirred for 30 minutes, thereby neutralizing an excessive amount of NaOH. To the resulting mixture was added 1-butanol (40 ml), followed by addition of sodium tetrachloroaurate dihydrate (1.0 part), and then the mixture was stirred for 20 minutes.

The contents were transferred to a dropping funnel. The contents were extracted and separated with 1-butanol, and then 1-butanol was evaporated with an evaporator to concentrate the solution. Thereby, a 1-butanol solution of Au(AMA)$_3$ (6.5 parts) was obtained in a state of an yellow transparent liquid.

The obtained 1-butanol solution was measured by $^1$H-NMR and IR in the same manner as in Example 1-4, and thereby the obtained spectrum was found to be assigned to AMA$^-$. Table 1 shows the value of v(COO$^-$) obtained by IR measurement. In addition, ICP atomic emission spectrometry analysis was carried out in the same manner as in Example 1-4, and thereby a strong peak assigned to gold was observed.

Example 1-25

Synthesis of a salt (Cu(AMA)$_2$) of α-allyloxymethylacrylate anion (AMA$^-$) and copper ion (Cu$^{2+}$)

A reaction vessel containing a stirrer was charged with THF (40.0 parts), copper hydroxide (1.5 parts), and H-AMA (4.4 parts), and the mixture was stirred with a magnetic stirrer until the copper hydroxide was dissolved and the mixture in the system changed into a transparent solution. Then, THF was evaporated with an evaporator and the solution was concentrated. The concentrated solution was filtered through a filter with pores each of which has the size of 0.45 µm, and thereby a slightly greenish dark blue THF solution (16.0 parts) was obtained.

The obtained THF solution was measured by $^1$H-NMR and IR in the same manner as in Example 1-4. In the NMR measurement, the magnetic field was less likely to be locked, and therefore the obtained spectrum showed broad peak. Table 1 shows the value of v(COO$^-$) obtained by IR measurement. In addition, H-AMA was observed by HPLC analysis (this is because phosphoric acid included in the elution solvent turned AMA$^-$ into H-AMA).

Example 1-26

Synthesis of a salt (Cu(AMA)$_1$(AA)$_1$) of α-allyloxymethylacrylate anion (AMA$^-$), acrylate anion (AA$^-$), and copper ion (Cu$^{2+}$)

A reaction vessel containing a stirrer was charged with THF (40.0 parts), copper hydroxide (1.5 parts), H-AMA (2.2 parts), and acrylic acid (AA) (1.1 parts), and the mixture was stirred with a magnetic stirrer until the copper hydroxide was dissolved and the mixture in the system changed into a transparent solution. Then, THF was evaporated with an evaporator and the solution was concentrated. The concentrated solution was filtered through a filter with pores each of which has the size of 0.45 µm, whereby a slightly greenish dark blue THF solution (12.6 parts) was obtained.

The obtained THF solution was measured by $^1$H-NMR and IR in the same manner as in Example 1-4. In the NMR measurement, the magnetic field was less likely to be locked, and therefore the obtained spectrum showed broad peak. Table 1 shows the value of v(COO$^-$) obtained by IR measurement. In addition, H-AMA and acrylic acid were observed by HPLC analysis (this is because phosphoric acid included in the elution solvent turned AMA into H-AMA, and AA into an acrylic acid).

Example 1-27

Synthesis of a salt (Cr(AMA)$_3$) of α-allyloxymethylacrylate anion (AMA$^-$) and chromium ion (Cr$^{3+}$)

A reaction vessel containing a stirrer was charged with a 10% NaOH aqueous solution (10.0 parts) and Me-AMA (3.8 parts), and the mixture was stirred with a magnetic stirrer while cooled in a water bath. The stirring was continued until Me-AMA disappeared (the disappearance was confirmed by HPLC analysis). Then, H-AMA (0.1 parts) was added and the mixture was stirred for 30 minutes, thereby neutralizing an excessive amount of NaOH. Toluene (30 ml) was added thereto, followed by addition of chromium chloride hexahydrate (2.2 parts), and the resulting mixture was stirred for one hour.

The contents were transferred to a dropping funnel, and the contents were extracted and separated with toluene. To the toluene layer were added TPA (0.001 parts) and AS2112 (0.003 parts). Then, toluene was evaporated with an evaporator and the solution was concentrated. Thereby, a toluene solution (9.8 parts) of Cr (AMA)$_3$ was obtained in a state of a bluish black liquid.

The obtained toluene solution was measured by $^1$H-NMR and IR in the same manner as in Example 1-4, except that deuterated chloroform was used as a deuterated solvent. In the NMR measurement, the magnetic field was less likely to be locked, and therefore the obtained spectrum showed broad peak. Table 1 shows the value of v(COO$^-$) obtained by IR measurement. In addition, H-AMA was observed by HPLC analysis (this is because phosphoric acid included in the elution solvent turned AMA$^-$ into H-AMA). In addition, ICP atomic emission spectrometry analysis was carried out in the same manner as in Example 1-4, whereby a strong peak assigned to chromium was observed.

Example 1-28

Synthesis of a salt (Ni(AMA)$_1$(MAA)$_1$) of α-allyloxymethylacrylate anion (AMA$^-$), methacrylate anion (MAA$^-$), and nickel ion (Ni$^{2+}$)

A reaction vessel containing a stirrer was charged with a 10% NaOH aqueous solution (10.3 parts) and Me-AMA (2.0 parts), and the mixture was stirred with a magnetic stirrer while cooled in a water bath. The stirring was continued until Me-AMA disappeared (the disappearance was confirmed by HPLC analysis). Then, methacrylic acid (1.1 parts) was added and the mixture was stirred for 30 minutes, thereby neutralizing an excessive amount of NaOH. Toluene (30 ml) was added thereto, followed by addition of nickel sulfate hexahydrate (3.3 parts), and the resulting mixture was stirred for one hour.

The contents were transferred to a dropping funnel, and the contents were extracted and separated with toluene. To the toluene layer was TPA (0.001 parts) and AS2112 (0.003 parts), and was evaporated with an evaporator and the solution was concentrated. Thereby, a toluene solution (10.6 parts) of Ni (AMA)$_1$(MAA)$_1$ was obtained in a state of a pale green liquid.

The obtained toluene solution was measured by $^1$H-NMRand IR in the same manner as in Example 1-4, except that deuterated chloroform was used as a deuterated solvent. In the NMR measurement, the magnetic field was less likely to be locked, and therefore the obtained spectrum showed broad peak. Table 1 shows the value of $\nu(COO^-)$ obtained by the IR measurement. In addition, H-AMA and methacrylic acid were observed by HPLC analysis (this is because phosphoric acid included in the elution solvent turned $AMA^-$ into H-AMA and $MMA^-$ into methacrylic acid). In addition, ICP atomic emission spectrometry analysis was carried out in the same manner as in Example 1-4, whereby a strong peak assigned to nickel was observed.

Example 1-29

Synthesis of a salt (Fe $(AMA)_3$) of α-allyloxymethylacrylate anion ($AMA^-$) and iron ion ($Fe^{3+}$)

A reaction vessel containing a stirrer was charged with a 10% NaOH aqueous solution (15.6 parts) and Me-AMA (5.9 parts), and the mixture was stirred with a magnetic stirrer while cooled in a water bath. The stirring was continued until Me-AMA disappeared (the disappearance was confirmed by HPLC analysis). Then, toluene (30 ml) was added, followed by addition of iron nitrate nonahydrate (3.3 parts), and the resulting mixture was stirred for one hour.

The contents were transferred to a dropping funnel, and were extracted and separated with toluene. To the toluene layer were added TPA (0.001 parts) and AS2112 (0.003 parts), and then toluene was evaporated with an evaporator to concentrate the solution. Thereby, a toluene solution (15.3 parts) of Fe $(AMA)_3$ was obtained in a state of a yellowish to reddish brown liquid.

The obtained toluene solution was measured by $^1$H-NMR and IR in the same manner as in Example 1-4. In the NMR measurement, the magnetic field was less likely to be locked, and therefore the obtained spectrum showed broad peak. Table 1 shows the value of $\nu(COO^-)$ obtained by the IR measurement. In addition, H-AMA was observed by HPLC analysis (this is because phosphoric acid included in the elution solvent turned $AMA^-$ into H-AMA). In addition, ICP atomic emission spectrometry analysis was carried out in the same manner as in Example 1-4, whereby a strong peak assigned to iron was observed.

Example 1-30

Synthesis of a salt (Fe$(AMA)_2(AA)_1$) of α-allyloxymethylacrylate anion ($AMA^-$), acrylate anion ($AA^-$), and iron ion ($Fe^{3+}$)

A reaction vessel containing a stirrer was charged with a 10% NaOH aqueous solution (15.1 parts) and Me-AMA (3.9 parts), and the mixture was stirred with a magnetic stirrer while cooled in a water bath. The stirring was continued until Me-AMA disappeared (the disappearance was confirmed by HPLC analysis). Then, AA (0.9 parts) was added and the mixture was stirred for 30 minutes, thereby neutralizing an excessive amount of NaOH. Toluene (30 ml) was added, followed by addition of iron nitrate nonahydrate (3.3 parts), and then the resulting mixture was stirred for one hour.

The contents were transferred to a dropping funnel and were extracted and separated with toluene. To the toluene layer were added TPA (0.001 parts) and AS2112 (0.003 parts), and toluene was evaporated with an evaporator to concentrate the solution. Thereby, a toluene solution (19.6 parts) of F $(AMA)_2 (AA)_1$ was obtained in a state of a yellowish to reddish brown liquid.

The obtained toluene solution was measured by $^1$H-NMR and IR in the same manner as in Example 1-4. In the NMR measurement, the magnetic field was less likely to be locked, and therefore the obtained spectrum showed broad peak. Table 1 shows the value of $\nu(COO^-)$ obtained by IR measurement. In addition, H-AMA and acrylic acid were observed by HPLC analysis (this is because phosphoric acid included in the elution solvent turned $AMA^-$ into H-AMA, and $AA^-$ into an acrylic acid).

Example 1-31

Synthesis of a salt (Mn$(AMA)_2$) of α-allyloxymethylacrylate anion ($AMA^-$) and manganese ion ($Mn^{2+}$)

A reaction vessel containing a stirrer was charged with a 10% NaOH aqueous solution (7.2 parts) and Me-AMA (2.7 parts), and the mixture was stirred with a magnetic stirrer while cooled in a water bath. The stirring was continued until Me-AMA disappeared (the disappearance was confirmed by HPLC analysis). Then, H-AMA (0.1 parts) was added and the mixture was stirred for 30 minutes, thereby neutralizing an excessive amount of NaOH. Toluene (30 ml) was added, followed by addition of manganese sulfate pentahydrate (2.1 parts), and then the resulting mixture was stirred for one hour.

The contents were transferred to a dropping funnel and were extracted and separated with toluene. To the toluene layer were added TPA (0.001 parts) and AS2112 (0.003 parts), and then toluene was evaporated with an evaporator. Thereby, a toluene solution (11.8 parts) of Mn$(AMA)_2$ was obtained in a state of a pale pink liquid.

The obtained toluene solution was measured by $^1$H-NMR and IR in the same manner as in Example 1-4. In the NMR measurement, the magnetic field was less likely to be locked, and therefore the obtained spectrum showed broad peak. Table 1 shows the value of $\nu(COO^-)$ obtained by the IR measurement. In addition, H-AMA was observed by HPLC analysis (this is because phosphoric acid included in the elution solvent turned $AMA^-$ into H-AMA). In addition, ICP atomic emission spectrometry analysis was carried out in the same manner as in Example 1-4, whereby a strong peak assigned to manganese was observed.

Example 1-32

Synthesis of a salt (Co $(AMA)_2$) of α-allyloxymethylacrylate anion ($AMA^-$) and cobalt ion ($Co^{2+}$)

A reaction vessel containing a stirrer was charged with a 10% NaOH aqueous solution (11.2 parts) and Me-AMA (4.3 parts), and the mixture was stirred with a magnetic stirrer while cooled in a water bath. The stirring was continued until Me-AMA disappeared (the disappearance was confirmed by HPLC analysis). Then, H-AMA (0.1 parts) was added and the mixture was stirred for 30 minutes, thereby neutralizing an excessive amount of NaOH. Toluene (30 ml) was added, followed by addition of cobalt nitrate hexahydrate (3.3 parts), and then the resulting mixture was stirred for one hour.

The contents were transferred to a dropping funnel, and were extracted and separated with toluene. To the toluene layer were added TPA (0.001 parts) and AS2112 (0.003 parts), and then toluene was evaporated with an evaporator to concentrate the solution. Thereby, a toluene solution (15.5 parts) of Co (AMA)$_2$ was observed in a state of a purple liquid.

The obtained toluene solution was measured by $^1$H-NMR and IR in the same manner as in Example 1-4. In the NMR measurement, the magnetic field was less likely to be locked, and therefore the obtained spectrum showed broad peak. Table 1 shows the value of ν(COO$^-$) obtained by the IR measurement. In addition, H-AMA was observed by HPLC analysis (this is because phosphoric acid included in the elution solvent turned AMA into H-AMA). In addition, ICP atomic emission spectrometry analysis was carried out in the same manner as in Example 1-4, whereby a strong peak assigned to cobalt was observed.

TABLE 1

| Example | Formula of salt | ν (COO$^-$) [cm$^{-1}$] | State of sample for IR measurement |
|---|---|---|---|
| 1-1 | Na(AMA) | 1,554 | Aqueous solution |
| 1-3 | K(AMA) | 1,558 | Aqueous solution |
| 1-4 | Zn(AMA)$_2$ | 1,594 | No solvents |
| 1-5 | Zn(MAMA)$_2$ | 1,587 | No solvents |
| 1-6 | (C$_2$H$_5$)$_3$NH(AMA) | 1,558 | No solvents |
| 1-7 | Ba(AMA)$_2$ | 1,541 | No solvents |
| 1-8 | Bi(AMA)$_3$ | 1,548 | No solvents |
| 1-9 | (CH$_3$)$_2$Sn(AMA)$_2$ | 1,574 | No solvents |
| 1-10 | (CH$_3$)$_2$Sn(AMA)$_1$(MAA)$_1$ | 1,570 | No solvents |
| 1-11 | Al(AMA)$_3$ | 1,581 | No solvents |
| 1-12 | In(AMA)$_3$ | 1,548 | No solvents |
| 1-13 | In(AMA)$_2$(MAA)$_1$ | 1,550 | No solvents |
| 1-14 | ZrO(AMA)$_2$ | 1,557 | No solvents |
| 1-15 | (n-C$_3$H$_7$O)$_2$Zr(AMA)$_2$ | 1,529 | No solvents |
| 1-16 | (n-C$_3$H$_7$O)$_2$[ZrO(AMA)$_2$]$_n$ | 1,519 | No solvents |
| 1-17 | (i-C$_3$H$_7$O)$_2$Ti(AMA)$_2$ | 1,514 | No solvents |
| 1-18 | (i-C$_3$H$_7$O)$_2$[TiO(AMA)$_2$]$_n$ | 1,541 | No solvents |
| 1-19 | La(AMA)$_3$ | 1,549 | No solvents |
| 1-20 | Eu(AMA)$_3$ | 1,535 | No solvents |
| 1-21 | Er(AMA)$_3$ | 1,547 | No solvents |
| 1-22 | (C$_2$H$_5$O)$_2$Nb(AMA)$_3$ | 1,522 | No solvents |
| 1-23 | Ag(AMA) | 1,552 | No solvents |
| 1-24 | Au(AMA)$_3$ | 1,554 | No solvents |
| 1-25 | Cu(AMA)$_2$ | 1,601 | No solvents |
| 1-26 | Cu(AMA)$_1$(AA)$_1$ | 1,595 | No solvents |
| 1-27 | Cr(AMA)$_3$ | 1,531 | No solvents |
| 1-28 | Ni(AMA)$_1$(MAA)$_1$ | 1,622 | No solvents |
| 1-29 | Fe(AMA)$_3$ | 1,584 | No solvents |
| 1-30 | Fe(AMA)$_2$(AA)$_1$ | 1,550 | No solvents |
| 1-31 | Mn(AMA)$_2$ | 1,612 | No solvents |
| 1-32 | Co(AMA)$_2$ | 1,620 | No solvents |

<Film-Forming Test on Each Compound>

Examples 2-1 to 2-29, Comparative Examples 2-1 to 2-18

The film-forming ability of each compound was tested as follows. Table 3 shows the results. For the compounds in a solution state, the nonvolatile content was optionally determined as shown in the following and then the film-forming test was carried out.

[Film-Forming Ability]

A liquid having low viscosity enough to be applied with a bar coater, with a compound concentration of 100%, was evaluated as "∘∘" unconditionally.

A solid or a high viscous liquid, with a compound concentration of 100%, was made into a solution using a volatile solvent that dissolves the compound. Thereby, a solution sample was made in which the compound concentration was known based on the weight of the compound used for the solution and of the volatile solvent. If no volatile solvent was suitable for making the compound into a solution with a concentration of about 10%, the compound was evaluated as "x" unconditionally.

For a compound with an unknown concentration, the nonvolatile content was measured according to the below method, and the obtained value was defined as the compound concentration.

Each compound was appropriately diluted with a volatile solvent to have a slightly adjusted concentration, whereby an application solution was prepared. The application solution was applied to a glass plate with a suitably selected bar coater such that the dried film thickness (calculated value) was 2.4 to 2.6 μm. The dried film thickness (calculated value) was calculated according to the following formula:

Dried film thickness(calculated value)[μm]=1.3×(bar coater No.)×(compound concentration(mass %))÷100

The applied compound was dried in a vacuum dryer at 80° C. for 10 minutes. The dried film was visually observed (a loupe was optionally used), and the film-forming ability was evaluated according to the criteria shown in Table 2. Table 3 shows the results.

TABLE 2

| Evaluation | Film forming | Powder/crystal precipitation | Transparency |
|---|---|---|---|
| ∘∘ | Formed | None | Transparent |
| ∘ | Formed | None to slightly precipitated | Transparent to partially slightly translucent |
| Δ | Formed | Partially precipitated | Partially translucent but not opaque |
| X-Δ | Formed | Precipitated overall | Partially opaque |
| X | Not formed | Precipitated overall | Partially opaque |

TABLE 3

| | | Compound | | Application liquid | | Film-forming ability |
|---|---|---|---|---|---|---|
| | | Formula/Abbreviation | Derivation, product name (company name), etc. | Compound concentration | Solvent | |
| Example | 2-1 | Zn(AMA)$_2$ | Example 1-4 | 32.0 | Toluene | ∘∘ |
| | 2-2 | Zn(MAMA)$_2$ | Example 1-5 | 38.5 | Toluene | ∘∘ |
| | 2-3 | (C$_2$H$_5$)$_3$NH(AMA) | Example 1-6 | 100 | — | ∘∘ |
| | 2-4 | Ba(AMA)$_2$ | Example 1-7 | 32.1 | Toluene | ∘∘ |
| | 2-5 | Bi(AMA)$_3$ | Example 1-8 | 39.3 | Toluene | ∘∘ |
| | 2-6 | (CH$_3$)$_2$Sn(AMA)$_2$ | Example 1-9 | 45.7 | Toluene | ∘∘ |
| | 2-7 | (CH$_3$)$_2$Sn(AMA)$_1$(MAA)$_1$ | Example 1-10 | 32.0 | Toluene | ∘∘ |
| | 2-8 | Al(AMA)$_3$ | Example 1-11 | 32.0 | PGM | ∘∘ |

TABLE 3-continued

| | | Compound | | Application liquid | | Film-forming ability |
|---|---|---|---|---|---|---|
| | | Formula/Abbreviation | Derivation, product name (company name), etc. | Compound concentration | Solvent | |
| | 2-9 | $In(AMA)_3$ | Example 1-12 | 15.3 | THF | X-Δ |
| | 2-10 | $In(AMA)_2(MAA)_1$ | Example 1-13 | 28.0 | Toluene | ○ |
| | 2-11 | $ZrO(AMA)_2$ | Example 1-14 | 37.3 | Toluene | ○○ |
| | 2-12 | $(n-C_3H_7O)_2Zr(AMA)_2$ | Example 1-15 | 50.0 | Toluene | ○○ |
| | 2-13 | $(n-C_3H_7O)_2[ZrO(AMA)_2]_n$ | Example 1-16 | 50.0 | Toluene | ○○ |
| | 2-14 | $(i-C_3H_7O)_2Ti(AMA)_2$ | Example 1-17 | 50.0 | Toluene | ○○ |
| | 2-15 | $(i-C_3H_7O)_2[TiO(AMA)_2]_n$ | Example 1-18 | 50.0 | Toluene | ○○ |
| | 2-16 | $La(AMA)_3$ | Example 1-19 | 20.5 | Toluene | ○○ |
| | 2-17 | $Eu(AMA)_3$ | Example 1-20 | 10.0 | Toluene | ○○ |
| | 2-18 | $Er(AMA)_3$ | Example 1-21 | 16.2 | Toluene | ○○ |
| | 2-19 | $(C_2H_5O)_2Nb(AMA)_3$ | Example 1-22 | 31.2 | Toluene | ○○ |
| | 2-20 | $Ag(AMA)$ | Example 1-23 | (No solution available) | | X |
| | 2-21 | $Au(AMA)_3$ | Example 1-24 | 13.3 | 1-Butanol | ○○ |
| | 2-22 | $Cu(AMA)_2$ | Example 1-25 | 30.9 | THF | ○○ |
| | 2-23 | $Cu(AMA)_1(AA)_1$ | Example 1-26 | 31.3 | THF | ○○ |
| | 2-24 | $Cr(AMA)_3$ | Example 1-27 | 38.2 | Toluene | ○○ |
| | 2-25 | $Ni(AMA)_1(MAA)_1$ | Example 1-28 | 26.5 | Toluene | ○○ |
| | 2-26 | $Fe(AMA)_3$ | Example 1-29 | 32.6 | Toluene | ○○ |
| | 2-27 | $Fe(AMA)_2(AA)_1$ | Example 1-30 | 20.2 | Toluene | ○○ |
| | 2-28 | $Mn(AMA)_2$ | Example 1-31 | 21.3 | Toluene | X |
| | 2-29 | $Co(AMA)_2$ | Example 1-32 | 23.6 | Toluene | X-Δ |
| Comparative Example | 2-1 | NPGDA | SR247 (SARTOMER) | 100 | — | ○○ |
| | 2-2 | DEGDA | SR230 (SARTOMER) | 100 | — | ○○ |
| | 2-3 | TMPTA | SR351NS (SARTOMER) | 100 | — | ○○ |
| | 2-4 | NPG-AMA | Synthesis Example 3 | 100 | — | ○○ |
| | 2-5 | DEG-AMA | Synthesis Example 4 | 100 | — | ○○ |
| | 2-6 | TMP-AMA | Synthesis Example 5 | 100 | — | ○○ |
| | 2-7 | $Zn(AA)_2$ | Zinc acrylate (Aldrich) | 10.0 | Methanol | Δ |
| | 2-8 | $Zn(MAA)_2$ | Zinc methacrylate (Aldrich) | 10.0 | Methanol | X-Δ |
| | 2-9 | $Zn(Ac)_2$ | Zinc acetate (Wako Pure Chemical Industries, Ltd.) | 20.0 | Water | X |
| | 2-10 | $Zn(Oc)_2$ | Zinc octoate Nikka Octhix Zinc (Nihon Kagaku Sangyo Co., Ltd.) | 50.0 | Toluene | ○○ |
| | 2-11 | $Zr(AA)_4$ | Zirconium acrylate (Aldrich) | 20.0 | Methanol | X-Δ |
| | 2-12 | $Zr(CEA)_4$ | Zirconium carboxyethyl acrylate (Aldrich) | 50.0 | n-Propanol | ○○ |
| | 2-13 | $Mg(AA)_2$ | Magnesium acrylate (Alfa Aesar) | 10.0 | Methanol | X-Δ |
| | 2-14 | $Mg(MAA)_2$ | Magnesium methacrylate (Wako Chemical, Ltd.) | 10.0 | Methanol | X-Δ |
| | 2-15 | $Fe(AA)_3$ | Iron acrylate (Alfa Aesar) | (No solution available) | | X |
| | 2-16 | $Cu(AA)_2$ | Copper acrylate (Alfa Aesar) | 10.0 | Methanol | X-Δ |
| | 2-17 | $Cu(MAA)_2$ | Copper methacrylate (Alfa Aesar) | 10.0 | Methanol | X |
| | 2-18 | $Al(AA)_3$ | Aluminum acrylate (Alfa Aesar) | 10.0 | Methanol | X-Δ |

[Nonvolatile Content]

A test sample (about 0.4 g) was weighed into an aluminum cup, air-dried at room temperature for 30 minutes, and dried in a vacuum dryer at 80° C. for 30 minutes. The dried sample was weighed, and the nonvolatile content was calculated from the residual weight of the test sample.

Solubility Test on Each Compound (Film-Forming Method)

Examples 3-1 to 3-27, Comparative Examples 3-1 to 3-9

Solubility test was carried out on the compounds which were evaluated as "x-Δ" or better in the film-forming test (Examples 2-1 to 2-29, Comparative Examples 2-1 to 2-18) (the compounds that had a low viscosity and a high fluidity at normal temperature were excepted). Each compound was applied on a glass plate and the glass plate was leaned against the wall. Each solvent shown in Table 5 was dropped (5 to 6 drops) on the glass plate with a pasteur pipette. The glass plate was visually observed after the dropped solvent was dried, the surface was optionally rubbed with a spatula, and the solubility (film-forming method) was evaluated according to the criteria shown in Table 4. Table 5 shows the results.

TABLE 4

| | |
|---|---|
| ○○ | Totally dissolved |
| ○ | Mostly dissolved (may have thin-film-like undissolved part) |
| Δ | Dissolved but thin-film-like undissolved part left on the whole |
| X-Δ | Slightly dissolved (drip mark observed) |
| X | Never dissolved (no drip mark) |

TABLE 5

| | | Compound Formula/Abbreviation | Solubility (film-forming method) | | | | | | |
|---|---|---|---|---|---|---|---|---|---|
| | | | Water | Methanol | Acetonitrile | Acetone | THF | Ethyl acetate | Toluene |
| Example | 3-1 | $Zn(AMA)_2$ | X-Δ | OO | OO | OO | OO | OO | OO |
| | 3-2 | $Zn(MAMA)_2$ | X-Δ | OO | OO | OO | OO | OO | OO |
| | 3-3 | $Ba(AMA)_2$ | OO | OO | Δ | Δ | OO | Δ | Δ |
| | 3-4 | $Bi(AMA)_3$ | X-Δ | OO | OO | OO | OO | OO | OO |
| | 3-5 | $(CH_3)_2Sn(AMA)_2$ | X | OO | OO | OO | OO | OO | OO |
| | 3-6 | $(CH_3)_2Sn(AMA)_1(MAA)_1$ | X | OO | OO | OO | OO | OO | OO |
| | 3-7 | $Al(AMA)_3$ | X | Δ | Δ | O | OO | Δ | Δ |
| | 3-8 | $In(AMA)_3$ | X | X-Δ | X-Δ | X-Δ | OO | X-Δ | Δ |
| | 3-9 | $In(AMA)_2(MAA)_1$ | X | X-Δ | OO | OO | OO | OO | Δ |
| | 3-10 | $ZrO(AMA)_2$ | X | O | OO | OO | OO | OO | OO |
| | 3-11 | $(n-C_3H_7O)_2Zr(AMA)_2$ | X | X-Δ | X-Δ | X-Δ | X-Δ | X-Δ | X-Δ |
| | 3-12 | $(n-C_3H_7O)_2[ZrO(AMA)_2]_n$ | X | X-Δ | OO | OO | OO | OO | OO |
| | 3-13 | $(i-C_3H_7O)_2Ti(AMA)_2$ | X | X-Δ | X-Δ | X-Δ | X-Δ | X-Δ | X-Δ |
| | 3-14 | $(i-C_3H_7O)_2[TiO(AMA)_2]_n$ | X | X-Δ | OO | OO | OO | OO | OO |
| | 3-15 | $La(AMA)_3$ | X-Δ | OO | OO | OO | OO | OO | Δ |
| | 3-16 | $Eu(AMA)_3$ | X | OO | OO | OO | OO | OO | OO |
| | 3-17 | $Er(AMA)_3$ | X-Δ | OO | OO | OO | OO | OO | Δ |
| | 3-18 | $(C_2H_5O)_2Nb(AMA)_3$ | X | Δ | Δ | Δ | Δ | Δ | Δ |
| | 3-19 | $Cu(AMA)_2$ | Δ | OO | OO | OO | OO | OO | OO |
| | 3-20 | $Cu(AMA)_1(AA)_1$ | X-Δ | O | O | O | OO | OO | OO |
| | 3-21 | $Au(AMA)_3$ | O | OO | OO | OO | OO | O | X-Δ |
| | 3-22 | $Cr(AMA)_3$ | X | X-Δ | O | OO | OO | O | O |
| | 3-23 | $Ni(AMA)_1(MAA)_1$ | X | O | OO | OO | OO | OO | OO |
| | 3-24 | $Fe(AMA)_3$ | X-Δ | OO | OO | OO | OO | OO | OO |
| | 3-25 | $Fe(AMA)_2(AA)_1$ | X-Δ | OO | OO | OO | OO | OO | OO |
| | 3-26 | $Mn(AMA)_2$ | X-Δ | O | O | OO | OO | OO | OO |
| | 3-27 | $Co(AMA)_2$ | X | X-Δ | X-Δ | O | OO | O | O |
| Comparative Example | 3-1 | $Zn(AA)_2$ | O | OO | Δ | Δ | O | Δ | X |
| | 3-2 | $Zn(MAA)_2$ | X-Δ | O | Δ | Δ | O | Δ | X-Δ |
| | 3-3 | $Zn(Oc)_2$ | Δ | OO | X | OO | OO | O | O |
| | 3-4 | $Zr(AA)_4$ | X | OO | X-Δ | X | X-Δ | X | X |
| | 3-5 | $Zr(CEA)_4$ | Δ | OO | OO | Δ | O | X-Δ | X-Δ |
| | 3-6 | $Mg(AA)_2$ | OO | OO | X-Δ | X-Δ | X-Δ | X | X |
| | 3-7 | $Mg(MAA)_2$ | OO | OO | X | X | X-Δ | X | X |
| | 3-8 | $Cu(AA)_2$ | OO | OO | OO | X-Δ | X-Δ | X | X |
| | 3-9 | $Al(AA)_3$ | OO | OO | X | X | X | X | X |

Solubility Test on Each Compound (Dissolution Method)

Examples 4-1 to 4-28, Comparative Examples 4-1 to 4-9

Each compound shown in Table 7 (optionally vacuum-dried in order to eliminate the solvent) was mixed with each solvent shown in Table 7 such that the resulting mixture had given compound concentrations (1%, 3%, 5%, 10%, and 20% or more). The mixture was evaluated according to the criteria shown in Table 6. Table 7 shows the results.

TABLE 6

| | |
|---|---|
| OO | Become uniform and transparent at a compound concentration of 20% or more |
| O | Become uniform and transparent at a compound concentration of 10% |
| Δ | Become uniform and transparent at a compound concentration of 3% |
| X-Δ | Become uniform and transparent at a compound concentration of 1% |
| X | Not become uniform and transparent even at a compound concentration of 1% |

TABLE 7

| | | Compound Formula/Abbreviation | Solubility (dissolution method) | | | | | | |
|---|---|---|---|---|---|---|---|---|---|
| | | | Water | Methanol | Acetonitrile | Acetone | THF | Ethyl acetate | Toluene |
| Example | 4-1 | $Zn(AMA)_2$ | OO | OO | OO | OO | OO | OO | OO |
| | 4-2 | $Zn(MAMA)_2$ | — | — | — | — | — | — | OO |
| | 4-3 | $(C_2H_5)_3NH(AMA)$ | O | OO | OO | OO | OO | OO | OO |
| | 4-4 | $Ba(AMA)_2$ | — | — | — | — | — | — | OO |
| | 4-5 | $Bi(AMA)_3$ | — | — | — | — | — | — | OO |
| | 4-6 | $(CH_3)_2Sn(AMA)_2$ | — | — | — | — | — | — | OO |
| | 4-7 | $(CH_3)_2Sn(AMA)_1(MAA)_1$ | — | — | — | — | — | — | OO |
| | 4-8 | $Al(AMA)_3$ | X | X | OO | OO | OO | OO | O |
| | 4-9 | $In(AMA)_3$ | — | — | — | — | OO | — | — |
| | 4-10 | $In(AMA)_2(MAA)_1$ | — | — | — | — | — | — | OO |
| | 4-11 | $ZrO(AMA)_2$ | X | OO | OO | OO | OO | OO | OO |
| | 4-12 | $(n-C_3H_7O)_2Zr(AMA)_2$ | X | X | X | OO | OO | O | OO |
| | 4-13 | $(n-C_3H_7O)_2[ZrO(AMA)_2]_n$ | — | — | — | — | — | — | OO |

TABLE 7-continued

|  |  | Compound Formula/Abbreviation | Solubility (dissolution method) | | | | | | |
|---|---|---|---|---|---|---|---|---|---|
|  |  |  | Water | Methanol | Acetonitrile | Acetone | THF | Ethyl acetate | Toluene |
|  | 4-14 | $(i-C_3H_7O)_2Ti(AMA)_2$ | X | ○○ | ○○ | ○○ | ○○ | ○○ | ○○ |
|  | 4-15 | $(i-C_3H_7O)_2[TiO(AMA)_2]_n$ | — | — | — | — | — | — | ○○ |
|  | 4-16 | $La(AMA)_3$ | — | — | — | — | ○○ | — | ○ |
|  | 4-17 | $Eu(AMA)_3$ | — | — | — | — | ○○ | — | ○ |
|  | 4-18 | $Er(AMA)_3$ | — | — | — | — | ○○ | — | ○ |
|  | 4-19 | $(C_2H_5O)_2Nb(AMA)_3$ | — | — | — | — | — | — | ○○ |
|  | 4-20 | $Ag(AMA)$ | X-Δ | X | X-Δ | X | X | X | X |
|  | 4-21 | $Cu(AMA)_2$ | — | — | — | — | ○○ | — | — |
|  | 4-22 | $Cu(AMA)_1(AA)_1$ | — | — | — | — | ○○ | — | — |
|  | 4-23 | $Cr(AMA)_3$ | — | — | — | — | — | — | ○○ |
|  | 4-24 | $Ni(AMA)_1(MAA)_1$ | — | — | — | — | — | — | ○○ |
|  | 4-25 | $Fe(AMA)_3$ | — | — | — | — | — | — | ○○ |
|  | 4-26 | $Fe(AMA)_2(AA)_1$ | — | — | — | — | — | — | ○○ |
|  | 4-27 | $Mn(AMA)_2$ | — | — | — | — | — | — | ○○ |
|  | 4-28 | $Co(AMA)_2$ | — | — | — | — | — | — | ○○ |
| Comparative Example | 4-1 | NPGDA | X | ○○ | ○○ | ○○ | ○○ | ○○ | ○○ |
|  | 4-2 | DEGDA | X-Δ | ○○ | ○○ | ○○ | ○○ | ○○ | ○○ |
|  | 4-3 | TMPTA | X | ○○ | ○○ | ○○ | ○○ | ○○ | ○○ |
|  | 4-4 | NPG-AMA | X | ○○ | ○○ | ○○ | ○○ | ○○ | ○○ |
|  | 4-5 | DEG-AMA | X | ○○ | ○○ | ○○ | ○○ | ○○ | ○○ |
|  | 4-6 | TMP-AMA | X | ○○ | ○○ | ○○ | ○○ | ○○ | ○○ |
|  | 4-7 | $Zn(AA)_2$ | ○○ | ○○ | X-Δ | Δ | ○ | X | X |
|  | 4-8 | $Zn(Oc)_2$ | X | ○○ | X | ○○ | ○○ | ○○ | ○○ |
|  | 4-9 | $Zr(CEA)_3$ | X | ○○ | X | X | X | X | X |

The solubility evaluation by the dissolution method requires complicated operations and a large amount of test sample. Therefore, this test is not suitable for screening. However, the solubility of each compound can be more accurately evaluated. Accordingly, the solubility evaluation by dissolution method is preferably carried out on the compounds that tend to cure and be less soluble in a solvent under the film-forming conditions of the solubility evaluation in the film-forming method (e.g. $Al(AMA)_3$, $(n-C_3H_7O)_2Zr(AMA)_2$, $(i-C_3H_7O)_2Ti(AMA)_2$, and $(C_2H_5O)_2Nb(AMA)_3$), and on the compounds requiring precise solubility data.

The symbol "-" in Table 7 indicates that the test was not carried out.

Radical Curability Test on Each Compound

Examples 5-1 to 5-25, Comparative Examples 5-1 to 5-9

Radical curability test was carried out on the compounds whose film-forming ability was evaluated as "Δ" or better shown in Table 8. Each compound was applied to a glass plate to form a film in the same manner as in the film-forming test, except that 1-hydroxycyclohexyl phenyl ketone as a photoradical initiator (amount: 3% based on the amount of the compound) was added before the application solution was prepared.

The glass plate with a film was irradiated with UV light using a belt conveyer type UV irradiator in the atmosphere. The UV curability was evaluated by the number of passes until the surface of the film did not have a mark when the surface was pressed with a finger. A film whose surface still had a mark of the finger even after 25 passes was evaluated as "x". Table 8 shows the results.

The details of the belt conveyer type UV irradiator used in the test are as follows:
UV irradiation equipment: Light Hammer 6
Belt conveyer equipment: Model LC-6B Both are products of Fusion UV Systems, Inc.

Conditions of UV irradiation are as follows:

Light source: H valve

Illuminance at a wave length of 365 nm: 200 mW/cm$^2$

Fastest speed: 6.0 m/s

Irradiation time for each pass: 1 second

Accumulated amount of light for each pass: 200 mJ/cm$^2$

TABLE 8

|  | No. | Formula/ Abbreviation | Result | |
|---|---|---|---|---|
|  |  |  | Number of posses | Note |
| Example | 5-1 | $Zn(AMA)_2$ | 3 |  |
|  | 5-2 | $Zn(MAMA)_2$ | 3 |  |
|  | 5-3 | $(C_2H_5)_3NH(AMA)$ | 1 |  |
|  | 5-4 | $Ba(AMA)_2$ | 1 |  |
|  | 5-5 | $Bi(AMA)_3$ | 1 |  |
|  | 5-6 | $(CH_3)_2Sn(AMA)_2$ | 5 |  |
|  | 5-7 | $(CH_3)_2Sn(AMA)_1(MAA)_1$ | 6 |  |
|  | 5-8 | $Al(AMA)_3$ | 1 |  |
|  | 5-9 | $In(AMA)_2(MAA)_1$ | 1 |  |
|  | 5-10 | $ZrO(AMA)_2$ | 1 |  |
|  | 5-11 | $(n-C_3H_7O)_2Zr(AMA)_2$ | 1 |  |
|  | 5-12 | $(n-C_3H_7O)_2[ZrO(AMA)_2]_n$ | 1 |  |
|  | 5-13 | $(i-C_3H_7O)_2Ti(AMA)_2$ | 1 |  |
|  | 5-14 | $(i-C_3H_7O)_2[TiO(AMA)_2]_n$ | 1 |  |
|  | 5-15 | $La(AMA)_3$ | 1 |  |
|  | 5-16 | $Eu(AMA)_3$ | 1 |  |
|  | 5-17 | $Er(AMA)_3$ | 1 |  |
|  | 5-18 | $(C_2H_5O)_2Nb(AMA)_3$ | 1 |  |
|  | 5-19 | $Au(AMA)_3$ | 5 |  |
|  | 5-20 | $Cu(AMA)_2$ | X | Although the surface was tack-free, the cured layer was soft, whereby the mark pressed with the finger remained |

TABLE 8-continued

| No. | | Formula/Abbreviation | Number of posses | Note |
|---|---|---|---|---|
| | 5-21 | Cu(AMA)₁(AA)₁ | 2 | |
| | 5-22 | Cr(AMA)₃ | 2 | |
| | 5-23 | Ni(AMA)₁(MAA)₁ | 6 | |
| | 5-24 | Fe(AMA)₃ | X | Although the surface was, tack-free, the cured layer was soft whereby the mark pressed with the finger remained |
| | 5-25 | Fe(AMA)₂(AA)₁ | 6 | |
| Comparative Example | 5-1 | NPGDA | 23 | |
| | 5-2 | DEGDA | 14 | |
| | 5-3 | TMPTA | 8 | |
| | 5-4 | NPG-AMA | 21 | |
| | 5-5 | DEG-AMA | 13 | |
| | 5-6 | TMP-AMA | 6 | |
| | 5-7 | Zn(AA)₂ | 1 | |
| | 5-8 | Zn(Oc)₂ | X | Not cured at all |
| | 5-9 | Zr(CEA)₄ | 1 | |

Pencil Hardness of Cured Material

Examples 6-1 to 6-16, Comparative Examples 6-1 to 6-7

Each compound shown in Table 9 was applied to a glass plate to form a UV-cured film in the same manner as in the radical curability test, except that UV light was irradiated for 25 passes (accumulated amount of light: 5 J/cm²). The UV-cured film was subjected to scratch hardness measurement (pencil method) based on JIS K 5600-4. Table 9 shows the results.

In Table 9, the test substance of Example 6-2 is indicated as a mixture of Zn (AMA)₂ and Zn (AA)₂ because the application solution was prepared by mixing Zn (AMA)₂ and Zn (AA)₂ with a molar ratio of 1/3 to form a cured film. However, the substance was substantially a complex zinc salt of AMA⁻ and AA⁻ at a molar ratio of 1/3.

TABLE 9

| No. | | Formula/Abbreviation | Evaluation | Note |
|---|---|---|---|---|
| Example | 6-1 | Zn(AMA)₂ | 5 H | |
| | 6-2 | Zn(AMA)₂/Zn(AA)₂ = 1/3 mixture (molar ratio) | 8 H | Mixed solvent of toluene and methanol was used as the solvent for the application liquid |
| | 6-3 | Zn(MAMA)₂ | 5 H | |
| | 6-4 | Ba(AMA)₂ | 3 H | |
| | 6-5 | Bi(AMA)₃ | 3 H | |
| | 6-6 | (CH₃)₂Sn(AMA)₂ | 3 H | |
| | 6-7 | Al(AMA)₃ | 9 H | Also excellent in scratch resistance and anti-fingerprint property |
| | 6-8 | In(AMA)₂(MAA)₁ | 5 H | |
| | 6-9 | ZrO(AMA)₂ | 8 H | |
| | 6-10 | (i-C₃H₇O)₂Ti(AMA)₂ | 3 H | |
| | 6-11 | La(AMA)₃ | 4 to 5 H | |
| | 6-12 | Eu(AMA)₃ | 5 H | |
| | 6-13 | Er(AMA)₃ | 9 H | Also excellent in scratcresistance and anti-fingerprint property |
| | 6-14 | (C₂H₅O)₂Nb(AMA)₃ | 3 H | |
| | 6-15 | Cr(AMA)₃ | 7 H | |
| | 6-16 | Ni(AMA)₁(MAA)₁ | HB | |
| Comparative Example | 6-1 | NPGDA | 3 H | |
| | 6-2 | DEGDA | 2 H | |
| | 6-3 | TMPTA | 4 to 5 H | |
| | 6-4 | NPG-AMA | 2 H | |
| | 6-5 | DEG-AMA | 2 H | |
| | 6-6 | TMP-AMA | 4 H | |
| | 6-7 | Zr(CEA)₄ | 3 H | |

Table 9 shows that the salt of a diene carboxylic acid of the claimed invention can form high-density crosslinking by ionic bonds with a metal ion, which enables to form a film with a high hardness. In particular, a cured film formed from an aluminum salt or an erbium salt not only has transparency and high pencil hardness, but also is excellent in scratch resistance and an anti-fingerprint property. Accordingly, the film may be suitably used for applications such as high-performance hard coating materials.

Refractive Index of Cured Material

Examples 7-1 to 7-7, Comparative Examples 7-1 to 7-7

Each compound shown in Table 10 was mixed with 1-hydroxycyclohexyl phenyl ketone in an amount of 3% based on the compound, and optionally an appropriate solvent in an amount such that the compound concentration was 20% to 40%, and thereby an application solution was prepared. The application solution was filtered through a filter with pores each of which has the size of 0.45 μm. Then, the application solution was applied to a silicon wafer using a spin coater with the spinning speed adjusted such that the dried film thickness was about 3 μm. The application solution was dried in a vacuum dryer at 80° C. for 10 minutes, and then exposed to UV light for 25 passes in the same manner as in the pencil hardness test. Thereby, a measurement sample, in which a cured film was formed on a silicon wafer, was obtained.

The refractive index in TE mode and the refractive index in TM mode of the measurement sample were measured by a prism coupler (SPA-4000, Sairon Technology) with a light source having a wave length of 633 nm. The average value of the two refractive indexes was determined as the refractive index of the cured material of the compound. Table 10 shows the results.

TABLE 10

| No. | | Formula/Abbreviation | Refractive index |
|---|---|---|---|
| Example | 7-1 | Zn(AMA)₂ | 1.548 |
| | 7-2 | Ba(AMA)₂ | 1.553 |
| | 7-3 | (CH₃)₂Sn(AMA)₂ | 1.541 |
| | 7-4 | In(AMA)₂(MAA)₁ | 1.558 |
| | 7-5 | ZrO(AMA)₂ | 1.584 |
| | 7-6 | (i-C₃H₇O)₂Ti(AMA)₂ | 1.621 |
| | 7-7 | La(AMA)₃ | 1.561 |

TABLE 10-continued

| No. | | Formula/Abbreviation | Refractive index |
|---|---|---|---|
| Comparative Example | 7-1 | NPGDA | 1.491 |
| | 7-2 | DEGDA | 1.484 |
| | 7-3 | TMPTA | 1.515 |
| | 7-4 | NPG-AMA | 1.511 |
| | 7-5 | DEG-AMA | 1.514 |
| | 7-6 | IMP-AMA | 1.522 |
| | 7-7 | Zr(CEA)$_4$ | 1.553 |

Comparison of the results of Examples 7-1 to 7-7 and of Comparative Examples 7-1 to 7-6 in Table 10 shows that introduction of a metal ion improves the refractive index. Also, comparison of the results of Example 7-5 and of Comparative Example 7-7, both being a polymerizable metal salt containing zirconium, shows that the salt of a diene carboxylic acid of the claimed invention can have a higher metal content, and thus more improve the refractive index.

Adhesion of Cured Material

Examples 8-1 to 8-3, Comparative Examples 8-1 to 8-5

Each compound shown in Table 11 was formed into a UV-cured film on a PET film in the same manner as in the pencil hardness test, except that the PET film used as a substrate was a surface-untreated polyethylene terephthalate (PET) film (Lumirror L-50T60, produced by Toray Industries, Inc.).

The adhesion of the UV-cured film to the PET film was evaluated based on JIS K 5600-5-6 (cross-cut method). The number of divided segments was 10×10 segments=100 segments. The adhesion was evaluated by the number of the segments which remain without peeling or damage in 100 segments. Table 11 shows the results.

TABLE 11

| No. | | Formula/Adhesion | Abbreviation |
|---|---|---|---|
| Example | 8-1 | Zn(AMA)$_2$ | 100/100 |
| | 8-2 | Al(AMA)$_3$ | 100/100 |
| | 8-3 | ZrO(AMA)$_2$ | 100/100 |
| Comparative Example | 8-1 | NPGDA | 49/100 |
| | 8-2 | DEGDA | 32/100 |
| | 8-3 | TMPTA | 71/100 |
| | 8-4 | NPG-AMA | 72/100 |
| | 8-5 | DEG-AMA | 85/100 |

Table 11 shows that the salt of a diene carboxylic acid of the claimed invention also shows excellent adhesion to surface-untreated PET. Accordingly, the salt may be suitably used as a UV-curable undercoat agent for improving the adhesion of various difficult-to-adhere resin films such as a surface-untreated PET film.

Light Transmittance of Cured Material

Examples 9-1 to 9-7, Comparative Example 9-1

For each compound shown in Table 12, a sample for measurement having a UV-cured film of each compound formed on an alkali-free glass plate was prepared in the same manner as the measurement sample of refractive index, except that a 2-inch square alkali-free glass plate was used as a substrate.

The transmittance of the measurement sample at a wave length of 200 to 1,500 nm was measured using a spectrophotometer (UV-3100, produced by Shimadzu Corporation) with an alkali-free glass plate identical to the substrate set as a reference. After the transmittance measurement, part of the cured film was scraped off with a spatula, and the film thickness of the scraped part was measured with a stylus surface profilometer (Dektak 3030, produced by Sloan). Table 12, and FIGS. 20-1 to 20-4 and 21-1 to 21-4 show the results.

The test sample of Example 9-7 is indicated as a mixture of La (AMA)$_3$ and Cu (AMA)$_2$ in the table because the cured film was formed from an application solution containing La (AMA)$_3$ and Cu (AMA)$_2$ at a molar ratio of 1/2. However, the test sample was substantially a complex salt of AMA$^-$, La$^{3+}$, and Cu$^{2+}$ at a molar ratio of 7/1/2.

TABLE 12

Figure 3:
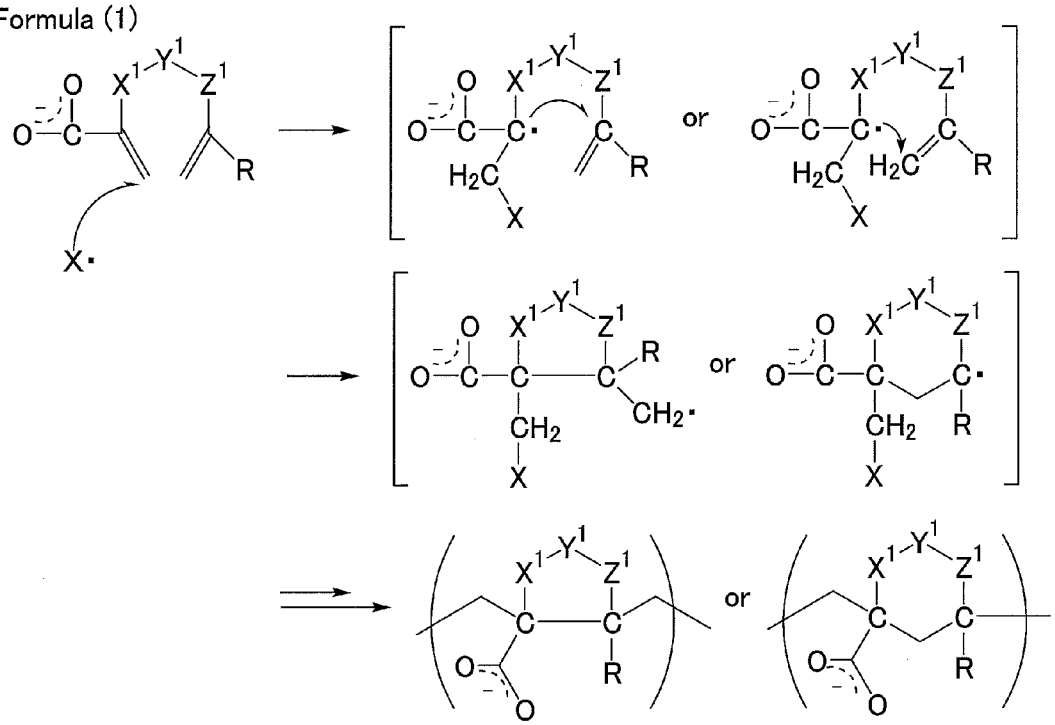
FIG. 3(ii) shows a schematic diagram of the cyclic polymerization mechanism of a diene carboxylate anion represented by Formula (2).
Figure 3:
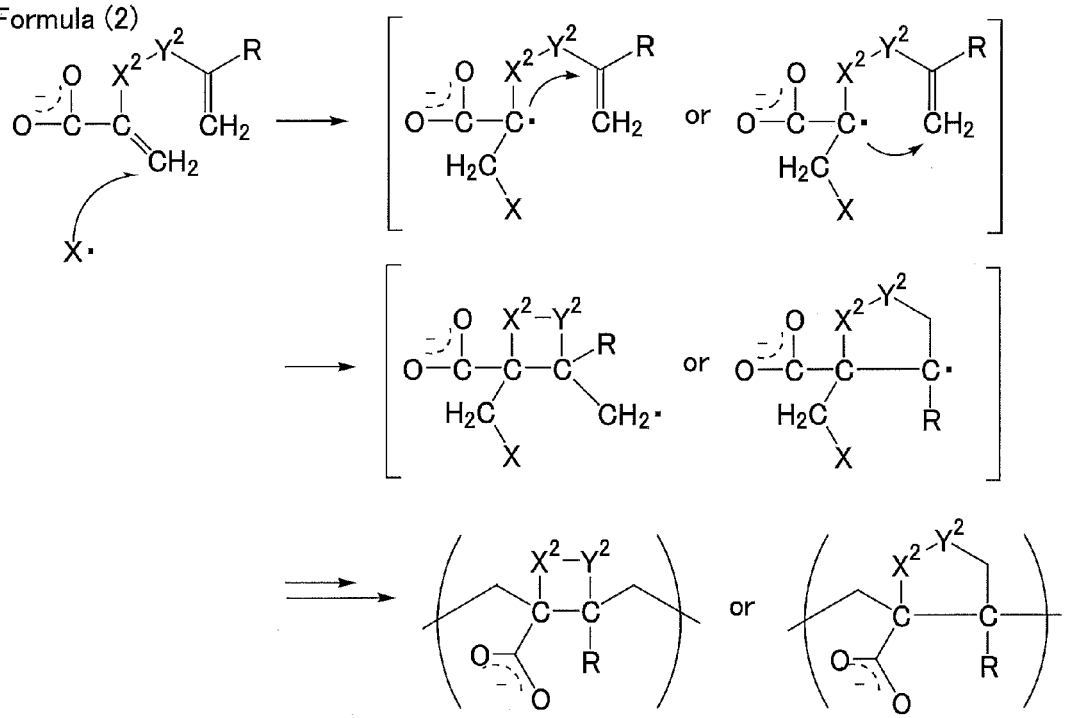
Figure 4:
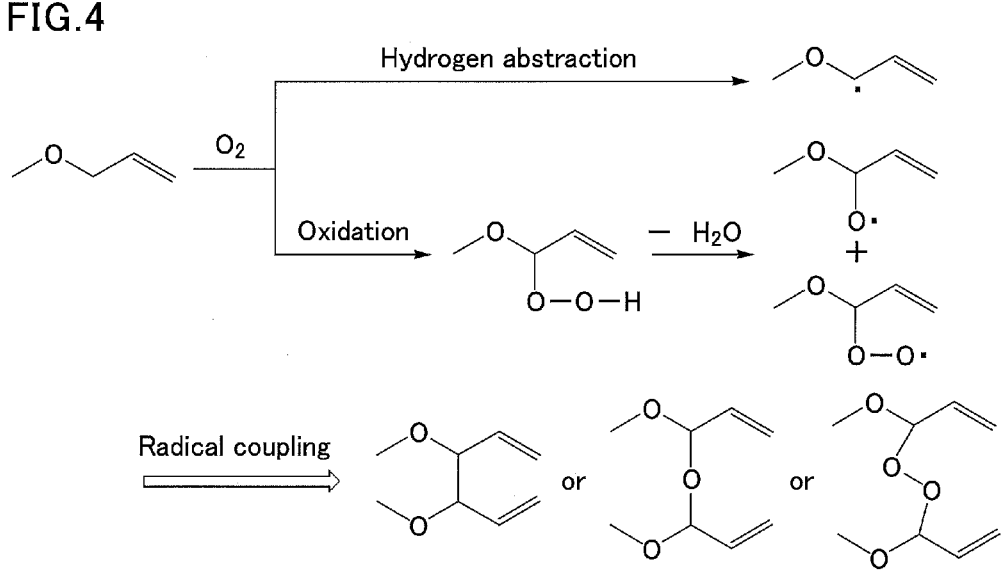
FIG. 4 shows a schematic diagram of the curing mechanism of an alkyl allyl ether compound.
Figure 5:
FIG. 5 shows the structures of a diene acyl group included in the diene carboxylate anion of the claimed invention.
Figure 6:
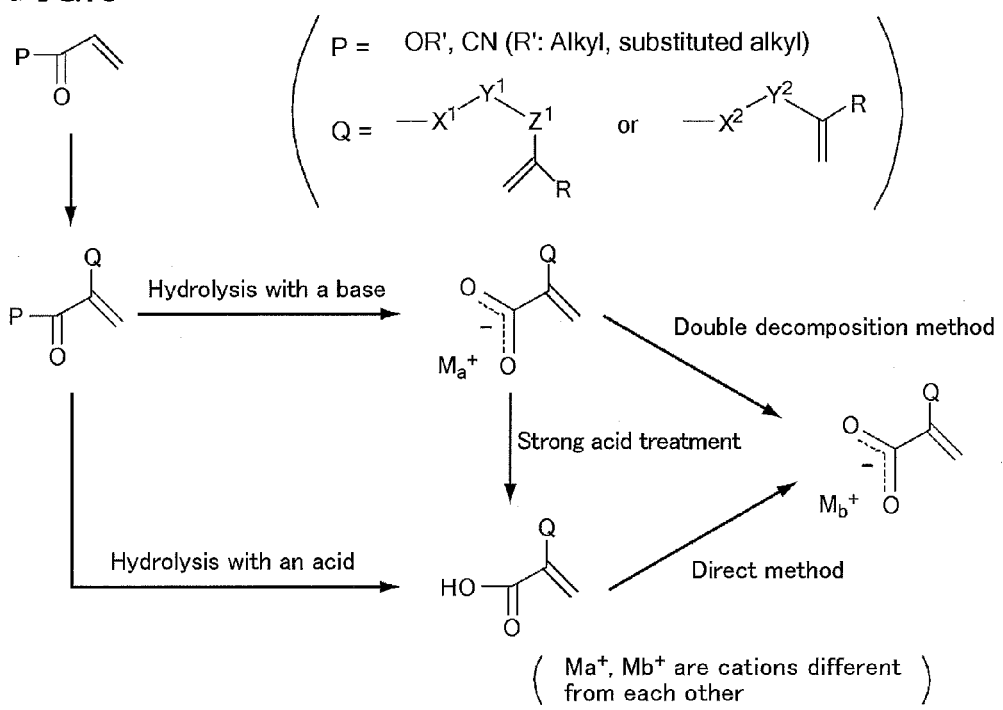
FIG. 6 shows an outline of the reaction path of the method for producing the diene carboxylate anion of the claimed invention.
Figures 1, 20:
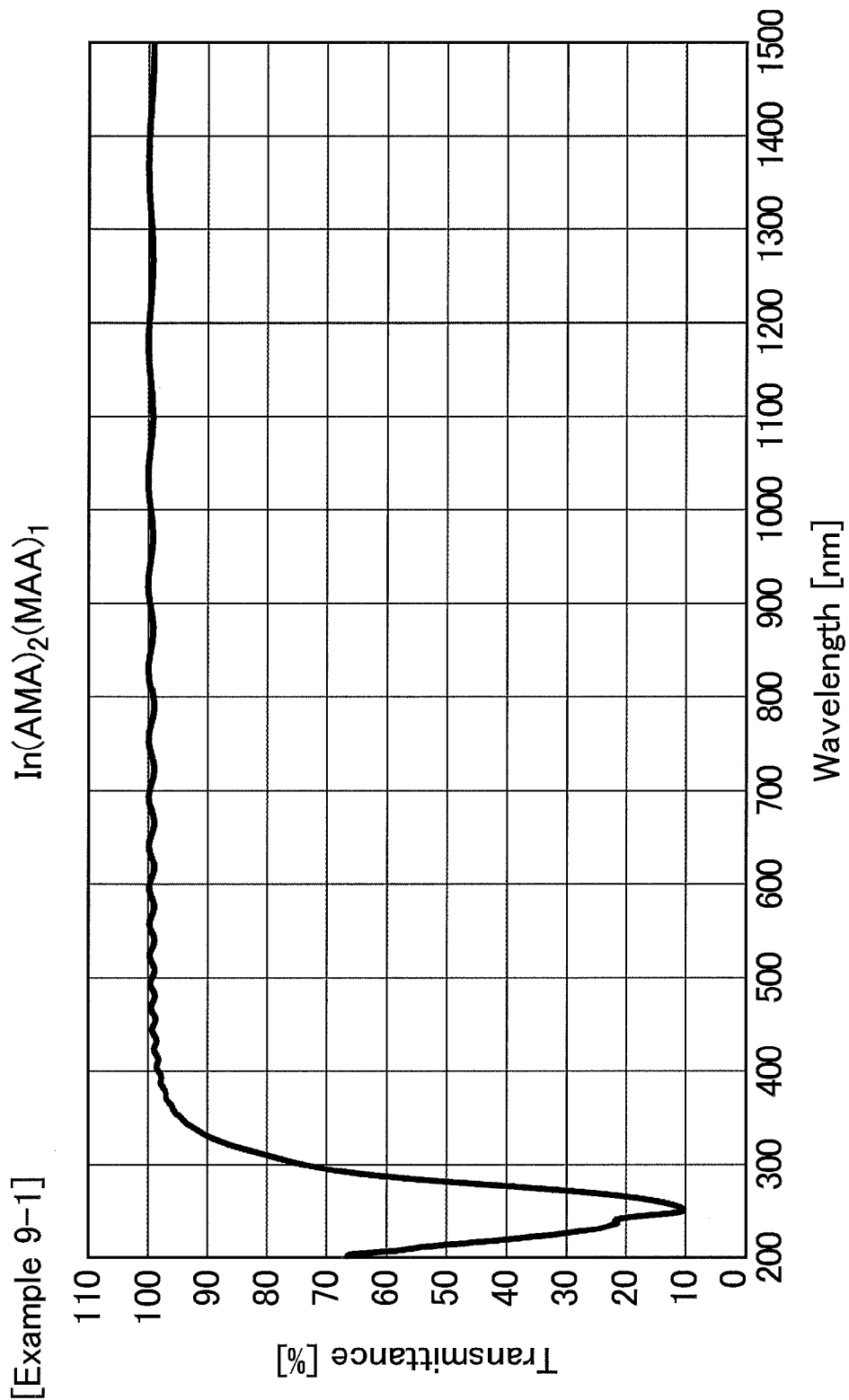
Figures 2, 20:
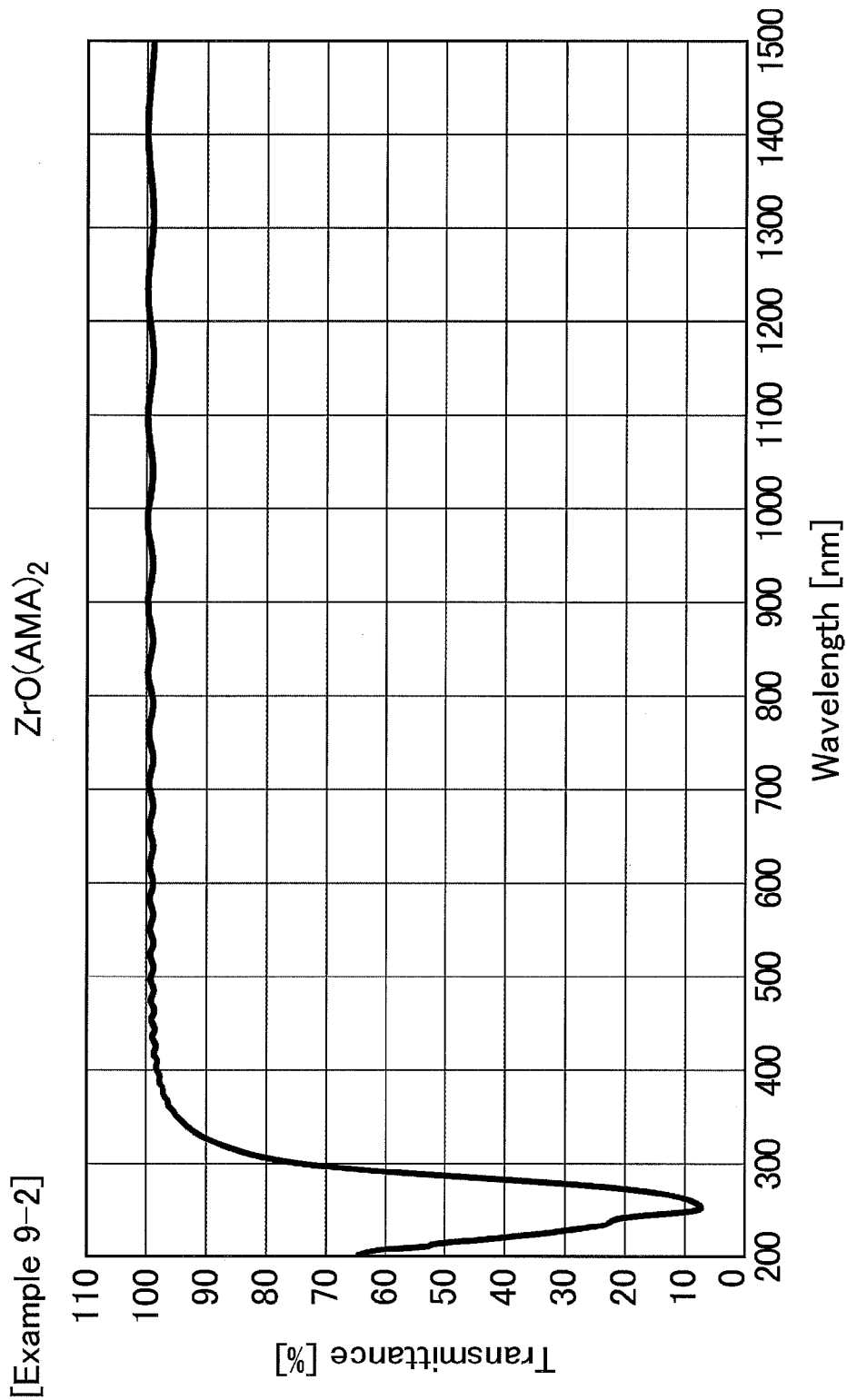
Figures 3, 20:
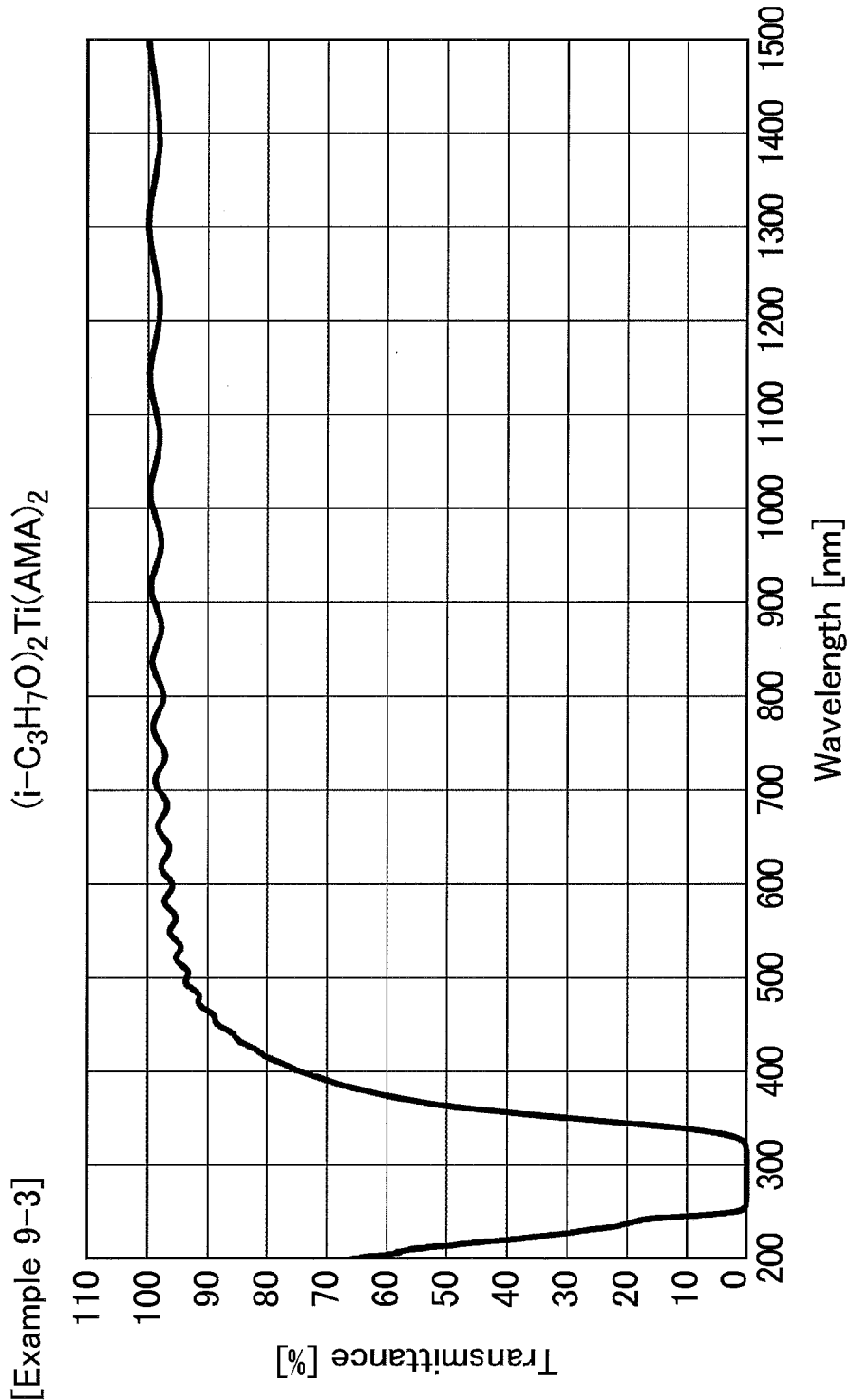
Figures 4, 20:
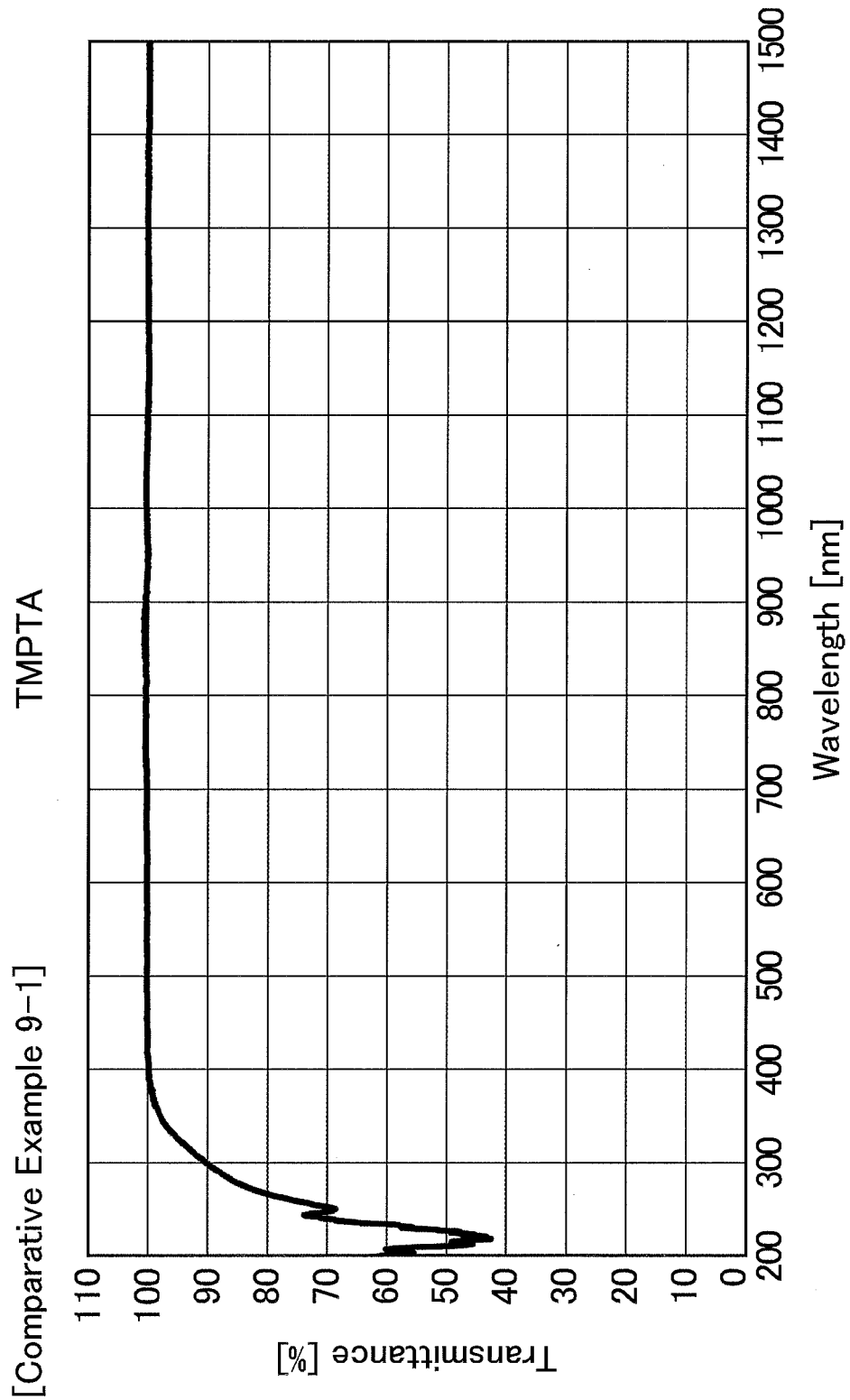
Figures 1, 21:
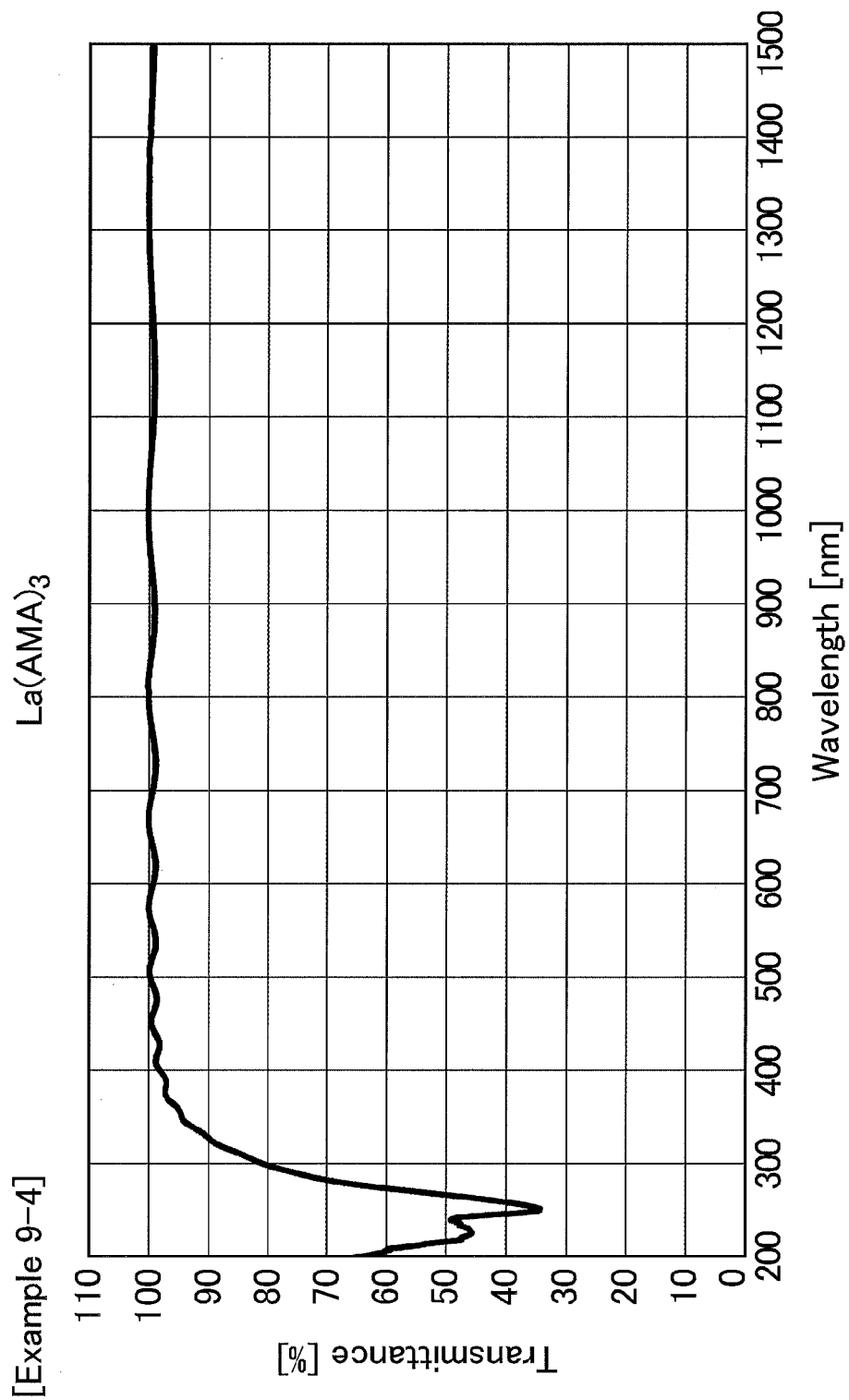
Figures 2, 21:
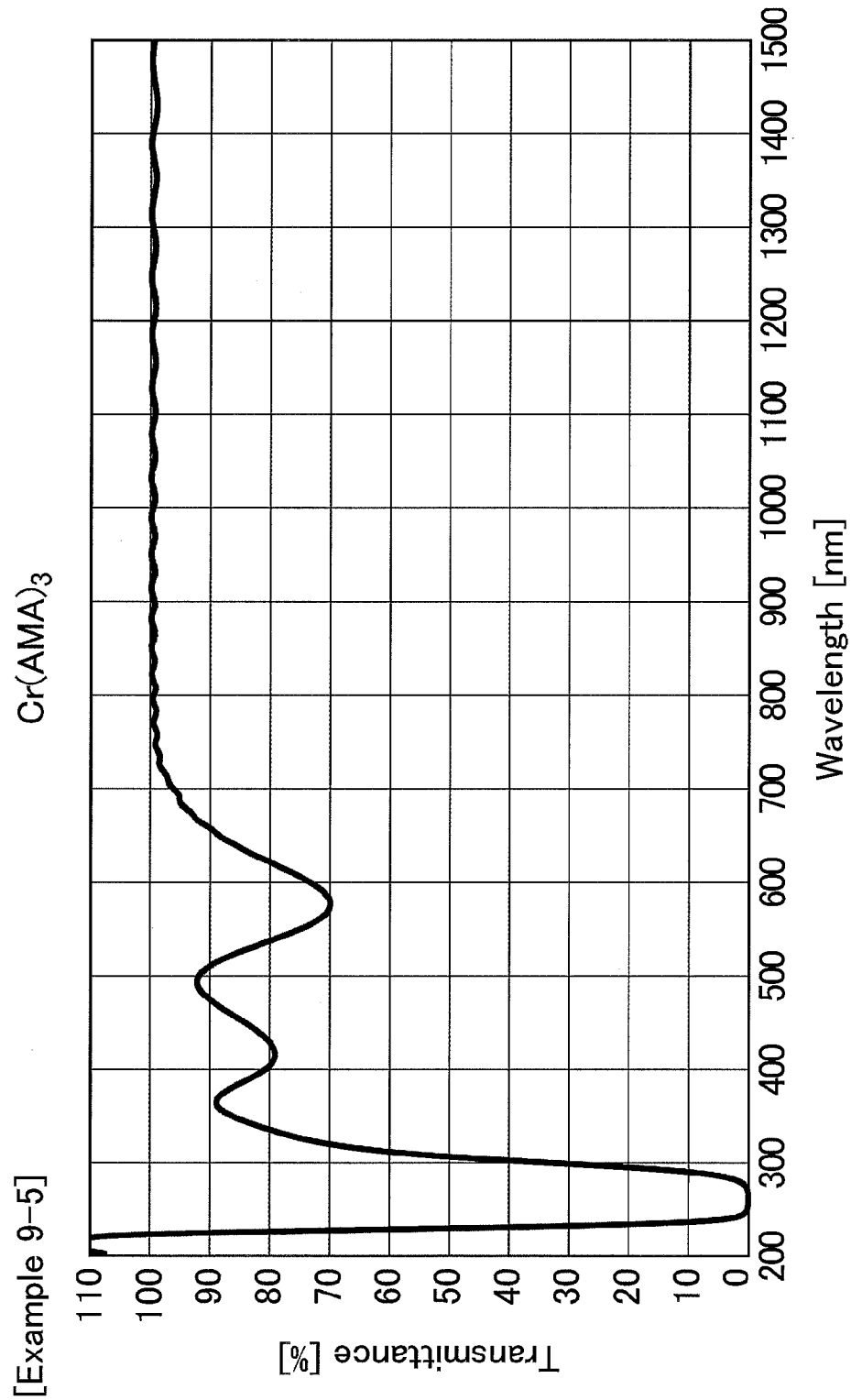
Figures 3, 21:
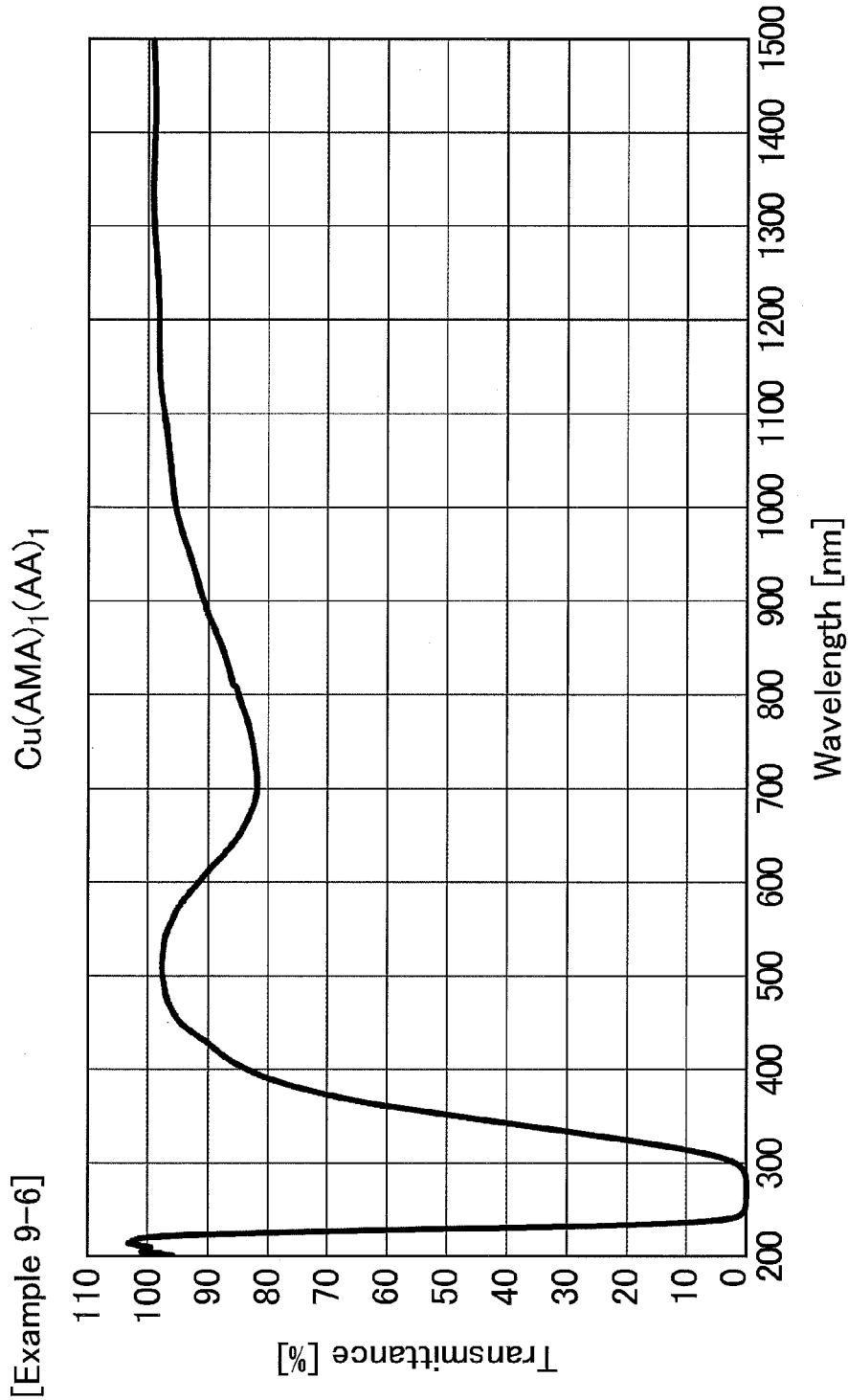
Figures 4, 21:
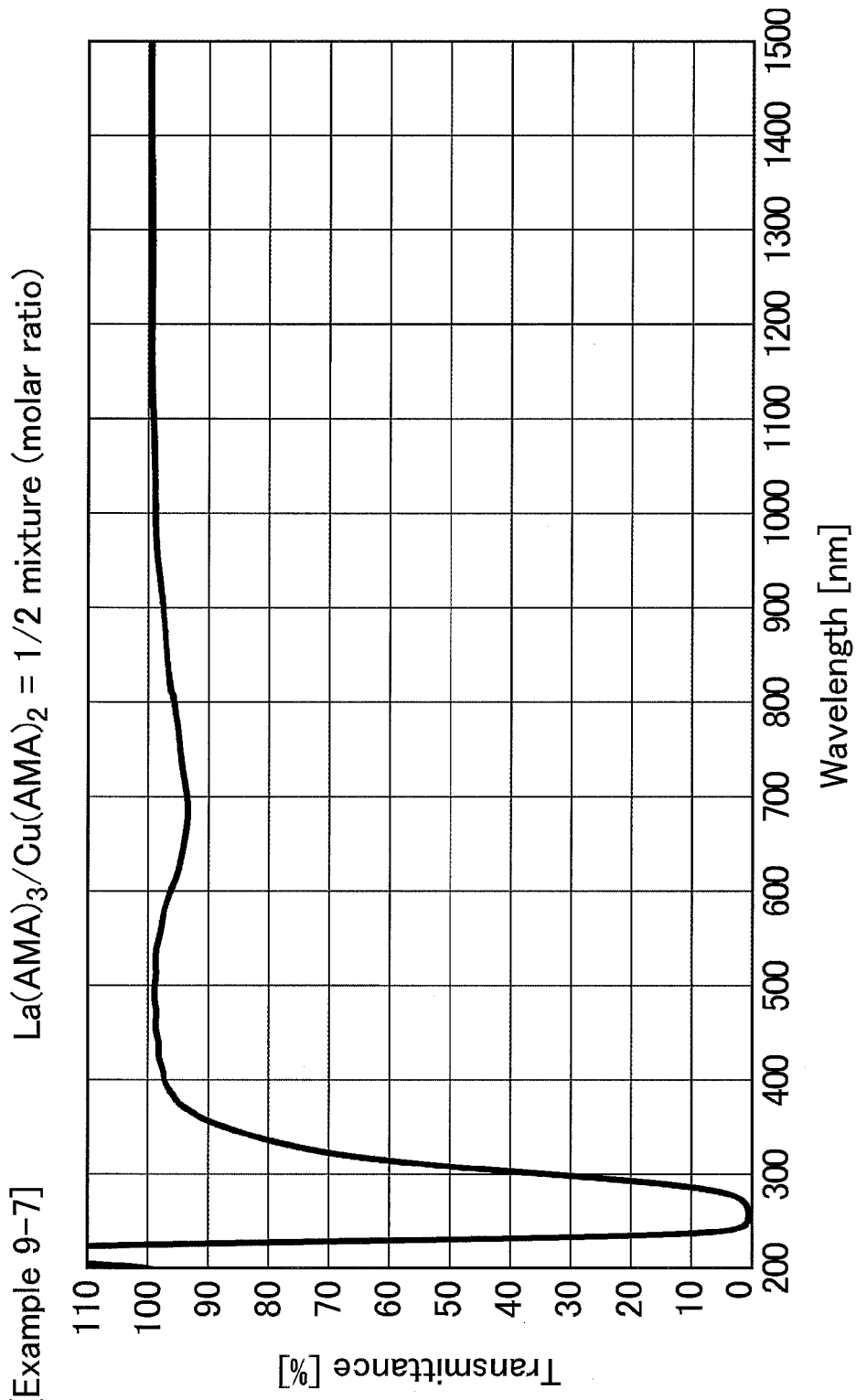

| No. | | Formula/Abbreviation | Film thickness [μm] | Measurement results of transmittance |
|---|---|---|---|---|
| Example | 9-1 | In(AMA)$_2$(MAA)$_1$ | 2.6 | FIG. 20-1 |
| | 9-2 | ZrO(AMA)$_2$ | 3.1 | FIG. 20-2 |
| | 9-3 | (i-C$_3$H$_7$O)$_2$Ti(AMA)$_2$ | 2.8 | FIG. 20-3 |
| | 9-4 | La(AMA)$_3$ | 2.1 | FIG. 21-1 |
| | 9-5 | Cr(AMA)$_3$ | 4.3 | FIG. 21-2 |
| | 9-6 | Cu(AMA)$_1$(AA)$_1$ | 2.2 | FIG. 21-3 |
| | 9-7 | La(AMA)$_3$/Cu(AMA)$_2$ = ½ Mixture (molar ratio) | 1.7 | FIG. 21-4 |
| Comparative Example | 9-1 | TMPTA | 3.0 | FIG. 20-4 |

The results shown in Table 12, and FIGS. 20-1 to 20-4 and 21-1 to 21-4 show the following. The compounds of Examples 9-1 to 9-3 and Comparative Example 9-1 show high absorption in the UV region because of introduction of a metal ion. Accordingly, these compounds can be used for applications such as UV protection materials. The compounds of Examples 9-5 to 9-7 show absorption in the vicinity of 600 to 700 nm as well as the UV region. Accordingly, these compounds can be used for applications such as blue colorants and IR protection materials. The compound of Example 9-7 (a complex salt of copper and lanthanum) can change the color characteristics (change the shape of the light transmittance spectrum) from slightly greenish blue in the case of containing only a copper ion (Example 9-6) to brilliant blue in the case of complexing a copper ion with another metal cation (lanthanum), by improving the transmittance in the vicinity of 400 to 450 nm. In addition, even a metal salt (Cu (AMA)$_2$) with a low UV curability can show excellent UV curability by complexing with a metal salt (La (AMA)$_3$) with a high UV curability. Therefore, the compositions evaluated as having a low UV curability in the UV curability test may also be used as highly UV curable materials.

Oxygen Gas-Barrier Property of Cured Material

Examples 10-1 and 10-2, Comparative Example 10-1

Each compound shown in Table 13 was formed into a UV-cured film on a PET film in the same manner as in the adhesion test. The film was placed in a cell of an oxygen transmission rate tester (Model 8001, produced by Illinois Instruments) such that the UV-cured film faced the bottom side (the side of nitrogen flow), and the oxygen transmission rate (OTR) [cc/m²·day] was measured in the following conditions:

Oxygen flow=20 [cc/min]
Nitrogen flow=20/10 [cc/min]
Test temperature: 23° C.

Figure 22:
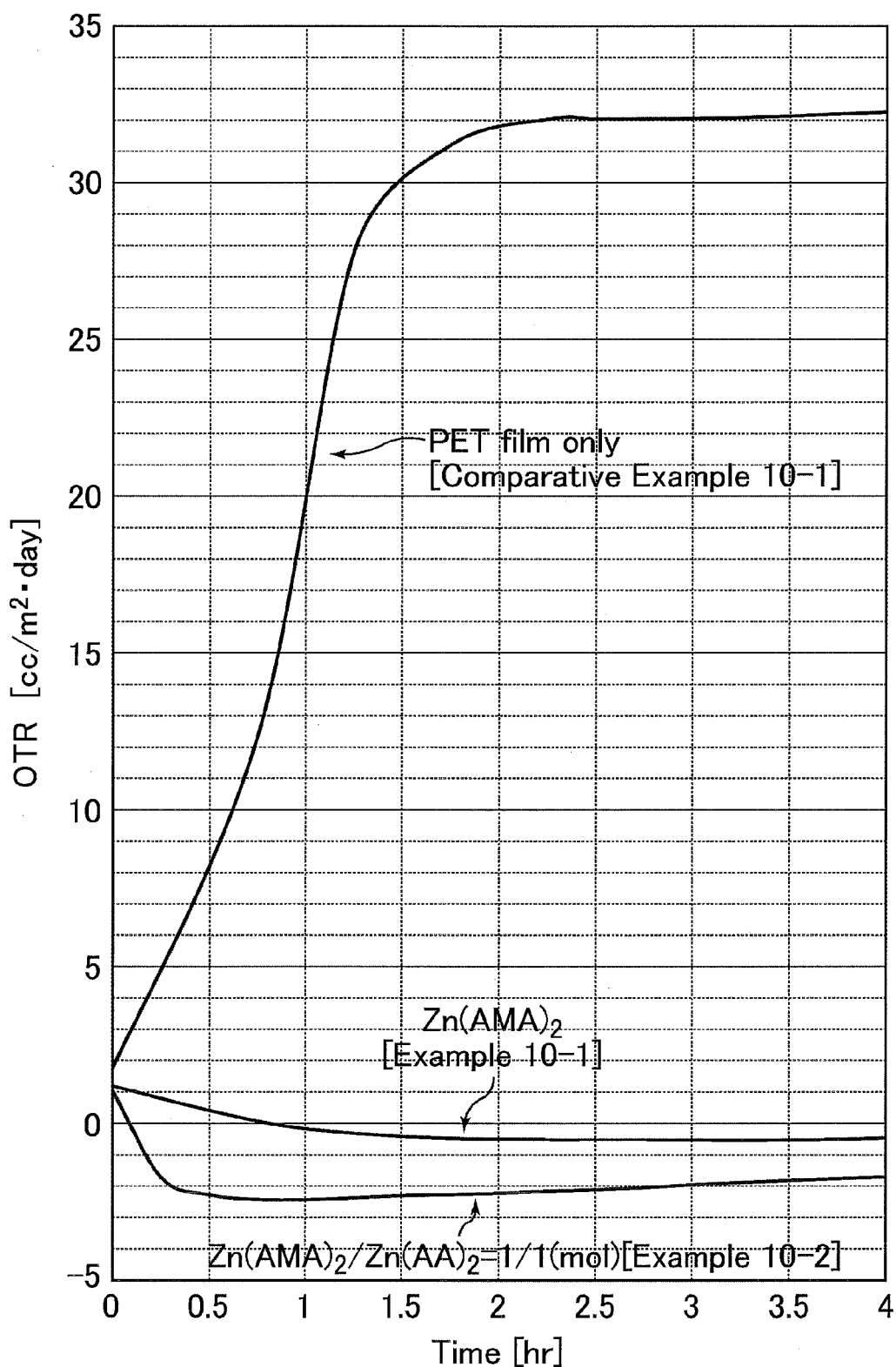
FIG. 22 shows a graph of the change with time of the oxygen transmission rate in Examples 10-1 and 10-2 and in Comparative Example 10-1.

The value after 2.5 hours from the start of the test, at which the measured value was stable, was determined as the OTR value of the test. Table 13 and FIG. 22 show the results.

In Example 10-2, the test sample is indicated as a mixture of Zn (AMA)$_2$ and Zn (AA)$_2$ in the table because the cured film was formed from an application solution containing Zn(AMA)$_2$ and Zn (AA)$_2$ at a molar ratio of 1/1. However, the test sample was substantially a complex zinc salt of AMA$^-$ and AA$^-$ at a molar ratio of 1/1.

TABLE 13

| No. | | Formula/Abbreviation | Oxygen transmission rate [cc/m² • day] |
|---|---|---|---|
| Example | 10-1 | Zn(AMA)$_2$ | −0.54 |
| | 10-2 | Zn(AMA)$_2$/Zn(AA)$_2$ = ¹/₁ Mixture (molar ratio) | −2.14 |
| Comparative Example | 10-1 | None (PET film only) | 32.0 |

The results in Table 13 and FIG. 22 show that the negative OTR values in the examples mean that the compositions of the examples not only prevent transmission of oxygen gas by a passive mechanism but also chemically absorb oxygen by an active mechanism. The oxygen absorption by an active mechanism derives from the diene carboxylate anion of the claimed invention. Accordingly, oxygen is particularly efficiently absorbed in the case that $Z^1$ of Formula (1) or $Y^2$ of Formula (2) in the diene carboxylate anion of the claimed invention is a methylene group, in other words, the diene carboxylate anion includes a (meth)ally group in the structure, and particularly preferably in the case that the anion thereof is α-(meth)allyloxymethyl carboxylate anion. Therefore, a salt of the diene carboxylate anion of the claimed invention is suitable for applications requiring particularly strict oxygen barrier properties, and may be used for various applications by selecting an appropriate counter cation. For example, a salt of an antifungal or bactericidal counter cation (such as a zinc ion, a silver ion, a copper ion, and an ammonium ion) can be suitably used for adhesives, tackifiers, coating agents, and wrapping materials of foods and drugs, and a salt of a counter cation (such as an aluminum ion and a zirconium ion) that chemically absorbs moisture can be suitably used for wrapping materials, sealing materials, adhesives, and the like of elements and parts that are required to avoid not only oxygen but also moisture (e.g. organic EL).

Fluorescent Color Developability of Cured Material

Example 11

A 10-ml screw-cap tube containing a toluene solution of Eu(AMA)$_3$ was prepared. To the screw-cap tube was added 1-hydroxycyclohexyl phenyl ketone in an amount of 3% based on Eu(AMA)$_3$, and 1-hydroxycyclohexyl phenyl ketone was dissolved in the solution so that the mixture was uniform and transparent. Then, the mixture was dried in a vacuum dryer at 80° C. for one hour, whereby toluene was removed.

The screw-cap tube was exposed to UV irradiation (5 J/cm²) for 25 passes with a belt conveyer type UV irradiator, so that the product therein was cured.

Figure 23:
FIG. 23 is a photograph showing that the cured material of $Eu(AMA)_3$ develops a fluorescent color in Example 11.

The screw-cap tube with a cured material of Eu(AMA)$_3$ was irradiated with UV light at a wave length of 365 nm in a dark place. Thereby, the cured material developed a fluorescent color of pink to red. FIG. 23 shows the color development. In FIG. 23, an outside part of the screw-cap tube looks white because of UV light.

The result of Example 11 indicates that the characteristics of rare-earth elements (e.g. fluorescent color developability of Eu$^{3+}$) are still alive even in a UV cured material of the diene carboxylate anion of the claimed invention. Accordingly, a salt of the diene carboxylate anion of the claimed invention and a rare-earth element ion can be suitably used for applications utilizing characteristics of rare-earth elements (e.g. fluorescent color development, optical amplification), such as displays, lightings, solar cells, optical fibers, and optical circuits.

Photochromic Property of Cured Material

Example 12

To a toluene solution of Bi(AMA)$_3$ was added 1-hydroxycyclohexyl phenyl ketone in an amount of 3% based on the amount of Bi(AMA)$_3$ and 1-hydroxycyclohexyl phenyl ketone was dissolved in the solution so that the mixture was uniform and transparent. The resulting mixture was, in the same manner as in the pencil hardness test, applied to a glass plate with a bar coater such that the film thickness was about 2.5 μm, and dried in a vacuum dryer at 80° C. for 10 minutes.

The glass plate was almost colorless and transparent at this uncure state, however, the color thereof was gradually changed into yellowish brown as UV irradiation (250 mJ/cm²/time) with the belt conveyer type UV irradiator was repeated, and finally became dark brown after 25 passes of the irradiation.

The color of the glass plate turned transparent pale yellow after being left to stand at room temperature overnight. The light transmittance of the glass plate at this state was measured with the spectrophotometer with an alkali-free glass plate identical to the substrate set as a reference. The glass plate was half covered with aluminum foil and exposed to UV irradiation for 25 passes with the belt conveyer type UV irradiator. Thereby, only the part without the aluminum foil cover turned dark brown again. The light transmittance of this dark brown part was measured in the above manner. The dark brown part turned back to original transparent pale yellow after another night. The light transmittance of this part was measured.

Figure 24:
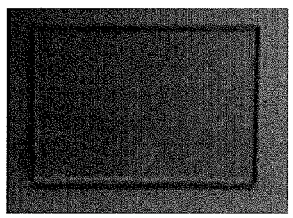
FIG. 24 shows photographs showing the reversible color change (photochromic property) of the cured material of $Bi(AMA)_3$ by UV light in Example 12, and graphs of the measurement of the light transmittance, on each stage of the change.
Figure 24:
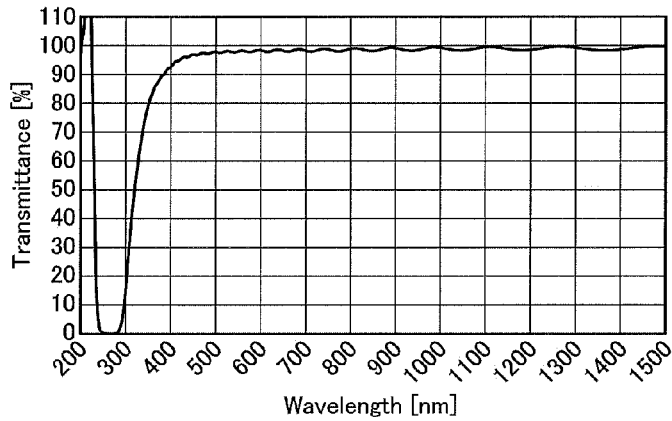
Figure 24:
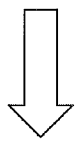
Figure 24:
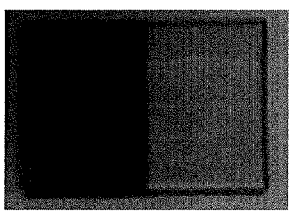
Figure 24:
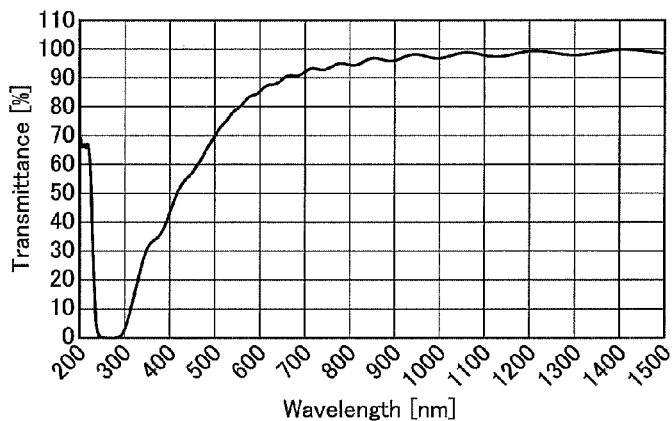
Figure 24:
Figure 24:
Figure 24:
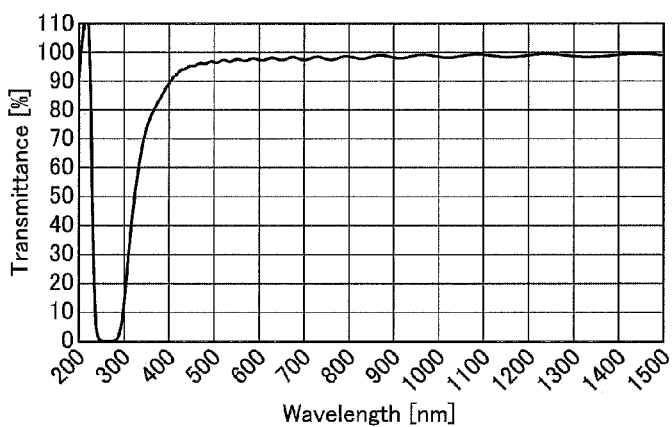

FIG. 24 shows the appearance of this reversible color change (photochromic property) by UV light and the results of light transmittance measurement. Such a phenomenon never occurs in the case of UV cured materials of esters of α-(meth)allyloxymethyl acrylic acid and α-(meth)allyloxymethyl acrylic acid.

The results of Example 12 show that a cured material containing a Bi$^{3+}$ ion and a polymerized anion of an anion of α-(meth)allyloxymethyl acrylate exerts photochromic property. For ions other than Bi$^{3+}$, appropriated selection of the kind and combination of counter cations leads to adjustment of the wavelength of the light source allowing color change, the color to be developed, and the response to light stimulus, whereby the ions can also be suitably used for applications such as lenses, displays, and optical storage materials.

Production of Metal Nanoparticle Composite Material

Example 13-1

Ag(AMA) was dissolved in H-AMA such that the silver content was 10%, and the concentration was further adjusted by diluting the solution with a small amount of acetonitrile. Then, 1-hydroxycyclohexyl phenyl ketone was added thereto in an amount of 3% based on the total amount of Ag (AMA) and H-AMA, and the mixture was stirred, whereby a colorless transparent solution was obtained. The solution was, in the same manner as in the pencil hardness test, applied to a glass plate with a bar coater such that the film thickness was about 2.5 μm, and then dried in a vacuum dryer at 80° C. for 10 minutes.

Figure 25:
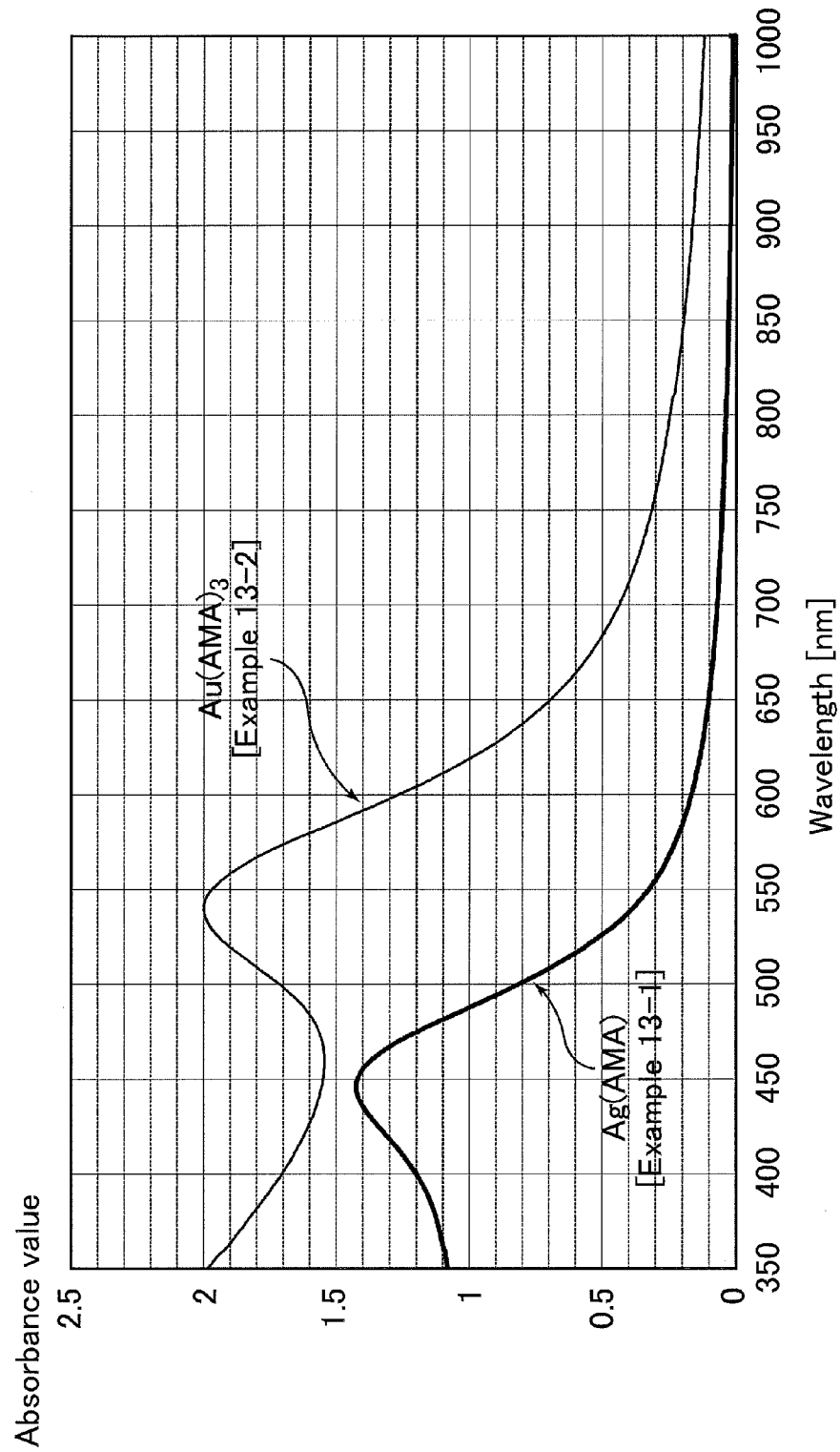
FIG. 25 shows a graph of the measurement of the absorbance values in Examples 13-1 and 13-2.

The glass plate was colorless and transparent at this uncure state, however, the color thereof was gradually changed into yellowish brown as UV irradiation (250 mJ/cm$^2$/time) with the belt conveyer type UV irradiator was repeated, and finally became dark brown after 25 passes of the irradiation. The absorbance value of the glass plate was measured with the spectrophotometer with an alkali-free glass plate identical to the substrate set as a reference. Thereby, a strong absorption derived from plasmon absorption of silver nanoparticles was observed at 446 nm, as shown in FIG. 25.

Example 13-2

The 1-butanol solution of Au(AMA)$_3$ obtained in Example 1-24 was prepared, and 1-hydroxycyclohexyl phenyl ketone was added thereto in an amount of 3% based on Au (AMA)$_3$ and the mixture was stirred. Thereby, an yellow transparent solution was obtained. The solution was, in the same manner as in the pencil hardness test, applied to a glass plate with a bar coater such that the film thickness was about 2.5 μm, and then dried in a vacuum dryer at 80° C. for 10 minutes.

The glass plate was transparent pale yellow at this uncure state, however, the color thereof was gradually changed into reddish violet as UV irradiation (250 mJ/cm$^2$/time) with the belt conveyer type UV irradiator was repeated, and finally became dark reddish violet after 25 passes of the irradiation. The absorbance value of this glass plate was measured with the spectrophotometer with an alkali-free glass plate identical to the substrate set as a reference. Thereby, a strong absorption derived from plasmon absorption of gold nanoparticles was observed at 541 nm, as shown in FIG. 25.

Example 13-3

A UV-cured layer of Au(AMA)$_3$ was formed on a PET film (Lumirror L-50T60, produced by Toray Industries, Inc.) in the same manner as in Example 13-2, except that the above PET film was used as a substrate. The resulting PET film with a cured film was dark reddish violet as in Example 13-2, and the cured film was firmly attached to the PET film. In addition, the PET film with a cured film did not cause swelling or peeling even after immersion in water for overnight.

This film had gold metallic luster on the surface (the side of the cured film) after being left to stand at room temperature in a room for two days. However, when the film was observed from the side of the back surface (the surface without the cured film), the cured film (the side adhering to the PET film, which is the side not open to the atmosphere) remained dark reddish violet.

The results of Examples 13-1 to 13-3 show that UV irradiation causes radical curing and reduction of a silver ion or a gold ion to a metal at the same time, and the composition resultantly can work as a resin material in which metal nanoparticles are uniformly contained at a high concentration. The results also show that a metallic thin film may be formed depending on the kind and the concentration of the metal, and the treating conditions such as UV curing. The same shall apply to ions of other metals (such as precious metals including platinum) which can be reduced to a metal by UV light. The reduction can be effectively caused by UV curing in the presence of a composition including a reducing substance such as an amine, an alcohol, an aldehyde, and an ammonium salt. In addition to metal nanoparticles, the resin material may also contain nanoparticles of a metal oxide depending on the kind of the metal ion, curing conditions, and the substance included in a composition used with the metal ion. The resins containing metal nanoparticles or nanoparticles of a metal oxide can be used in various applications. For example, the resins containing precious metal nanoparticles can be used for undercoat layers for plating, electrode materials, wiring materials, biosensors and biochips using plasmon absorption, color materials, and the like. Moreover, a salt of the metal ion reducible to a metal by UV light and the diene carboxylate anion of the claimed invention is useful as raw materials for micro wiring and metamaterials, when used in combination with microfabrication technology using photocuring, such as photolithography and UV nanoimprint technology.

Production of Metallic Thin Film by Firing

Example 14

A glass plate with a UV-cured mixture of Ag (AMA) and H-AMA obtained in Example 13-1 was placed in a firing furnace filled with a nitrogen atmosphere. Then, the firing furnace was heated to 400° C. under a stream of nitrogen to heat the glass plate at 400° C. for three hours. Subsequently, the firing furnace was left to stand to slowly cool to room temperature.

When the sample was taken out after cooling, a yellowish white layer was formed on the glass plate. When the yellowish white layer was pressed by a spatula, metallic luster appeared, whereby formation of a silver thin film was confirmed.

The result of Example 14 indicates that a thin film of a metal or a metal oxide can be formed by firing a cured salt containing the diene carboxylate anion of the claimed invention and a metal ion under appropriate conditions. In other words, a salt of the diene carboxylate anion of the claimed invention and a metal ion can be used as a MOD material. In addition, a microstructure made of a metal or a metal oxide can be easily obtained by firing the above salt after forming a microstructure using a simple patterning process such as photolithography, UV-curable nanoimprinting, heat-curable nanoimprinting, or direct writing by inexpensive energy beams such as visible-light laser beams or infrared laser beams.

Image Formation by Photolithography

Example 15

To a toluene solution of Zn(AMA)$_2$ was added 1-hydroxycyclohexyl phenyl ketone in an amount of 3% based on Zn(AMA)$_2$ and the mixture was stirred, whereby a colorless transparent solution was obtained. In the same manner as in production of the sample for refractive index measurement, the solution was applied to an alkali-free glass plate with a spin coater such that the film thickness was 3 μm, and then dried in a vacuum dryer at 80° C. for 10 minutes.

The glass plate was irradiated with UV light with the UV irradiator through a photomask made of an OHP film on which four letters (a, b, c, and d) each having a size of about a 5-mm square were reverse-printed in black and white. After UV irradiation, the unirradiated part was developed by sprinkling acetone from an acetone wash bottle. Then, the four letters a, b, c, and d remained on the glass plate.

The result of Example 15 indicates that a composition having film-forming ability enables image formation by a photolithography process if a composition has film-forming ability, UV curability, and solubility to some sort of solvent. The photolithography process can provide a microstructure on the order of microns by adjusting the light source, the photomask to be used, curing conditions, and developing conditions. A composition having film-forming ability and UV curability can be used for other microfabrication processes using UV curing, such as a UV nanoimprinting process and an inkjet process. The UV nanoimprinting process can provide a microstructure on the order of nanometers.

The invention claimed is:

1. A salt of a diene carboxylic acid comprising a diene carboxylate anion represented by Formula (1)

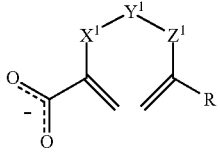

Formula (1)

wherein R represents a hydrogen atom or a methyl group; $X^1$ and $Z^1$ are the same and represent a methylene group, $Y^1$ is an oxygen atom; and oxygen-carbon-oxygen bonds shown by a dotted line and a solid line means that two carbon-oxygen bonds in each bond unit are equivalent to each other and the oxygen-carbon-oxygen bond as a whole forms a monovalent anion, and a cation of a metal atom or an atomic group containing metal atoms, wherein the anion and the cation are ionically bonded.

2. An ionic composition comprising a diene carboxylate anion represented by Formula (1):

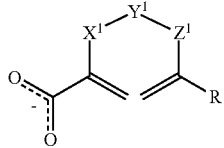

Formula (1)

wherein R represents a hydrogen atom or a methyl group; $X^1$ and $Z^1$ are the same and represent a methylene group, $Y^1$ is an oxygen atom; and oxygen-carbon-oxygen bonds shown by a dotted line and a solid line means that two carbon-oxygen bonds in each bond unit are equivalent to each other and the oxygen-carbon-oxygen bond as a whole forms a monovalent anion, and a cation of a metal atom or an atomic group containing metal atoms.

3. A polymerizable or curable composition comprising the salt of the diene carboxylic acid according to claim 1.

4. The polymerizable or curable composition according to claim 3,
further comprising a radical initiator and/or a dryer.

5. A method for polymerizing or curing the salt of the diene carboxylic acid according to claim 1,
comprising a step including at least one method selected from the group consisting of heating, irradiating with active energy beams, and exposing to an atmosphere including oxygen.

6. A polymerized or cured product produced by the polymerization or curing method according to claim 5.

7. A polymerizable or curable composition comprising the ionic composition according to claim 2.

8. The polymerizable or curable composition according to claim 7, further comprising a radical initiator and/or a dryer.

9. A method for polymerizing or curing the polymerizable or curable composition according to claim 3,
comprising a step including at least one method selected from the group consisting of heating, irradiating with active energy beams, and exposing to an atmosphere including oxygen.

10. A method for polymerizing or curing the polymerizable or curable composition according to claim 7,
comprising a step including at least one method selected from the group consisting of heating, irradiating with active energy beams, and exposing to an atmosphere including oxygen.

11. A method for polymerizing or curing the polymerizable or curable composition according to claim 4,
comprising a step including at least one method selected from the group consisting of heating, irradiating with active energy beams, and exposing to an atmosphere including oxygen.

12. A method for polymerizing or curing the polymerizable or curable composition according to claim 8,
comprising a step including at least one method selected from the group consisting of heating, irradiating with active energy beams, and exposing to an atmosphere including oxygen.

13. A polymerized or cured product produced by the polymerization or curing method according to claim 9.

14. A polymerized or cured product produced by the polymerization or curing method according to claim 7.

15. A polymerized or cured product produced by the polymerization or curing method according to claim 4.

16. A polymerized or cured product produced by the polymerization or curing method according to claim 8.

17. The ionic composition according to claim 2,
wherein the anion and the cation are ionically bonded.

18. An ionic salt comprising the ionic composition according to claim 2,
wherein the anion and the cation are ionically bonded.

19. A method for polymerizing or curing the ionic composition according to claim 2, comprising a step including at least one method selected from the group consisting of heating, irradiating with active energy beams, and exposing to an atmosphere including oxygen.

* * * * *